(12) United States Patent
Bush et al.

(10) Patent No.: US 8,153,807 B2
(45) Date of Patent: Apr. 10, 2012

(54) INHIBITORS OF 11-BETA-HYDROXYSTEROID DEHYDROGENASE 1

(75) Inventors: Julie Kay Bush, McCordsville, IN (US); Marvin Martin Hansen, Indianapolis, IN (US); Renhua Li, Fishers, IN (US); Thomas Edward Mabry, Indianapolis, IN (US); Nancy June Snyder, Lizton, IN (US); Owen Brendan Wallace, Westfield, IN (US); Yanping Xu, Noblesville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 805 days.

(21) Appl. No.: 12/297,873

(22) PCT Filed: Apr. 23, 2007

(86) PCT No.: PCT/US2007/067182
§ 371 (c)(1),
(2), (4) Date: Oct. 21, 2008

(87) PCT Pub. No.: WO2007/127688
PCT Pub. Date: Nov. 8, 2007

(65) Prior Publication Data
US 2009/0111809 A1     Apr. 30, 2009

Related U.S. Application Data

(60) Provisional application No. 60/745,475, filed on Apr. 24, 2006.

(51) Int. Cl.
C07D 405/00     (2006.01)
A61K 31/535     (2006.01)
A61K 31/445     (2006.01)

(52) U.S. Cl. ............... 546/208; 546/214; 514/235.5; 514/326

(58) Field of Classification Search ............ 546/208, 546/214; 514/235.5, 326
See application file for complete search history.

(56) References Cited

U.S. PATENT DOCUMENTS

| | | |
|---|---|---|
| 2008/0207691 A1 | 8/2008 | Aicher et al. |
| 2008/0214621 A1 | 9/2008 | Aicher et al. |
| 2008/0275043 A1 | 11/2008 | Aicher et al. |
| 2009/0069326 A1 | 3/2009 | Allen et al. |
| 2009/0088428 A1 | 4/2009 | Saeed et al. |
| 2009/0088430 A1 | 4/2009 | Wallace et al. |
| 2009/0099180 A1 | 4/2009 | Mabry et al. |
| 2009/0099182 A1 | 4/2009 | Li et al. |
| 2009/0111800 A1 | 4/2009 | Aicher et al. |
| 2009/0156571 A1 | 6/2009 | Aicher et al. |
| 2009/0239911 A1 | 9/2009 | Wallace et al. |
| 2009/0264650 A1 | 10/2009 | Yamashita et al. |
| 2009/0275613 A1 | 11/2009 | Li et al. |
| 2011/0159005 A1* | 6/2011 | Jacobson et al. ........ 424/158.1 |

FOREIGN PATENT DOCUMENTS

| | | |
|---|---|---|
| EP | 1864971 | 12/2007 |
| WO | WO 2004/056744 | 7/2004 |
| WO | WO 2005/108360 | 11/2005 |
| WO | WO 2005/108361 | 11/2005 |
| WO | WO 2006/040329 | 4/2006 |
| WO | WO 2006/049952 | 5/2006 |
| WO | WO 2006/053024 | 5/2006 |
| WO | WO 2006/068991 | 6/2006 |
| WO | WO 2006/068992 | 6/2006 |
| WO | WO 2006/104280 A | 10/2006 |
| WO | WO 2007/084314 | 7/2007 |
| WO | WO 2007/124254 | 11/2007 |
| WO | WO 2007/124329 | 11/2007 |
| WO | WO 2007/124337 | 11/2007 |
| WO | WO 2007/127693 | 11/2007 |
| WO | WO 2007/127704 | 11/2007 |
| WO | WO 2007/127726 | 11/2007 |
| WO | WO 2007/127763 | 11/2007 |
| WO | WO 2007/127765 | 11/2007 |
| WO | WO 2007/127901 | 11/2007 |
| WO | WO 2008/157752 | 12/2008 |

OTHER PUBLICATIONS

Yeh et al.: Discovery of orally active butyrolactam 11 β-HSD1 inhibitors, Bioorganic & Medicinal Chemistry Letters, Nov. 1, 2006, 16(21), pp. 5555-5560.

Schuster, Daniela et al.: The Discovery of New 11β-Hydroxysteroid Dehydrogenase Type 1 Inhibitors by Common Feature Pharmacophore Modeling and Virtual Screening, J. Medicinal Chemistry, 2006, 49, pp. 3454-3466.

Konno et al.: Electrolytic Partial Fluorination of Organic Compounds. 6. Highly Regioselective Eletrochemical Monofluorination of Aliphatic Nitrogen-Containing Heterocycles, Tetrahedron Letters, 1992, vol. 33, No. 46, pp. 7017-7020.

* cited by examiner

*Primary Examiner* — Janet Andres
*Assistant Examiner* — John Mabry
(74) *Attorney, Agent, or Firm* — Dan L. Wood

(57) ABSTRACT

The present invention discloses novel compounds of Formula I: (I) having 11-HSD type 1 antagonist activity, as well as methods for preparing such compounds. In another embodiment, the invention discloses pharmaceutical compositions comprising compounds of Formula I, as well as methods of using the compounds and compositions to treat diabetes, hyperglycemia, obesity, hypertension, hyperlipidemia, metabolic syndrome, and other conditions associated with 11-HSD type 1 activity.

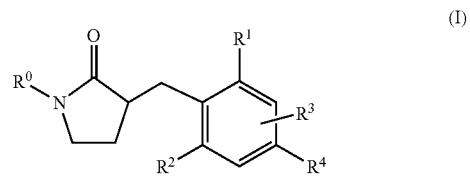

(I)

22 Claims, No Drawings

INHIBITORS OF 11-BETA-HYDROXYSTEROID DEHYDROGENASE 1

This is the national phase application, under 35 USC 371, for PCT/US2007/067182, filed Apr. 23, 2007, which claims the benefit, under 35 USC 119(e), of U.S. provisional application 60/745,475 filed Apr. 24, 2006.

This invention relates to compounds that are inhibitors of 11-β-hydroxysteroid dehydrogenase type 1 ("11-β-HSD1"), and to pharmaceutical compositions thereof, and the uses of these compounds and compositions in the treatment of the human or animal body, and to novel intermediates useful in preparation of the inhibitors. The present compounds show potent and selective inhibition of 11-β-HSD1, and as such are useful in the treatment of disorders responsive to the modulation of 11-β-HSD1, such as diabetes, metabolic syndrome, cognitive disorders, and the like.

Glucocorticoids acting in the liver, adipose tissue, and muscle, are important regulators of glucose, lipid, and protein metabolism. Chronic glucocorticoid excess is associated with insulin resistance, visceral obesity, hypertension, and dyslipidemia, which also represent the classical hallmarks of metabolic syndrome. 11-β-HSD1 catalyses the conversion of inactive cortisone to active cortisol, and has been implicated in the development of metabolic syndrome. Evidence in rodents and humans links 11-β-HSD1 to metabolic syndrome. Evidence suggests that a drug which specifically inhibits 11-β-HSD1 in type 2 diabetic patients will lower blood glucose by reducing hepatic gluconeogenesis, reduce central obesity, improve atherogenic lipoprotein phenotypes, lower blood pressure, and reduce insulin resistance. Insulin effects in muscle will be enhanced, and insulin secretion from the beta cells of the islet may also be increased. Evidence from animal and human studies also indicates that an excess of glucocorticoids impair cognitive function. Recent results indicate that inactivation of 11-β-HSD1 enhances memory function in both men and mice. The 11-β-HSD inhibitor carbenoxolone was shown to improve cognitive function in healthy elderly men and type 2 diabetics, and inactivation of the 11-β-HSD1 gene prevented aging-induced impairment in mice. Selective inhibition of 11-β-HSD1 with a pharmaceutical agent has recently been shown to improve memory retention in mice.

A number of publications have appeared in recent years reporting agents that inhibit 11-β-HSD1. See International Application WO2004/056744 which discloses adamantyl acetamides as inhibitors of 11-β-HSD, International Application WO2005/108360 which discloses pyrrolidin-2-one and piperidin-2-one derivatives as inhibitors of 11-β-HSD, and International Application WO2005/108361 which discloses adamantyl pyrrolidin-2-one derivatives as inhibitors of 11-β-HSD. In spite of the number of treatments for diseases that involve 11-β-HSD1, the current therapies suffer from one or more inadequacies, including poor or incomplete efficacy, unacceptable side effects, and contraindications for certain patient populations. Thus, there remains a need for an improved treatment using alternative or improved pharmaceutical agents that inhibit 11-β-HSD1 and treat the diseases that could benefit from 11-β-HSD1 inhibition. The present invention provides such a contribution to the art based on the finding that a novel class of compounds has a potent and selective inhibitory activity on 11-β-HSD1. The present invention is distinct in the particular structures and their activities. There is a continuing need for new methods of treating diabetes, metabolic syndrome, and cognitive disorders, and it is an object of this invention to meet these and other needs.

The present invention provides a compound structurally represented by the formula:

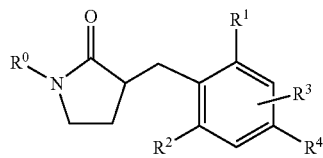

or a pharmaceutically acceptable salt thereof, wherein $R^0$ is

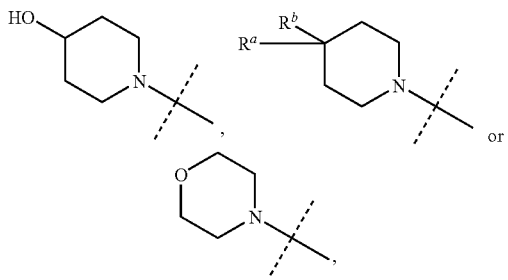

wherein the dashed line represents the point of attachment to the $R^0$ position; wherein $R^a$ is -halogen; $R^b$ is —H or halogen;

$R^1$ is —H, -halogen, —O—$CH_3$ (optionally substituted with one to three halogens), or —$CH_3$ (optionally substituted with one to three halogens);

$R^2$ is —H, -halogen, —O—$CH_3$ (optionally substituted with one to three halogens), or —$CH_3$ (optionally substituted with one to three halogens);

$R^3$ is —H or -halogen;

$R^4$ is

—OH, -halogen, —CN, —($C_1$-$C_4$)alkyl (optionally substituted with one to three halogens), —O—($C_1$-$C_6$)alkyl (optionally substituted with one to three halogens), —$SCF_3$, —C(O)O($C_1$-$C_4$)alkyl, —O—$CH_2$—C(O)$NH_2$, —($C_3$-$C_8$)cycloalkyl, —O-phenyl-C(O)O—($C_1$-$C_4$)alkyl, —$CH_2$-phenyl, —$NHSO_2$—($C_1$-$C_4$)alkyl, —$NHSO_2$-phenyl($R^{21}$)($R^{21}$), —($C_1$-$C_4$)alkyl-C(O)N($R^{10}$)($R^{11}$),

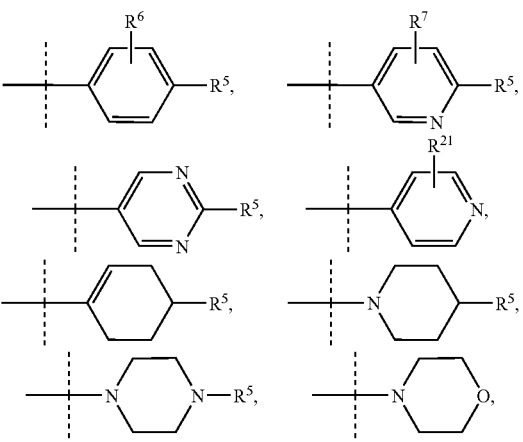

-continued

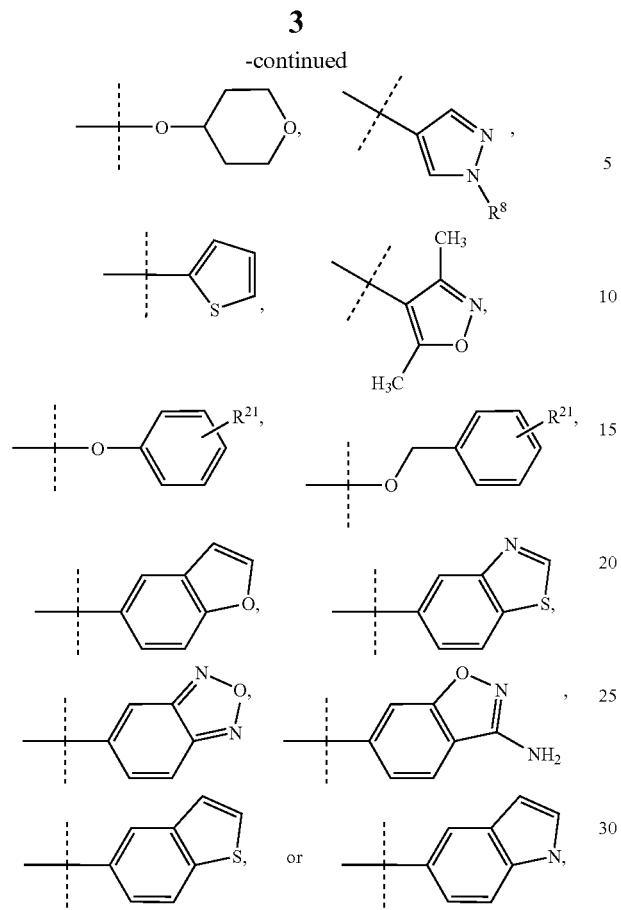

wherein the dashed line represents the point of attachment to the $R^4$ position;

$R^5$ is
- —H, -halogen, —OH, —CN, —($C_1$-$C_4$)alkyl(optionally substituted with 1 to 3 halogens), —C(O)OH, —C(O)O—($C_1$-$C_4$)alkyl, —C(O)—($C_1$-$C_4$)alkyl,
- —O—($C_1$-$C_4$)alkyl(optionally substituted with 1 to 3 halogens),
- —$SO_2$—($C_1$-$C_4$)alkyl, —N($R^8$)($R^8$), -phenyl($R^{21}$)($R^{21}$), —C(O)—NH—($C_3$-$C_6$)cycloalkyl,

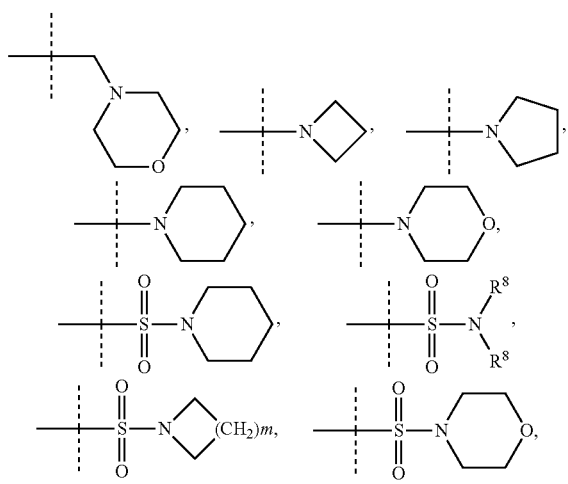

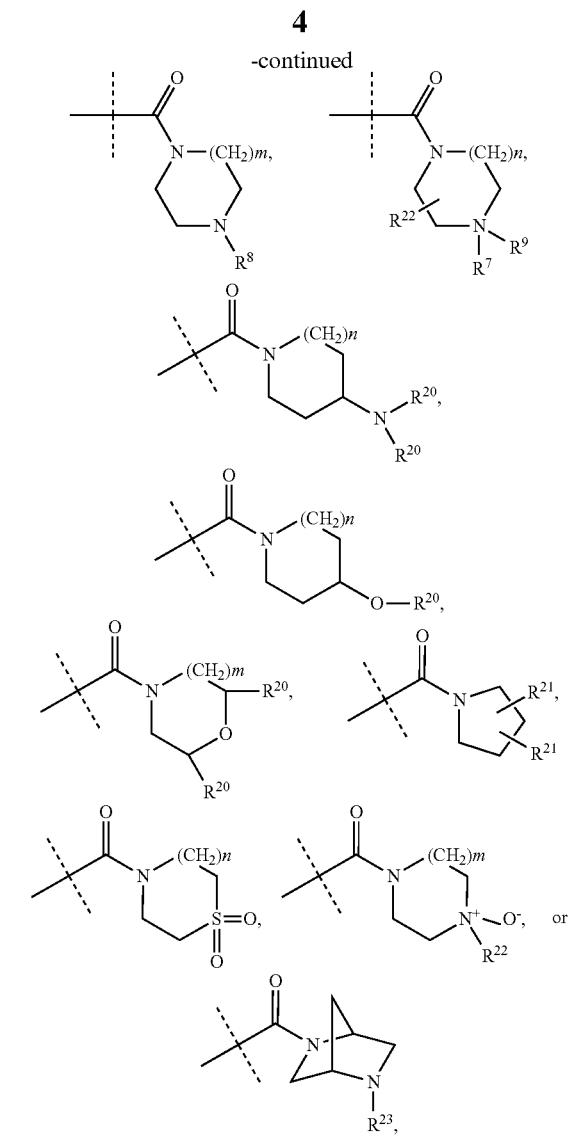

wherein the dashed line represents the point of attachment to the position indicated by $R^5$;
wherein m is 1, 2, or 3;
wherein n is 0, 1, or 2, and wherein when n is 0, then "$(CH_2)n$" is a bond;

$R^6$ is
- —H, -halogen, —CN, or —($C_1$-$C_4$)alkyl(optionally substituted with 1 to 3 halogens);

$R^7$ is
- —H, -halogen, or —($C_1$-$C_4$)alkyl(optionally substituted with 1 to 3 halogens);

$R^8$ is independently at each occurrence
- —H, —($C_1$-$C_6$)alkyl(optionally substituted with 1 to 3 halogens),
- —C(O)($C_1$-$C_6$)alkyl(optionally substituted with 1 to 3 halogens),
- —C(O)—($C_3$-$C_8$)cycloalkyl, —S($O_2$)—($C_3$-$C_8$)cycloalkyl or
- —S($O_2$)—($C_1$-$C_3$)alkyl(optionally substituted with 1 to 3 halogens);

$R^9$ is —H or -halogen;

$R^{10}$ and $R^{11}$ are each independently
- —H or —($C_1$-$C_4$)alkyl, or $R^{10}$ and $R^{11}$ taken together with the nitrogen to which they are attached form piperidinyl, piperazinyl, or pyrrolidinyl;

$R^{20}$ is independently at each occurrence —H, or —$(C_1$-$C_3)$ alkyl(optionally substituted with 1 to 3 halogens);

$R^{21}$ is independently at each occurrence —H, -halogen, —$(C_1$-$C_3)$alkyl(optionally substituted with 1 to 3 halogens), —CN, or —C(O)—N($R^{22}$)($R^{22}$) (wherein optionally the two occurrences of $R^{22}$ along with the nitrogen to which they are attached form azetidinyl, pyrrolidinyl, or piperidinyl);

$R^{22}$ is independently at each occurrence —H or —$(C_1$-$C_6)$ alkyl(optionally substituted with 1 to 3 halogens); and $R^{23}$ is independently at each occurrence —H, —$(C_1$-$C_4)$ alkyl, or —C(O)O—$(C_1$-$C_4)$alkyl.

In another embodiment the present invention provides a compound structurally represented by formula I:

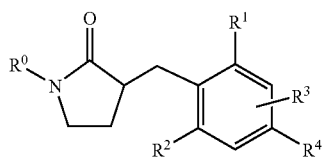

(I)

or a pharmaceutically acceptable salt thereof, wherein $R^0$ is

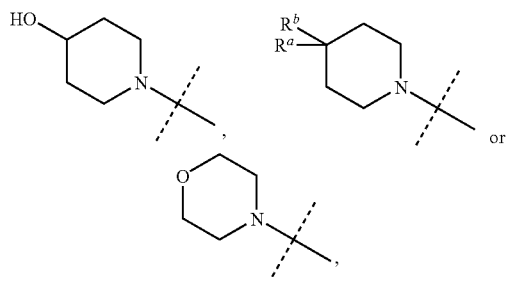

wherein the dashed line represents the point of attachment to the $R^0$ position in formula I; wherein $R^a$ is -halogen; $R^b$ is —H or halogen;

$R^1$ is —H, -halogen, —O—$CH_3$ (optionally substituted with one to three halogens), or —$CH_3$ (optionally substituted with one to three halogens);

$R^2$ is —H, -halogen, —O—$CH_3$ (optionally substituted with one to three halogens), or —$CH_3$ (optionally substituted with one to three halogens);

$R^3$ is —H or -halogen;

$R^4$ is

—OH, -halogen, —CN, —$(C_1$-$C_4)$alkyl(optionally substituted with one to three halogens), —O—$(C_1$-$C_6)$alkyl (optionally substituted with one to three halogens), —$SCF_3$, —C(O)O$(C_1$-$C_4)$alkyl, —O—$CH_2$—C(O) $NH_2$, —$(C_3$-$C_8)$cycloalkyl, —O-phenyl-C(O)O—$(C_1$-$C_4)$alkyl, —$CH_2$-phenyl, —$NHSO_2$—$(C_1$-$C_4)$alkyl, —$NHSO_2$-phenyl($R^{21}$)($R^{21}$), —$(C_1$-$C_4)$alkyl-C(O)N ($R^{10}$)($R^{11}$),

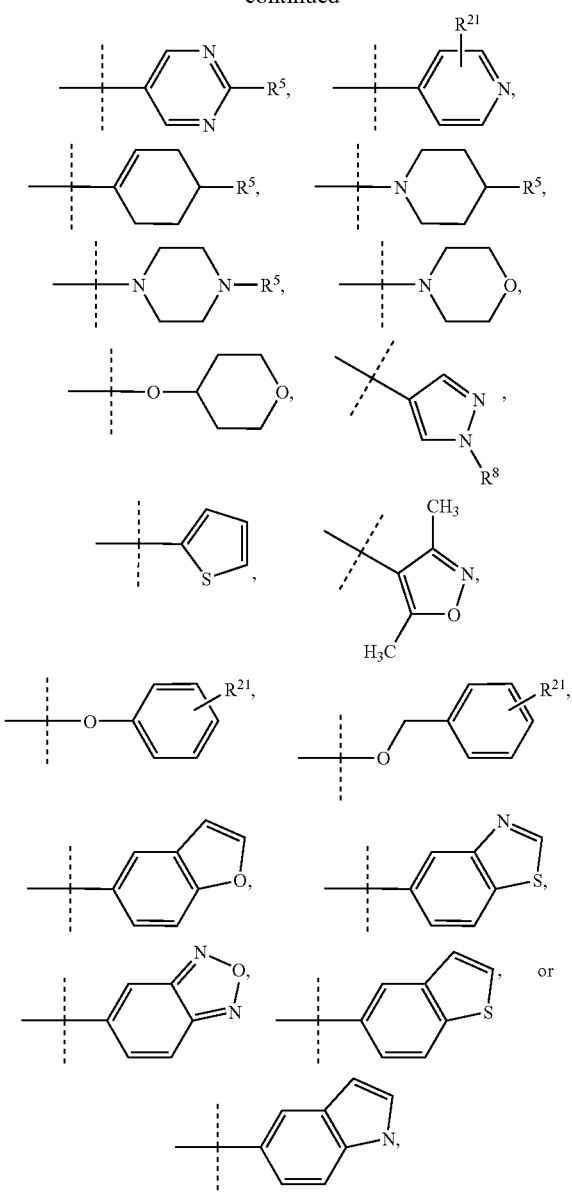

wherein the dashed line represents the point of attachment to the $R^4$ position in formula I;

$R^5$ is

—H, -halogen, —OH, —CN, —$(C_1$-$C_4)$alkyl(optionally substituted with 1 to 3 halogens), —C(O)OH, —C(O) O—$(C_1$-$C_4)$alkyl, —C(O)—$(C_1$-$C_4)$alkyl, —O—$(C_1$-$C_4)$alkyl(optionally substituted with 1 to 3 halogens), —$SO_2$—$(C_1$-$C_4)$alkyl, —N($R^8$)($R^8$), -phenyl($R^{21}$) ($R^{21}$), —C(O)—NH—$(C_3$-$C_6)$cycloalkyl,

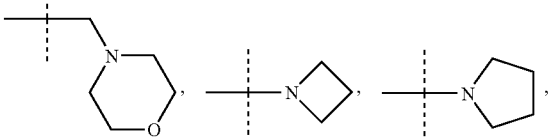

-continued

[Chemical structures: piperidinyl-N, morpholinyl-N, sulfonyl-piperidinyl, sulfonyl-NR⁸R⁸, sulfonyl-azetidinyl-(CH₂)m, sulfonyl-morpholinyl, acyl-piperazinyl-(CH₂)m-R⁸, acyl-piperidinyl-(CH₂)n with R²² R⁹ R⁷, acyl-piperidinyl-(CH₂)n-NR²⁰R²⁰, acyl-piperidinyl-(CH₂)n-O-R²⁰, acyl-morpholinyl-(CH₂)m with R²⁰ R²⁰, acyl-pyrrolidinyl with R²¹ R²¹, acyl-thiomorpholinyl-(CH₂)n-S(O)₂, acyl-piperazinyl-(CH₂)m-N⁺(O⁻)(R²²), or acyl-azabicyclic-R²³]

wherein the dashed line represents the point of attachment to the position indicated by $R^5$;

wherein m is 1, 2, or 3;

wherein n is 0, 1, or 2, and wherein when n is 0, then "(CH₂)n" is a bond;

$R^6$ is
 —H, -halogen, —CN, or —(C₁-C₄)alkyl(optionally substituted with 1 to 3 halogens);

$R^7$ is
 —H, -halogen, or —(C₁-C₄)alkyl(optionally substituted with 1 to 3 halogens);

$R^8$ is independently at each occurrence
 —H, —(C₁-C₆)alkyl(optionally substituted with 1 to 3 halogens),
 —C(O)(C₁-C₆)alkyl(optionally substituted with 1 to 3 halogens),
 —C(O)—(C₃-C₈)cycloalkyl, —S(O₂)—(C₃-C₈)cycloalkyl or
 —S(O₂)—(C₁-C₃)alkyl(optionally substituted with 1 to 3 halogens);

$R^9$ is —H or -halogen;

$R^{10}$ and $R^{11}$ are each independently
 —H or —(C₁-C₄)alkyl, or $R^{10}$ and $R^{11}$ taken together with the nitrogen to which they are attached form piperidinyl, piperazinyl, or pyrrolidinyl;

$R^{20}$ is independently at each occurrence —H, or —(C₁-C₃)alkyl(optionally substituted with 1 to 3 halogens);

$R^{21}$ is independently at each occurrence —H, -halogen, or —(C₁-C₃)alkyl(optionally substituted with 1 to 3 halogens), —CN, —C(O)—N(R²²)(R²²) (wherein optionally the two occurrences of R²² along with the nitrogen to which they are attached form azetidinyl, pyrrolidinyl, or piperidinyl);

$R^{22}$ is independently at each occurrence —H or —(C₁-C₆)alkyl(optionally substituted with 1 to 3 halogens); and $R^{23}$ is independently at each occurrence —H, —(C₁-C₄)alkyl, or —C(O)O—(C₁-C₄)alkyl.

The present invention provides compounds of formula I that are useful as potent and selective inhibition of 11-β-HSD1. The present invention further provides a pharmaceutical composition which comprises a compound of Formula I, or a pharmaceutical salt thereof, and a pharmaceutically acceptable carrier, diluent, or excipient. In addition, the present invention provides a method for the treatment of metabolic syndrome, and related disorders, which comprise administering to a patient in need thereof an effective amount of a compound of formula I or a pharmaceutically acceptable salt thereof.

In one embodiment, the present invention provides compounds of Formula I or a pharmaceutically acceptable salt thereof as described in detail above. While all of the compounds of the present invention are useful, certain of the compounds are particularly interesting and are preferred. The following listings set out several groups of preferred compounds.

In another embodiment the invention provides a compound structurally represented by formula I, or a pharmaceutically acceptable salt thereof, wherein $R^0$ is

[Chemical structures: 4-hydroxypiperidinyl, 4-R^a,R^b-piperidinyl, or morpholinyl]

wherein the dashed line represents the point of attachment to the $R^0$ position in formula I; wherein $R^a$ is -halogen; $R^b$ is —H or halogen;

$R^1$ is -halogen; $R^2$ is -halogen; $R^3$ is —H or -halogen;

$R^4$ is
 —OH, -halogen, —CN, —(C₁-C₄)alkyl(optionally substituted with one to three halogens), —(C₁-C₆)alkoxy(optionally substituted with one to three halogens), —SCF₃, —C(O)O(C₁-C₄)alkyl, —O—CH₂—C(O)NH₂, —(C₃-C₈)cycloalkyl, —O-phenyl-C(O)O—(C₁-C₄)alkyl, —CH₂-phenyl, —NHSO₂—(C₁-C₄)alkyl, —NHSO₂-phenyl(R²¹)(R²¹), —(C₁-C₄)alkyl-C(O)N(R¹⁰)(R¹¹),

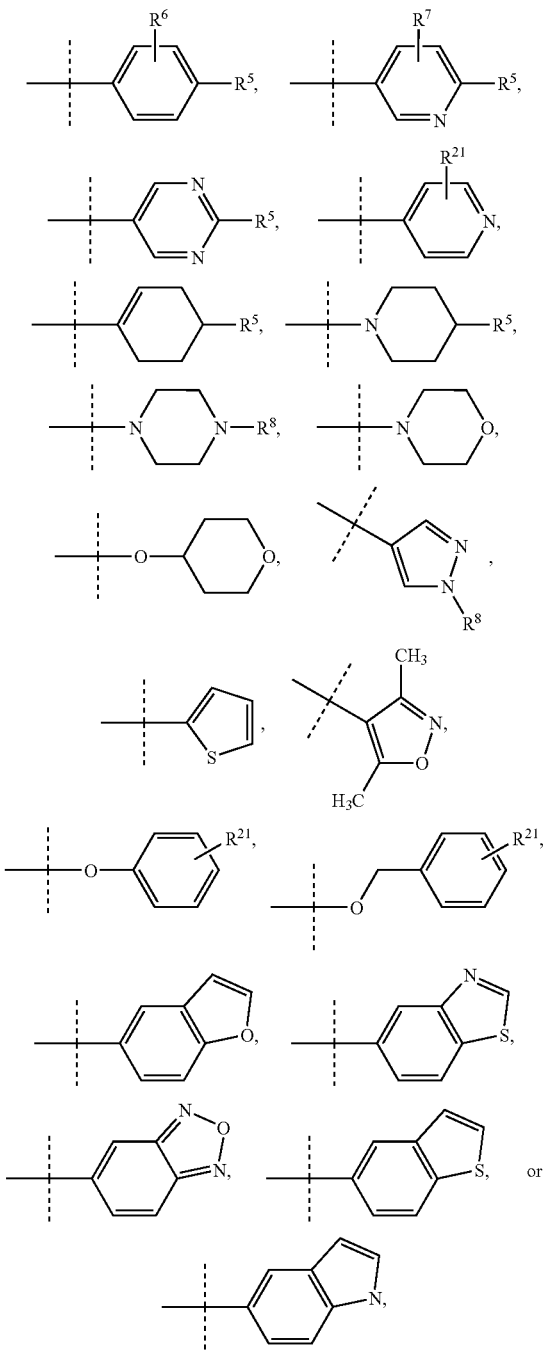

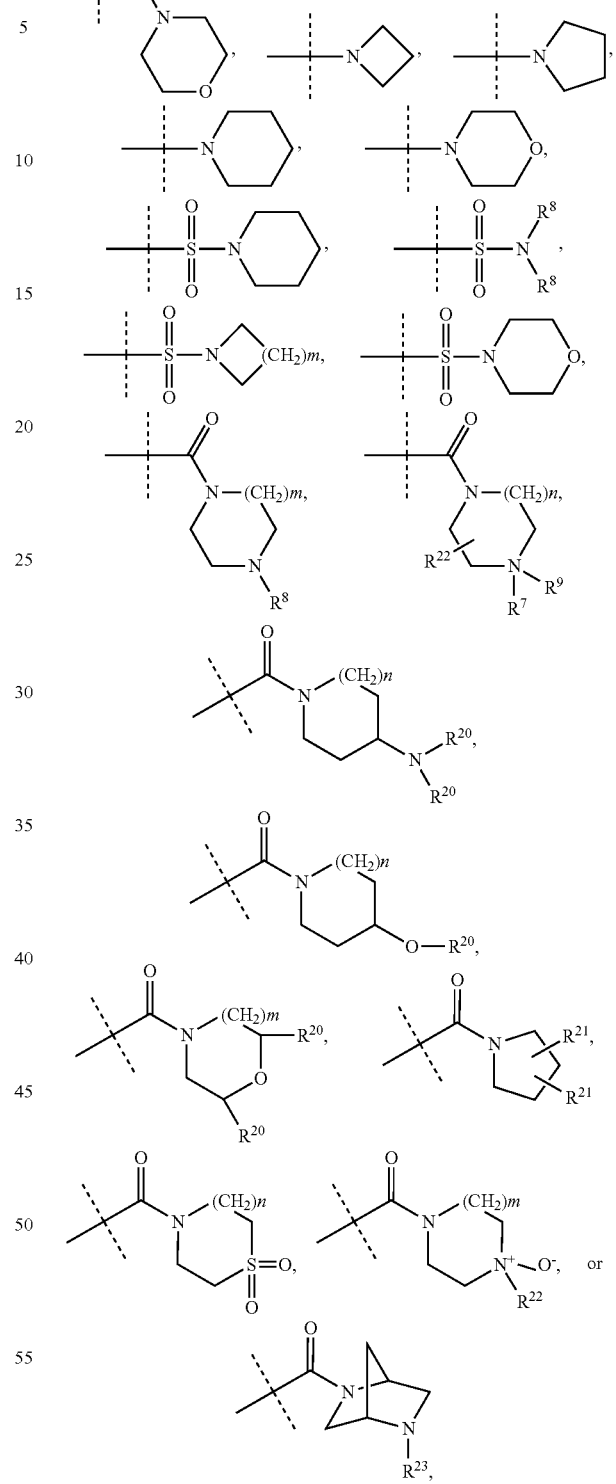

wherein the dashed line represents the point of attachment to the R⁴ position in formula I;

R⁵ is
- —H, -halogen, —OH, —CN, —(C₁-C₄)alkyl(optionally substituted with 1 to 3 halogens), —C(O)OH, —C(O)O—(C₁-C₄)alkyl, —C(O)—(C₁-C₄)alkyl, —O—(C₁-C₄)alkyl(optionally substituted with 1 to 3 halogens), —SO₂—(C₁-C₄)alkyl, —N(R⁸)(R⁸), -phenyl(R²¹)(R²¹), —C(O)—NH—(C₃-C₆)cycloalkyl, wherein the dashed line represents the point of attachment to the position indicated by R⁵;

wherein m is 1, 2, or 3;

wherein n is 0, 1, or 2, and wherein when n is 0, then "(CH₂)n" is a bond;

R⁶ is
— —H, -halogen, —CN, or —(C₁-C₄)alkyl(optionally substituted with 1 to 3 halogens);

R⁷ is
— —H, -halogen, or —(C₁-C₄)alkyl(optionally substituted with 1 to 3 halogens);

R⁸ is independently at each occurrence
— —H, —(C₁-C₆)alkyl(optionally substituted with 1 to 3 halogens),
— —C(O)(C₁-C₆)alkyl(optionally substituted with 1 to 3 halogens),
— —C(O)—(C₃-C₈)cycloalkyl, —S(O₂)—(C₃-C₈)cycloalkyl or
— —S(O₂)—(C₁-C₃)alkyl(optionally substituted with 1 to 3 halogens);

R⁹ is —H or -halogen;

R¹⁰ and R¹¹ are each independently
— —H or —(C₁-C₄)alkyl, or R¹⁰ and R¹¹ taken together with the nitrogen to which they are attached form piperidinyl, piperazinyl, or pyrrolidinyl;

R²⁰ is independently at each occurrence —H, or —(C₁-C₃)alkyl(optionally substituted with 1 to 3 halogens);

R²¹ is independently at each occurrence —H, -halogen, or —(C₁-C₃)alkyl(optionally substituted with 1 to 3 halogens), —CN, —C(O)—N(R²²)(R²²) (wherein optionally the two occurrences of R²² along with the nitrogen to which they are attached form azetidinyl, pyrrolidinyl, or piperidinyl);

R²² is independently at each occurrence —H or —(C₁-C₆)alkyl(optionally substituted with 1 to 3 halogens); and R²³ is independently at each occurrence —H, —(C₁-C₄)alkyl, or —C(O)O—(C₁-C₄)alkyl.

In another embodiment the invention provides a compound structurally represented by formula I, or a pharmaceutically acceptable salt thereof, wherein R⁰ is

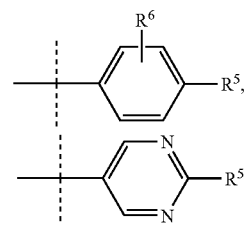

wherein the dashed line represents the point of attachment to the R⁰ position in formula I; wherein Rᵃ is -halogen; Rᵇ is —H or halogen;

R¹ is -chlorine, -fluorine, or -bromine; R² is chlorine, -fluorine, or -bromine; R³ is —H or -halogen;

R⁴ is

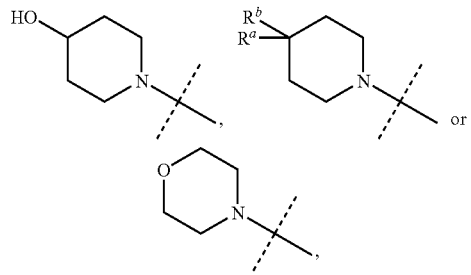

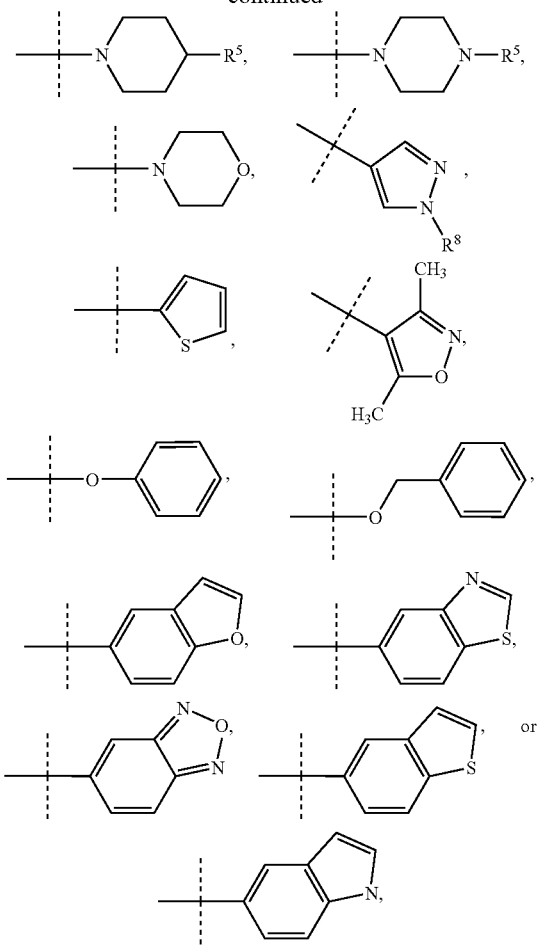

wherein the dashed line represents the point of attachment to the R⁴ position in formula I;

R⁵ is
— —H, -halogen, —OH, —CN, —(C₁-C₄)alkyl(optionally substituted with 1 to 3 halogens), —C(O)OH, —C(O)O—(C₁-C₄)alkyl, —C(O)—(C₁-C₄)alkyl,
— —O—(C₁-C₄)alkyl(optionally substituted with 1 to 3 halogens), —SO₂—(C₁-C₄)alkyl,
— —N(R⁸)(R⁸), -phenyl(R²¹)(R²¹), —C(O)—NH—(C₃-C₆)cycloalkyl,

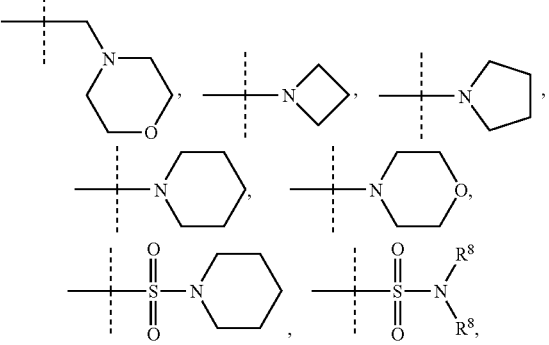

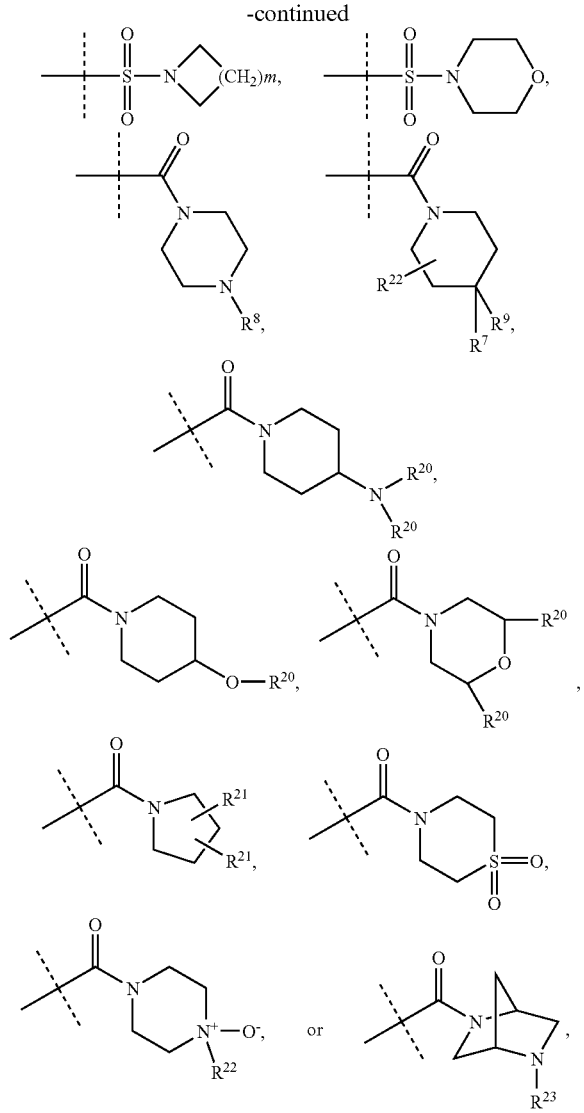

wherein the dashed line represents the point of attachment to the position indicated by $R^5$; wherein m is 1, 2, or 3;

$R^6$ is
—H, -halogen, —CN, or —(C$_1$-C$_4$)alkyl(optionally substituted with 1 to 3 halogens);

$R^7$ is
—H, -halogen, or —(C$_1$-C$_4$)alkyl(optionally substituted with 1 to 3 halogens);

$R^8$ is independently at each occurrence
—H, —(C$_1$-C$_6$)alkyl(optionally substituted with 1 to 3 halogens),
—C(O)(C$_1$-C$_6$)alkyl(optionally substituted with 1 to 3 halogens),
—C(O)—(C$_3$-C$_8$)cycloalkyl, —S(O$_2$)—(C$_3$-C$_8$)cycloalkyl or
—S(O$_2$)—(C$_1$-C$_3$)alkyl(optionally substituted with 1 to 3 halogens);

$R^9$ is —H or -halogen;

$R^{20}$ is independently at each occurrence —H, or —(C$_1$-C$_3$)alkyl(optionally substituted with 1 to 3 halogens);

$R^{21}$ is independently at each occurrence —H, -halogen, or —(C$_1$-C$_3$)alkyl(optionally substituted with 1 to 3 halogens), —CN, —C(O)—N(R$^{22}$)(R$^{22}$) (wherein optionally the two occurrences of $R^{22}$ along with the nitrogen to which they are attached form azetidinyl, pyrrolidinyl, or piperidinyl);

$R^{22}$ is independently at each occurrence —H or —(C$_1$-C$_6$)alkyl(optionally substituted with 1 to 3 halogens); and $R^{23}$ is independently at each occurrence —H, —(C$_1$-C$_4$)alkyl, or —C(O)O—(C$_1$-C$_4$)alkyl.

In another embodiment the invention provides a compound structurally represented by formula I, or a pharmaceutically acceptable salt thereof, wherein $R^0$ is

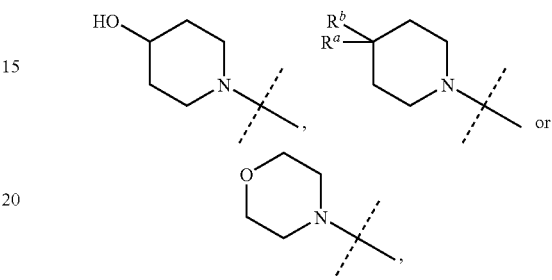

wherein the dashed line represents the point of attachment to the $R^0$ position in formula I; wherein $R^a$ is -halogen; $R^b$ is —H or halogen;

$R^1$ is -chlorine, -fluorine, or -bromine; $R^2$ is chlorine, -fluorine, or -bromine; $R^3$ is —H or -halogen;

$R^4$ is

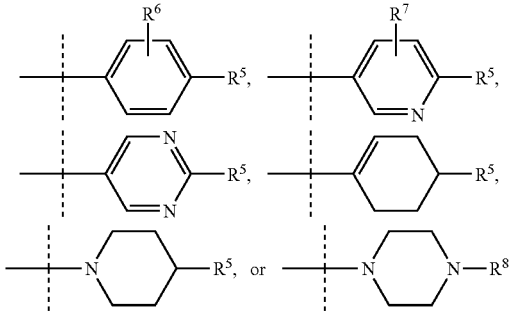

wherein the dashed line represents the point of attachment to the $R^4$ position in formula I;

$R^5$ is
—H, -halogen, —(C$_1$-C$_4$)alkyl(optionally substituted with 1 to 3 halogens), —C(O)OH, —C(O)O—(C$_1$-C$_4$)alkyl, —C(O)—(C$_1$-C$_4$)alkyl, —O—(C$_1$-C$_4$)alkyl(optionally substituted with 1 to 3 halogens), —SO$_2$—(C$_1$-C$_4$)alkyl, —N(R$^8$)(R$^8$),

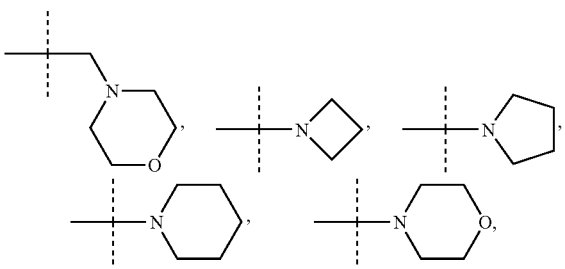

-continued

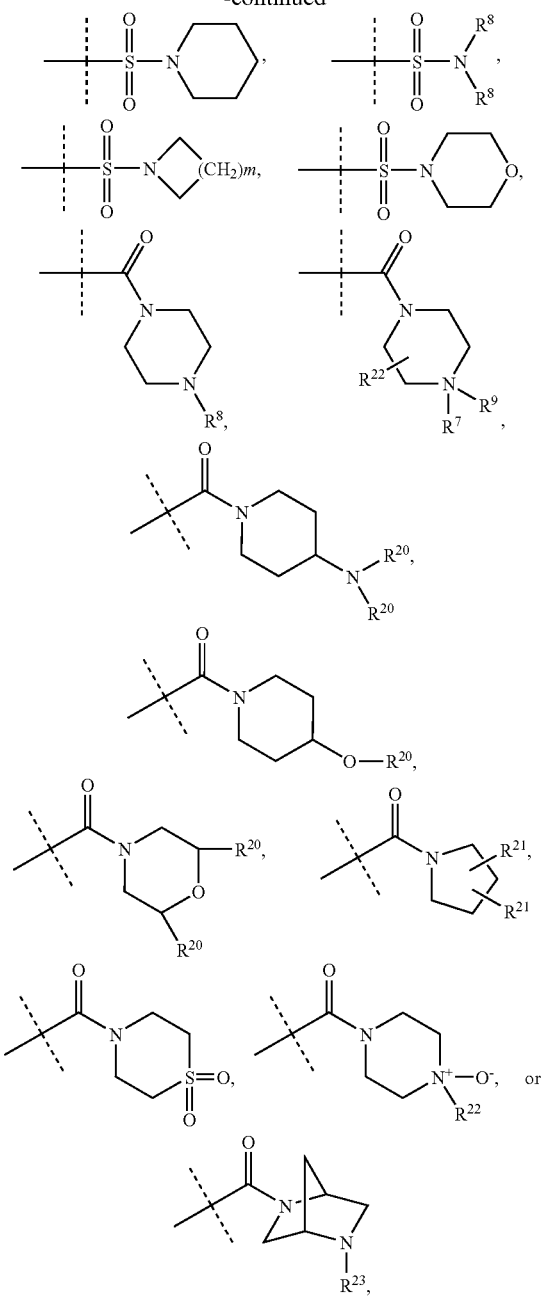

wherein the dashed line represents the point of attachment to the position indicated by $R^5$; wherein m is 1, 2, or 3;

$R^6$ is
—H, -halogen, —CN, or —$(C_1$-$C_4)$alkyl(optionally substituted with 1 to 3 halogens);

$R^7$ is
—H, -halogen, or —$(C_1$-$C_4)$alkyl(optionally substituted with 1 to 3 halogens);

$R^8$ is independently at each occurrence
—H, —$(C_1$-$C_6)$alkyl(optionally substituted with 1 to 3 halogens),
—C(O)$(C_1$-$C_6)$alkyl(optionally substituted with 1 to 3 halogens),
—C(O)—$(C_3$-$C_8)$cycloalkyl, —S($O_2$)—$(C_3$-$C_8)$cycloalkyl or —S($O_2$)—$(C_1$-$C_3)$alkyl(optionally substituted with 1 to 3 halogens);

$R^9$ is —H or -halogen;

$R^{20}$ is independently at each occurrence —H, or —$(C_1$-$C_3)$alkyl(optionally substituted with 1 to 3 halogens);

$R^{21}$ is independently at each occurrence —H, -halogen, or —$(C_1$-$C_3)$alkyl(optionally substituted with 1 to 3 halogens), —CN, —C(O)—N($R^{22}$)($R^{22}$) (wherein optionally the two occurrences of $R^{22}$ along with the nitrogen to which they are attached form azetidinyl, pyrrolidinyl, or piperidinyl);

$R^{22}$ is independently at each occurrence —H or —$(C_1$-$C_6)$alkyl(optionally substituted with 1 to 3 halogens); and $R^{23}$ is independently at each occurrence —H, —$(C_1$-$C_4)$alkyl, or —C(O)O—$(C_1$-$C_4)$alkyl.

In another embodiment the invention provides a compound structurally represented by formula I, or a pharmaceutically acceptable salt thereof, wherein $R^0$ is

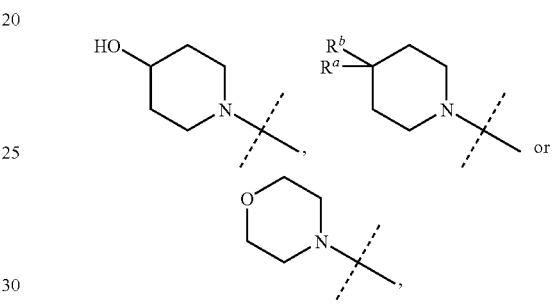

wherein the dashed line represents the point of attachment to the $R^0$ position in formula I; wherein $R^a$ is -halogen; $R^b$ is —H or halogen;

$R^1$ is -chlorine, -fluorine, or -bromine; $R^2$ is chlorine, -fluorine, or -bromine; $R^3$ is —H or -halogen;

$R^4$ is

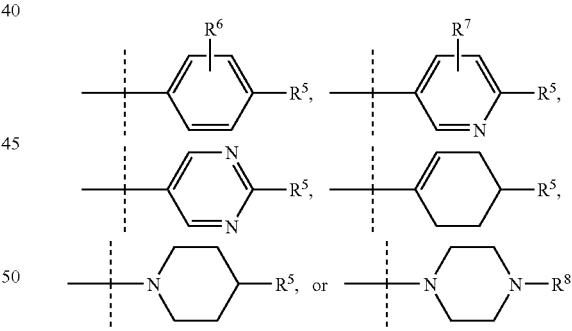

wherein the dashed line represents the point of attachment to the $R^4$ position in formula I;

$R^5$ is

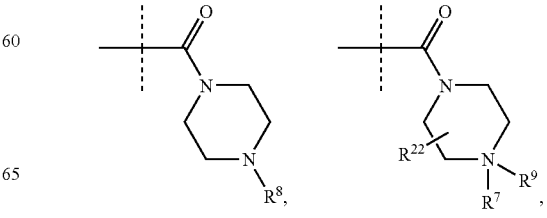

-continued wherein the dashed line represents the point of attachment to the position indicated by $R^5$;

$R^6$ is
— —H, -halogen, —CN, or —($C_1$-$C_4$)alkyl(optionally substituted with 1 to 3 halogens);

$R^7$ is
— —H, -halogen, or —($C_1$-$C_4$)alkyl(optionally substituted with 1 to 3 halogens);

$R^8$ is independently at each occurrence
— —H, —($C_1$-$C_6$)alkyl(optionally substituted with 1 to 3 halogens),
— —C(O)($C_1$-$C_6$)alkyl(optionally substituted with 1 to 3 halogens),
— —C(O)—($C_3$-$C_8$)cycloalkyl, —S($O_2$)—($C_3$-$C_8$)cycloalkyl or
— —S($O_2$)—($C_1$-$C_3$)alkyl(optionally substituted with 1 to 3 halogens);

$R^9$ is —H or -halogen;

$R^{20}$ is independently at each occurrence —H, or —($C_1$-$C_3$)alkyl(optionally substituted with 1 to 3 halogens);

$R^{21}$ is independently at each occurrence —H, -halogen, or —($C_1$-$C_3$)alkyl(optionally substituted with 1 to 3 halogens), —CN, —C(O)—N($R^{22}$)($R^{22}$) (wherein optionally the two occurrences of $R^{22}$ along with the nitrogen to which they are attached form azetidinyl, pyrrolidinyl, or piperidinyl);

$R^{22}$ is independently at each occurrence —H or —($C_1$-$C_6$)alkyl(optionally substituted with 1 to 3 halogens); and $R^{23}$ is independently at each occurrence —H, —($C_1$-$C_4$)alkyl, or —C(O)O—($C_1$-$C_4$)alkyl.

In another embodiment the invention provides a compound structurally represented by formula I, or a pharmaceutically acceptable salt thereof, wherein $R^0$ is wherein the dashed line represents the point of attachment to the $R^0$ position in formula I; wherein $R^a$ is -halogen; $R^b$ is —H or halogen;

$R^1$ is -chlorine, -fluorine, or -bromine; $R^2$ is chlorine, -fluorine, or -bromine; $R^3$ is —H or -halogen;

$R^4$ is wherein the dashed line represents the point of attachment to the $R^4$ position in formula I;

$R^5$ is wherein the dashed line represents the point of attachment to the position indicated by $R^5$; wherein m is 1, 2, or 3;

$R^6$ is
— —H, -halogen, —CN, or —($C_1$-$C_4$)alkyl(optionally substituted with 1 to 3 halogens);

$R^7$ is
— —H, -halogen, or —($C_1$-$C_4$)alkyl(optionally substituted with 1 to 3 halogens); and $R^8$ is independently at each occurrence
— —H, —($C_1$-$C_6$)alkyl(optionally substituted with 1 to 3 halogens),
— —C(O)($C_1$-$C_6$)alkyl(optionally substituted with 1 to 3 halogens), —C(O)—(C₃-C₈)cycloalkyl, —S(O₂)—(C₃-C₈)cycloalkyl or —S(O₂)—(C₁-C₃)alkyl(optionally substituted with 1 to 3 halogens).

In another embodiment the invention provides a compound structurally represented by formula I, or a pharmaceutically acceptable salt thereof, wherein
R⁰ is

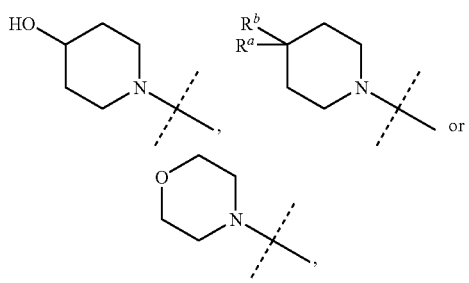

wherein the dashed line represents the point of attachment to the R⁰ position in formula I; wherein Rᵃ is -halogen; Rᵇ is —H or halogen;
R¹ is -chlorine, -fluorine, or -bromine; R² is chlorine, -fluorine, or -bromine; R³ is —H or -halogen;
R⁴ is

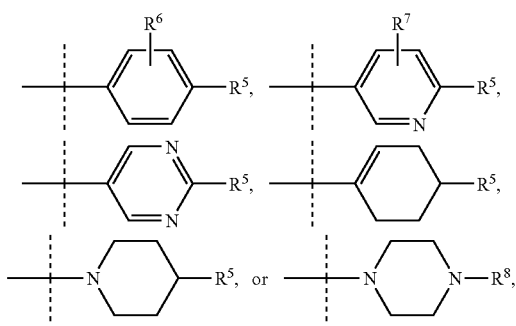

wherein the dashed line represents the point of attachment to the R⁴ position in formula I;
R⁵ is
—N(R⁸)(R⁸),

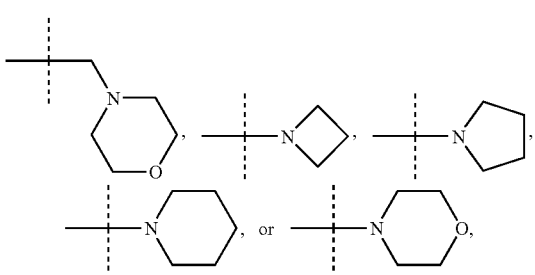

wherein the dashed line represents the point of attachment to the position indicated by R⁵;
R⁶ is
—H, -halogen, —CN, or —(C₁-C₄)alkyl(optionally substituted with 1 to 3 halogens);

R⁷ is
—H, -halogen, or —(C₁-C₄)alkyl(optionally substituted with 1 to 3 halogens); and R⁸ is independently at each occurrence
—H, —(C₁-C₆)alkyl(optionally substituted with 1 to 3 halogens),
—C(O)(C₁-C₆)alkyl(optionally substituted with 1 to 3 halogens),
—C(O)—(C₃-C₈)cycloalkyl, —S(O₂)—(C₃-C₈)cycloalkyl or
—S(O₂)—(C₁-C₃)alkyl(optionally substituted with 1 to 3 halogens).

Other embodiments of the invention are provided wherein each of the embodiments described herein above is further narrowed as described in the following preferences. Specifically, each of the preferences below is independently combined with each of the embodiments above, and the particular combination provides another embodiment in which the variable indicated in the preference is narrowed according to the preference.

Preferably R⁰ is

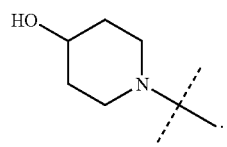

Preferably R⁰ is

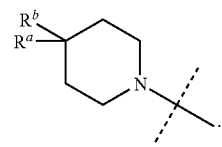

Preferably R⁰ is

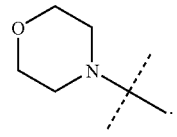

Preferably Rᵃ is -chlorine, fluorine, or -bromine. Preferably Rᵇ is -chlorine, fluorine, or -bromine. Preferably R¹ is -halogen. Preferably R¹ is —CH₃. Preferably R¹ is chlorine, -fluorine, or -bromine. Preferably R¹ is -chlorine. Preferably R¹ is -fluorine. Preferably R¹ is -bromine. Preferably R² is -halogen. Preferably R² is —CH₃. Preferably R² is -chlorine, -fluorine, or -bromine. Preferably R² is -chlorine. Preferably R² is -fluorine. Preferably R² is -bromine. Preferably R² is chlorine and R² is chlorine. Preferably R³ is —H. Preferably R³ is -halogen.

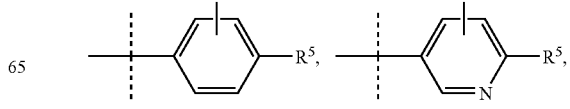

-continued
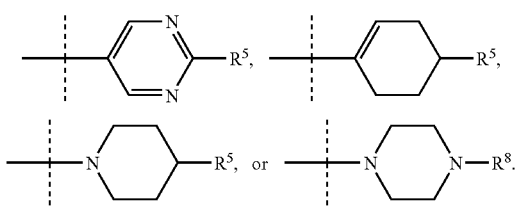
Preferably R⁴ is
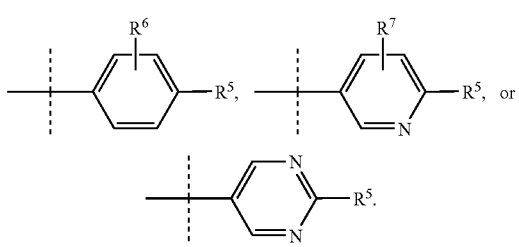
Preferably R⁴ is
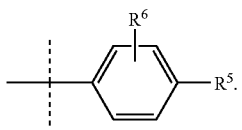
Preferably R⁴ is
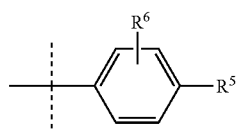
and R⁶ is hydrogen. Preferably R⁴ is
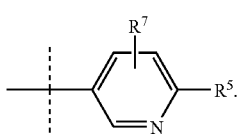
Preferably R⁴ is
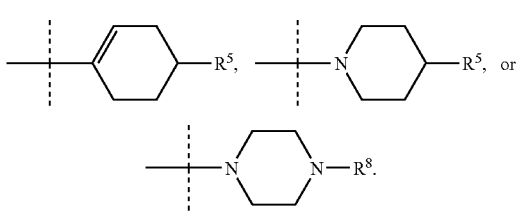
Preferably R⁴ is
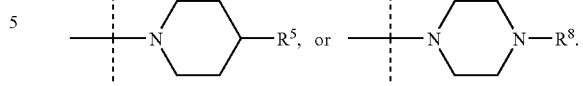
Preferably R⁴ is
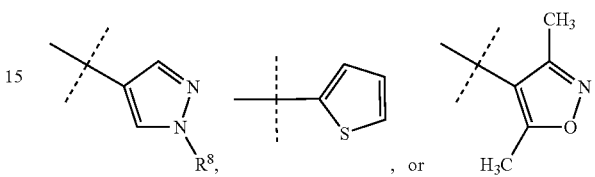
Preferably R⁴ is
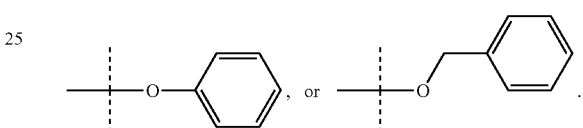
Preferably R⁴ is
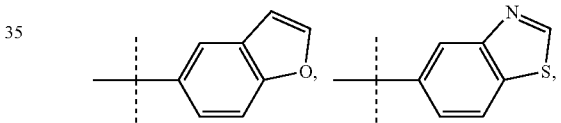
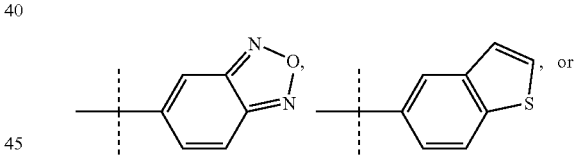
Preferably R⁴ is
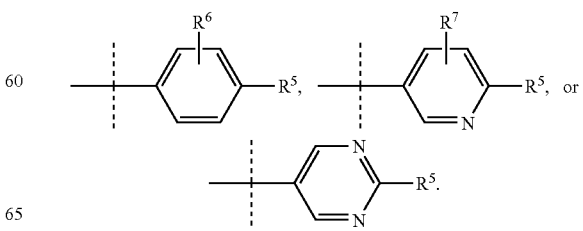

Preferably R⁵ is —N(R⁸)(R⁸),
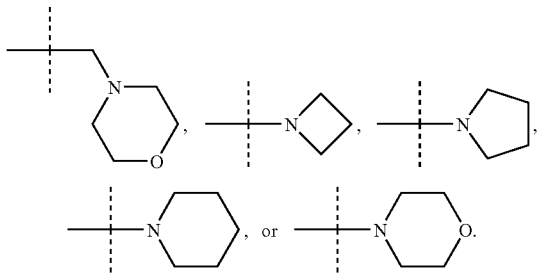
Preferably R⁵ is —SO₂—(C₁-C₄)alkyl,
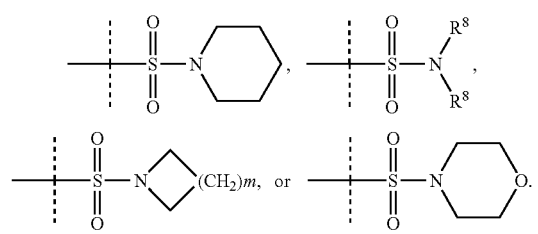
Preferably R⁵ is
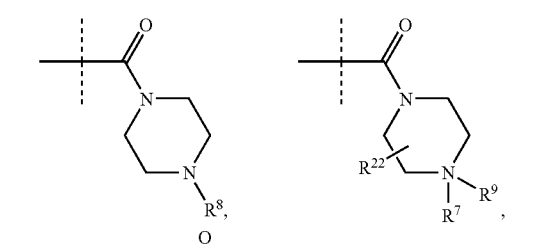
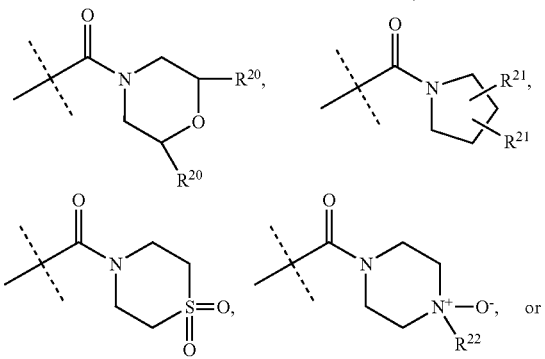
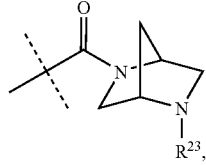
Preferably R⁵ is
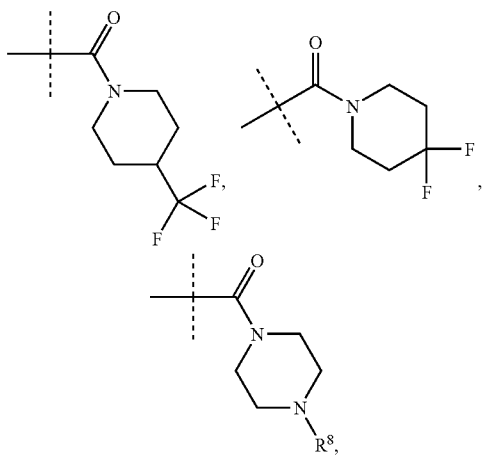
wherein R⁸ is —(C₁-C₃)alkyl (optionally substituted with 1 to 3 halogens), or
Preferably R⁵ is
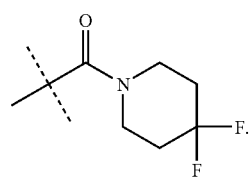
Preferably R⁵ is
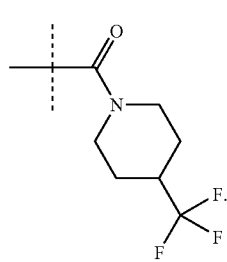

Preferably $R^6$ is —H. Preferably $R^6$ is -halogen. Preferably $R^6$ is —($C_1$-$C_4$)alkyl(optionally substituted with 1 to 3 halogens). Preferably $R^7$ is —H. Preferably $R^7$ is -halogen, or —($C_1$-$C_4$)alkyl(optionally substituted with 1 to 3 halogens). Preferably $R^7$ is -halogen. Preferably $R^7$ is —($C_1$-$C_4$)alkyl (optionally substituted with 1 to 3 halogens). Preferably $R^5$ is independently at each occurrence —H. Preferably $R^8$ is independently at each occurrence —($C_1$-$C_6$)alkyl(optionally substituted with 1 to 3 halogens). Preferably $R^5$ is independently at each occurrence —$CH_3$. Preferably $R^9$ is —H. Preferably $R^9$ is -halogen. Preferably $R^7$ is -fluorine and $R^9$ is -fluorine.

A preferred embodiment of the invention are compounds of the formula (R)-3-[3,5-Dichloro-4'-(4-trifluoromethyl-piperidine-1-carbonyl)-biphenyl-4-ylmethyl]-1-(4-hydroxy-piperidin-1-yl)-pyrrolidin-2-one, or pharmaceutically acceptable salts thereof. A preferred embodiment of the invention are compounds of the formula (R)-3-[3,5-Dichloro-4'-(4,4-difluoro-piperidine-1-carbonyl)-biphenyl-4-ylmethyl]-1-(4-hydroxy-piperidin-1-yl)-pyrrolidin-2-one, or pharmaceutically acceptable salts thereof. A further embodiment of the invention are the novel intermediate preparations described herein which are useful for preparing the 11-β-HSD1 inhibitors according to formula I and the embodiments described herein. A further embodiment of the invention are the novel intermediate preparations described herein which are useful for preparing (R)-3-[3,5-Dichloro-4'-(4-trifluoromethyl-piperidine-1-carbonyl)-biphenyl-4-ylmethyl]-1-(4-hydroxy-piperidin-1-yl)-pyrrolidin-2-one or a pharmaceutically acceptable salt thereof.

Patients with type 2 diabetes often develop "insulin resistance" which results in abnormal glucose homeostasis and hyperglycemia leading to increased morbidity and premature mortality. Abnormal glucose homeostasis is associated with obesity, hypertension, and alterations in lipid, lipoprotein, and apolipoprotein metabolism. Type 2 diabetics are at increased risk of developing cardiovascular complications, e.g., atherosclerosis, coronary heart disease, stroke, peripheral vascular disease, hypertension, nephropathy, neuropathy, and retinopathy. Therefore, therapeutic control of glucose homeostasis, lipid metabolism, obesity, and hypertension are important in the management and treatment of diabetes mellitus. Many patients who have insulin resistance but have not developed type 2 diabetes are also at risk of developing "Syndrome X" or "Metabolic syndrome". Metabolic syndrome is characterized by insulin resistance along with abdominal obesity, hyperinsulinemia, high blood pressure, low HDL, high VLDL, hypertension, atherosclerosis, coronary heart disease, and chronic renal failure. These patients are at increased risk of developing the cardiovascular complications listed above whether or not they develop overt diabetes mellitus.

Due to their inhibition of 11-β-HSD1, the present compounds are useful in the treatment of a wide range of conditions and disorders in which inhibition of 11-β-HSD1 is beneficial. These disorders and conditions are defined herein as "diabetic disorders" and "metabolic syndrome disorders". One of skill in the art is able to identify "diabetic disorders" and "metabolic syndrome disorders" by the involvement of 11-β-HSD1 activity either in the pathophysiology of the disorder, or in the homeostatic response to the disorder. Thus, the compounds may find use for example to prevent, treat, or alleviate, diseases or conditions or associated symptoms or sequelae, of "Diabetic disorders" and "metabolic syndrome disorders".

"Diabetic disorders" and "metabolic syndrome disorders" include, but are not limited to, diabetes, type 1 diabetes, type 2 diabetes, hyperglycemia, hyper insulinemia, beta-cell rest, improved beta-cell function by restoring first phase response, prandial hyperglycemia, preventing apoptosis, impaired fasting glucose (IFG), metabolic syndrome, hypoglycemia, hyper-/hypokalemia, normalizing glucagon levels, improved LDL/HDL ratio, reducing snacking, eating disorders, weight loss, polycystic ovarian syndrome (PCOS), obesity as a consequence of diabetes, latent autoimmune diabetes in adults (LADA), insulitis, islet transplantation, pediatric diabetes, gestational diabetes, diabetic late complications, micro-/macroalbuminuria, nephropathy, retinopathy, neuropathy, diabetic foot ulcers, reduced intestinal motility due to glucagon administration, short bowel syndrome, antidiarrheic, increasing gastric secretion, decreased blood flow, erectile dysfunction, glaucoma, post surgical stress, ameliorating organ tissue injury caused by reperfusion of blood flow after ischemia, ischemic heart damage, heart insufficiency, congestive heart failure, stroke, myocardial infarction, arrhythmia, premature death, anti-apoptosis, wound healing, impaired glucose tolerance (IGT), insulin resistance syndromes, metabolic syndrome, syndrome X, hyperlipidemia, dyslipidemia, hypertriglyceridemia, hyperlipoproteinemia, hypercholesterolemia, arteriosclerosis including atherosclerosis, glucagonomas, acute pancreatitis, cardiovascular diseases, hypertension, cardiac hypertrophy, gastrointestinal disorders, obesity, diabetes as a consequence of obesity, diabetic dyslipidemia, etc. Thus the present invention also provides a method of treatment of "Diabetic disorders" and "metabolic syndrome disorders" while reducing and or eliminating one or more of the unwanted side effects associated with the current treatments.

In addition, the present invention provides a compound of Formula I, or a pharmaceutical salt thereof, or a pharmaceutical composition which comprises a compound of Formula I, or a pharmaceutical salt thereof, and a pharmaceutically acceptable carrier, diluent, or excipient: for use in inhibiting 11-β-HSD1 activity; for use in inhibiting a 11-β-HSD1 activity mediated cellular response in a mammal; for use in reducing the glycemic level in a mammal; for use in treating a disease arising from excessive 11-β-HSD1 activity; for use in treating diabetic and other metabolic syndrome disorders in a mammal; and for use in treating diabetes, metabolic syndrome, obesity, hyperglycemia, atherosclerosis, ischemic heart disease, stroke, neuropathy, and wound healing. Thus, the methods of this invention encompass a prophylactic and therapeutic administration of a compound of Formula I.

The present invention further provides the use of a compound of Formula I, or a pharmaceutical salt thereof for the manufacture of a medicament for inhibiting 11-β-HSD1 activity; for the manufacture of a medicament for inhibiting 11-β-HSD1 activity mediated cellular response in a mammal; for the manufacture of a medicament for reducing the glycemic level in a mammal; for the manufacture of a medicament for treating a disease arising from excessive 11-β-HSD1 activity; for the manufacture of a medicament for treating diabetic and other metabolic syndrome disorders in a mammal; and for the manufacture of a medicament for preventing or treating diabetes, metabolic syndrome, obesity, hyperglycemia, atherosclerosis, ischemic heart disease, stroke, neuropathy, and improper wound healing.

The present invention further provides a method of treating conditions resulting from excessive 11-β-HSD1 activity in a mammal; a method of inhibiting 11-β-HSD1 activity in a mammal; a method of inhibiting a 11-β-HSD1 activity mediated cellular response in a mammal; a method of reducing the glycemic level in a mammal; a method of treating diabetic and other metabolic syndrome disorders in a mammal; a method of preventing or treating diabetes, metabolic syndrome, obesity, hyperglycemia, atherosclerosis, ischemic heart disease, stroke, neuropathy, and improper wound healing; said methods comprising administering to a mammal in need of such treatment a 11-β-HSD1 activity inhibiting amount of a compound of Formula I, or a pharmaceutically acceptable salt thereof, or a pharmaceutical composition which comprises a compound of Formula I, or a pharmaceutical salt thereof, and a pharmaceutically acceptable carrier, diluent, or excipient.

In addition, the present invention provides a pharmaceutical composition which comprises a compound of Formula I, or a pharmaceutical salt thereof, and a pharmaceutically acceptable carrier, diluent, or excipient: adapted for use in inhibiting 11-β-HSD1 activity; adapted for use in inhibiting 11-β-HSD1 activity mediated cellular responses; adapted for use in reducing the glycemic level in a mammal; adapted for use in treating diabetic and other metabolic syndrome disorders in a mammal; and adapted for use in preventing or treating diabetes, metabolic syndrome, obesity, hyperglycemia, atherosclerosis, ischemic heart disease, stroke, neuropathy, and wound healing.

In a further aspect of the invention the present compounds are administered in combination with one or more further active substances in any suitable ratios. Such further active substances may for example be selected from antidiabetics, antiobesity agents, antihypertensive agents, agents for the treatment of complications resulting from or associated with diabetes and agents for the treatment of complications and disorders resulting from or associated with obesity. The following listing sets out several groups of combinations. It will be understood that each of the agents named may be combined with other agents named to create additional combinations.

Thus, in a further embodiment of the invention the present compounds may be administered in combination with one or more antidiabetics.

Suitable antidiabetic agents include insulin, insulin analogues and derivatives such as those disclosed in EP 792 290 (Novo Nordisk A/S), for example $N^{\epsilon B29}$-tetradecanoyl des (B30) human insulin, EP 214 826 and EP 705 275 (Novo Nordisk A/S), for example $ASP^{B28}$ human insulin, U.S. Pat. No. 5,504,188 (Eli Lilly), for example $Lys^{B28}$ $Pro^{B29}$ human insulin, EP 368 187 (Aventis), for example Lantus®, GLP-1 and GLP-1 derivatives such as those disclosed in WO 98/08871 (Novo Nordisk A/S), as well as orally active hypoglycemic agents.

The orally active hypoglycemic agents preferably comprise imidazolines, sulphonylureas, biguanides, meglitinides, oxadiazolidinediones, thiazolidinediones, insulin sensitizers, insulin secretagogues, such as glimepiride, α-glucosidase inhibitors, agents acting on the ATP-dependent potassium channel of the β-cells for example potassium channel openers such as those disclosed in WO 97/26265, WO 99/03861 and WO 00/37474 (Novo Nordisk A/S), or mitiglinide, or a potassium channel blocker, such as BTS-67582, nateglinide, glucagon antagonists such as those disclosed in WO 99/01423 and WO 00/39088 (Novo Nordisk A/S and Agouron Pharmaceuticals, Inc.), GLP-1 antagonists, DPP-IV (dipeptidyl peptidase-IV) inhibitors, PTPase (protein tyrosine phosphatase) inhibitors, inhibitors of hepatic enzymes involved in stimulation of gluconeogenesis and/or glycogenolysis, glucose uptake modulators, activators of glucokinase (GK) such as those disclosed in WO 00/58293, WO 01/44216, WO 01/83465, WO 01/83478, WO 01/85706, WO 01/85707, and WO 02/08209 (Hoffman-La Roche) or those disclosed in WO 03/00262, WO 03/00267 and WO 03/15774 (AstraZeneca), GSK-3 (glycogen synthase kinase-3) inhibitors, compounds modifying the lipid metabolism such as antilipidemic agents such as HMG CoA inhibitors (statins), compounds lowering food intake, PPAR (Peroxisome proliferator-activated receptor) ligands including the PPAR-alpha, PPAR-gamma and PPAR-delta subtypes, and RxR (retinoid X receptor) agonists, such as ALRT-268, LG-1268 or LG-1069.

In another embodiment, the present compounds are administered in combination with insulin or an insulin analogue or derivative, such as $N^{\epsilon B29}$-tetradecanoyl des (B30) human insulin, $ASP^{B28}$ human insulin, $Lys^{B28}$ $Pro^{B29}$ human insulin, Lantus®, or a mix-preparation comprising one or more of these.

In a further embodiment of the invention the present compounds are administered in combination with a sulphonylurea such as glibenclamide, glipizide, tolbautamide, chloropamidem, tolazamide, glimepride, glicazide and glyburide.

In another embodiment of the invention the present compounds are administered in combination with a biguanide, for example, metformin.

In yet another embodiment of the invention the present compounds are administered in combination with a meglitinide, for example, repaglinide or nateglinide.

In still another embodiment of the invention the present compounds are administered in combination with a thiazolidinedione insulin sensitizer, for example, troglitazone, ciglitazone, pioglitazone, rosiglitazone, isaglitazone, darglitazone, englitazone, CS-011/CI-1037 or T 174 or the compounds disclosed in WO 97/41097, WO 97/41119, WO 97/41120, WO 00/41121 and WO 98/45292 (Dr. Reddy's Research Foundation).

In still another embodiment of the invention the present compounds may be administered in combination with an insulin sensitizer, for example, such as GI 262570, YM-440, MCC-555, JTT-501, AR-H039242, KRP-297, GW-409544, CRE-16336, AR-H049020, LY510929, MBX-102, CLX-0940, GW-501516 or the compounds disclosed in WO 99/19313, WO 00/50414, WO 00/63191, WO 00/63192, WO 00/63193 such as ragaglitazar (NN 622 or (−)DRF 2725) (Dr. Reddy's Research Foundation) and WO 00/23425, WO 00/23415, WO 00/23451, WO 00/23445, WO 00/23417, WO 00/23416, WO 00/63153, WO 63196, WO 00/63209, WO 00/63190 and WO 00/63189 (Novo Nordisk A/S).

In a further embodiment of the invention the present compounds are administered in combination with an α-glucosidase inhibitor, for example, voglibose, emiglitate, miglitol or acarbose.

In another embodiment of the invention the present compounds are administered in combination with an agent acting on the ATP-dependent potassium channel of the β-cells, for example, tolbutamide, glibenclamide, glipizide, glicazide, BTS-67582 or repaglinide.

In yet another embodiment of the invention the present compounds may be administered in combination with nateglinide.

In still another embodiment of the invention the present compounds are administered in combination with an antilipidemic agent or antihyperlipidemic agent for example cholestyramine, colestipol, clofibrate, gemfibrozil, lovastatin, pravastatin, simvastatin, pitavastatin, rosuvastatin, probucol, dextrothyroxine, fenofibrate or atorvastin.

In still another embodiment of the invention the present compounds are administered in combination with compounds lowering food intake.

In another embodiment of the invention, the present compounds are administered in combination with more than one of the above-mentioned compounds for example in combination with metformin and a sulphonylurea such as glyburide; a sulphonylurea and acarbose; nateglinide and metformin; repaglinide and metformin, acarbose and metformin; a sulfonylurea, metformin and troglitazone; insulin and a sulfonylurea; insulin and metformin; insulin, metformin and a sulfonylurea; insulin and troglitazone; insulin and lovastatin; etc.

General terms used in the description of compounds herein described bear their usual meanings.

As used herein, the terms "$(C_1-C_3)$alkyl", "$(C_1-C_4)$alkyl" or "$(C_1-C_6)$alkyl" refer to straight-chain or branched-chain saturated aliphatic groups of the indicated number of carbon atoms, such as methyl, ethyl, n-propyl, isopropyl, n-butyl, isobutyl, sec-butyl, t-butyl, and the like. The term "$(C_1-C_6)$ alkoxy" represents a $C_1-C_6$ alkyl group attached through an oxygen and include moieties such as, for example, methoxy, ethoxy, n-propoxy, isopropoxy, and the like. The term "halogen" refers to fluoro, chloro, bromo, and iodo. The term "$(C_3-C_8)$ cycloalkyl" refers to a saturated or partially saturated carbocycle ring of from 3 to 8 carbon atoms, typically 3 to 7 carbon atoms. Examples of $(C_3-C_8)$ cycloalkyl include but are not limited to cyclopropyl, cyclobutyl, cyclopentyl, cyclohexyl, cycloheptyl, and the like.

The term "optionally substituted," or "optional substituents," as used herein, means that the groups in question are either unsubstituted or substituted with one or more of the substituents specified. When the groups in question are substituted with more than one substituent, the substituents may be the same or different. Furthermore, when using the terms "independently," "independently are," and "independently selected from" mean that the groups in question may be the same or different. Certain of the herein defined terms may occur more than once in the structural formulae, and upon such occurrence each term shall be defined independently of the other.

It is understood that guinea pigs, dogs, cats, rats, mice, hamsters, and primates, including humans, are examples of patients within the scope of the meaning of the term "patient". The term "patient" includes livestock animals. Livestock animals are animals raised for food production. Ruminants or "cud-chewing" animals such as cows, bulls, heifers, steers, sheep, buffalo, bison, goats and antelopes are examples of livestock. Other examples of livestock include pigs and avians (poultry) such as chickens, ducks, turkeys and geese. The patient to be treated is preferably a mammal, in particular a human being.

The terms "treatment", "treating" and "treat", as used herein, include their generally accepted meanings, i.e., the management and care of a patient for the purpose of preventing, reducing the risk in incurring or developing a given condition or disease, prohibiting, restraining, alleviating, ameliorating, slowing, stopping, delaying, or reversing the progression or severity, and holding in check and/or treating existing characteristics, of a disease, disorder, or pathological condition, described herein, including the alleviation or relief of symptoms or complications, or the cure or elimination of the disease, disorder, or condition. The present method includes both medical therapeutic and/or prophylactic treatment, as appropriate.

As used herein, the term "therapeutically effective amount" means an amount of compound of the present invention that is capable of alleviating the symptoms of the various pathological conditions herein described. The specific dose of a compound administered according to this invention will, of course, be determined by the particular circumstances surrounding the case including, for example, the compound administered, the route of administration, the state of being of the patient, and the pathological condition being treated.

"Composition" means a pharmaceutical composition and is intended to encompass a pharmaceutical product comprising the active ingredient(s) including compound(s) of Formula I, and the inert ingredient(s) that make up the carrier. Accordingly, the pharmaceutical compositions of the present invention encompass any composition made by admixing a compound of the present invention and a pharmaceutically acceptable carrier.

The term "substantially pure" refers to pure crystalline form of a compound comprising greater than about 90% of the desired crystalline form, and preferably, greater than about 95% of the desired crystal form.

The term "suitable solvent" refers to any solvent, or mixture of solvents, inert to the ongoing reaction that sufficiently solubilizes the reactants to afford a medium within which to effect the desired reaction.

The term "unit dosage form" means physically discrete units suitable as unitary dosages for human subjects and other non-human animals, each unit containing a predetermined quantity of active material calculated to produce the desired therapeutic effect, in association with a suitable pharmaceutical carrier.

The compounds of the present invention may have one or more chiral centers and may exist in a variety of stereoisomeric configurations. As a consequence of these chiral centers the compounds of the present invention can occur as racemates, as individual enantiomers or mixtures of enantiomers, as well as diastereomers and mixtures of diastereomers. All such racemates, enantiomers, diastereomers and mixtures are within the scope of the present invention, whether pure, partially purified, or unpurified mixtures. For the examples provided herein, when a molecule which contains a chiral center or centers of known configuration is presented, its stereochemistry is designated in the name and in the structural representation of the molecule. If the stereochemistry is unknown or undefined its stereochemistry is not designated in the name or in the structural representation of the molecule. Embodiments of the invention include the Examples provided herein, and although the Example provided may be of one chiral or conformational form, or a salt thereof, further embodiments of the invention include all other steroisomeric and or conformational forms of the examples described, as well as pharmaceutically acceptable salts thereof. These embodiments include any isolated enantiomers, diastereomers, and or conformers of these structures, as well as any mixtures containing more than one form.

Furthermore, when a double bond or a fully or partially saturated ring system or more than one center of asymmetry or a bond with restricted rotatability is present in the molecule diastereomers may be formed. It is intended that any diastereomers, as separated, pure or partially purified diastereomers or mixtures thereof are included within the scope of the invention. Furthermore, some of the compounds of the present invention may exist in different tautomeric forms and it is intended that any tautomeric forms which the compounds are able to form are included within the scope of the present invention.

The term "enantiomeric enrichment" as used herein refers to the increase in the amount of one enantiomer as compared to the other. A convenient method of expressing the enantiomeric enrichment achieved is the concept of enantiomeric excess, or "ee", which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 70:30 is achieved, the ee with respect to the first enantiomer is 40%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the specific stereoisomers and enantiomers of compounds of formula I can be prepared by one of ordinary skill in the art utilizing well known techniques and processes, such as those disclosed by J. Jacques, et al., "*Enantiomers, Racemates, and Resolutions*", John Wiley and Sons, Inc., 1981, and E. L. Eliel and S. H. Wilen, "*Stereochemistry of Organic Compounds*", (Wiley-Interscience 1994), and European Patent Application No. EP-A-838448, published Apr. 29, 1998. Examples of resolutions include recrystallization techniques or chiral chromatography.

The compounds of Formula I, can be prepared by one of ordinary skill in the art following a variety of procedures, some of which are illustrated in the procedures and schemes set forth below. The particular order of steps required to produce the compounds of Formula I is dependent upon the particular compound to being synthesized, the starting compound, and the relative liability of the substituted moieties. The reagents or starting materials are readily available to one of skill in the art, and to the extent not commercially available, are readily synthesized by one of ordinary skill in the art following standard procedures commonly employed in the art, along with the various procedures and schemes set forth below.

The following Schemes, Preparations, Examples and Procedures are provided to better elucidate the practice of the present invention and should not be interpreted in any way as to limit the scope of the same. Those skilled in the art will recognize that various modifications may be made while not departing from the spirit and scope of the invention. All publications mentioned in the specification are indicative of the level of those skilled in the art to which this invention pertains.

The optimal time for performing the reactions of the Schemes, Preparations, Examples and Procedures can be determined by monitoring the progress of the reaction via conventional chromatographic techniques. Furthermore, it is preferred to conduct the reactions of the invention under an inert atmosphere, such as, for example, argon, nitrogen. Choice of solvent is generally not critical so long as the solvent employed is inert to the ongoing reaction and sufficiently solubilizes the reactants to effect the desired reaction. The compounds are preferably isolated and purified before their use in subsequent reactions. Some compounds may crystallize out of the reaction solution during their formation and then collected by filtration, or the reaction solvent may be removed by extraction, evaporation, or decantation. The intermediates and final products of Formula I may be further purified, if desired by common techniques such as recrystallization or chromatography over solid supports such as silica gel or alumina.

The skilled artisan will appreciate that not all substituents are compatible with all reaction conditions. These compounds may be protected or modified at a convenient point in the synthesis by methods well known in the art.

The terms and abbreviations used in the instant Schemes, Preparations, Examples and Procedures have their normal meanings unless otherwise designated. For example, as used herein, the following terms have the meanings indicated: "psi" refers to pounds per square inch; "TLC" refers to thin layer chromatography; "HPLC" refers to high performance liquid chromatography; "$R_f$" refers to retention factor; "$R_t$" refers to retention time; "δ" refers to part per million downfield from tetramethylsilane; "MS" refers to mass spectrometry, Observed Mass indicates [M+H] unless indicated otherwise. "MS (APCi) refers to atmospheric pressure chemical ionization mass spectrometry, "UV" refers to ultraviolet spectrometry, "$^1$H NMR" refers to proton nuclear magnetic resonance spectrometry. "LCMS" refers to liquid chromatography-mass spectrometry, "GC/MS" refers to gas chromatography/mass spectrometry. "IR" refers to infra red spectrometry, and the absorption maxima listed for the IR spectra are only those of interest and not all of the maxima observed. "RT" refers to room temperature.

"THF" refers to tetrahydrofuran, "LAH" refers to lithium aluminum hydride, "LDA" refers to lithium diisopropylamide, "DMSO" refers to dimethylsulfoxide, "DMF" refers to dimethylforamide, "EtOAc" refers to ethyl acetate, "Pd—C" refers to palladium on carbon, "DCM" refers to dichloromethane, "DMAP" refers to dimethylaminopyridine, "LiHMDS" refers to Lithium Hexamethyldisilisane, "TFA" refers to trifluoroacetic acid, "EDAC" refers to N-Ethyl-N]-(3-dimethylaminopropyl)carbodiimide hydrochloride, "HOBT" refers to 1-Hydroxy benzotriazole, "Bn-9-BBN" refers to Benzyl-9-borabicyclo[3.3.1]nonane, "Pd(dppf)Cl$_2$" refers to [1,1'-Bis(diphenylphosphino)-ferrocene)dichloropalladium(II), "EDCI" refers to N-Ethyl-N'-(3-dimethylaminopropyl)carbodiimide hydrochloride, "DBU" refers to 1,8-Diazabicyclo[5.4.0]undecene-7, "TBSCl" refers to tert-butyl-dimethyl-silanyloxymethyl chloride, "NBS" refers to N-Bromosuccinimide, "TsOH" refers to p-toluenesulfonic acid, "DCE" refers to dichloroethane, "DAST" refers to (Diethylamino)sulfur trifluoride, "EA/H" refers to ethyl acetate/hexanes mixture, "Pd$_2$(dba)$_3$" refers to Bis(dibenzylideneacetone)palladium, "BINAP" refers to 2,2'-Bis(diphenylphospino-1,1'-binaphthalene, "NMP" refers to N-Methylpyrrollidine, "TMSCN" refers to Trimethylsilyl cyanide, "TBAF" refers to Tetrabutylammonium fluoride, "Tf$_2$O" refers to trifluoromethanesulfonic anhydride, "TBSO" refers to tert-butyl-dimethyl-silanyloxy, "OTf" refers to trifluoromethanesulfonate, MeTi(Oi-Pr)$_3$ refers to methyltitanium triisopropoxide, "BBr$_3$" refers to boron tribromide, "PBr$_3$" refers to phosphorous tribromide, "Pd(PPh$_3$)$_4$" refers to tetrakis(triphenylphoshine)palladium (0), "OAc" refers to acetate, "DME" refers to dimethylethane, "Et$_2$O" refers to diethyl ether, "(Ph$_3$P)$_4$Pd" refers to tetrakis (triphenylphoshine)palladium (0), "DMFDMA" refers to N,N-dimethylformamide dimethyl acetal, "Et$_3$N" refers to triethylamine, "tBu" refers to t-butyl, "DIPEA" refers to diisopropylethyl amine, "EDC" refers to -(3-Dimethylaminopropyl)-3-ethylcarbodiimide hydrochloride, "HOAc" refers to acetic acid, "boc" refers to t-butoxycarbonyl. In a structure, "Ph" refers to phenyl, "Me" refers to methyl, "Et" refers to ethyl, "Bn" refers to benzyl, "MeOH" refers to methanol, "OTf" refers to trifluoromethanesulfonate, "TIPSO" refers to triisopropylsilanyloxy, "TBSO" refers to tert-butyl-dimethyl-silanyloxy, "NaBH(OAc)$_3$" refers to sodium triacetoxyborohydride, "[Ir(cod)Cl]₂" refers to Di-chlorobis((1,2,5,6-eta)-1,5-cyclooctadiene)diiridium.

The Examples provided herein are illustrative of the invention claimed herein and are not intended to limit the scope of the claimed invention in any way. The preparations and examples are named using AutoNom 2.2 in ChemDraw Ultra, or AutoNom 2000 in MDL ISIS/Draw version 2.5 SPI from MDL Information Systems, Inc., or are provided by Chemical Abstracts Services.

A Varian INOVA 400 MHz spectrometer is used to obtain ¹H NMR Specta the in the solvent indicated. An Agilent HP1100 instrument equipped with a Mass Spectrometer (Agilent MSD SL) is used to obtain LCMS. A Waters Xterra C18 (2.1×50 mm, 3.5 micron) is used as stationary phase and a standard method is a gradient of 5-100% acetonitrile/methanol (50:50) with 0.2% ammonium formate over 3.5 minutes then held at 100% B for 0.5 minutes at a column temperature of 50° C. and a flow rate of 1.0 mL/min. Another standard method is a gradient of 5-100% acetonitrile/methanol (50:50) with 0.2% ammonium formate over 7.0 minutes then held at 100% B for 1.0 minutes at a column temperature of 50° C. and a flow rate of 1.0 mL/min. Additional MS analysis via Agilent MSD (loop machine) is standard Flow injection Analysis (FIA), no column is present and flow is 0.5 ml/min of 80% MeOH with 6.5 mM Ammonium Acetate for 30 secs run time.

Scheme A

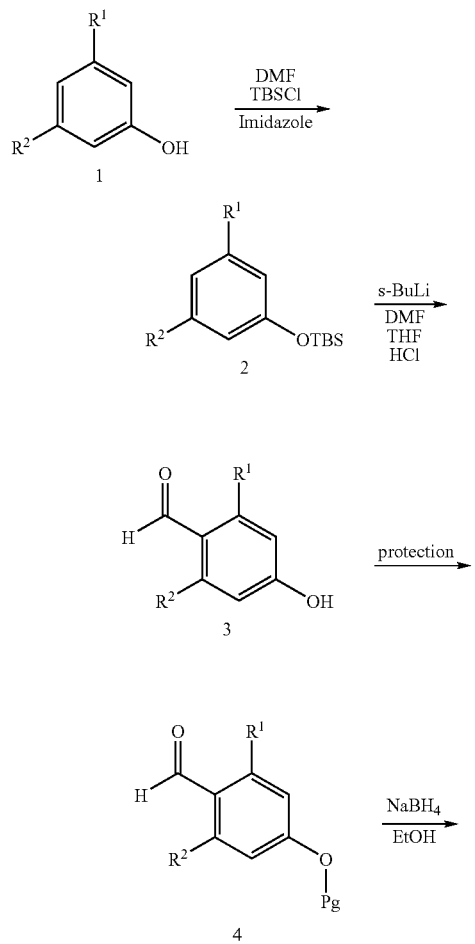

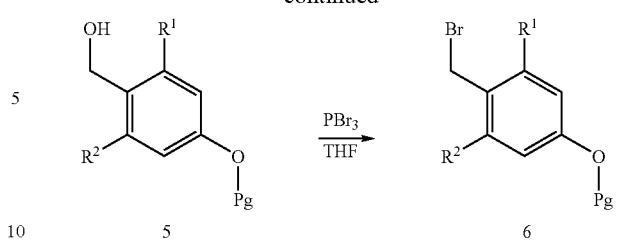

In Scheme A, an optionally substituted phenol (1) is protected (e.g, with TBSCl) to form compound 2, and then compound 2 is converted to the aldehyde (3). Compound 3 is reacted with a compound containing a protecting group (Pg) and leaving group (Lg) to give the ether compound 4. Pg can be —CH₃ or —CH₂-phenyl and Lg can be mesylate or halo. Preferably, the Lg-Pg compound is I—CH₃ or Br—CH₂-phenyl. The aldehyde is reduced to form the alcohol (5) and then converted to compound 6. Preferably, compound 5 is halogenated with PBr₃ to give the 2-bromo-methyl compound.

Protection and deprotection of the compounds to form compounds of formula I and others are well known to the skilled artisan and are described in the literature. (For example, see: Greene and Wuts, *Protective Groups in Organic Synthesis*, Third Edition, John Wiley and Sons Inc., 1999).

Scheme B

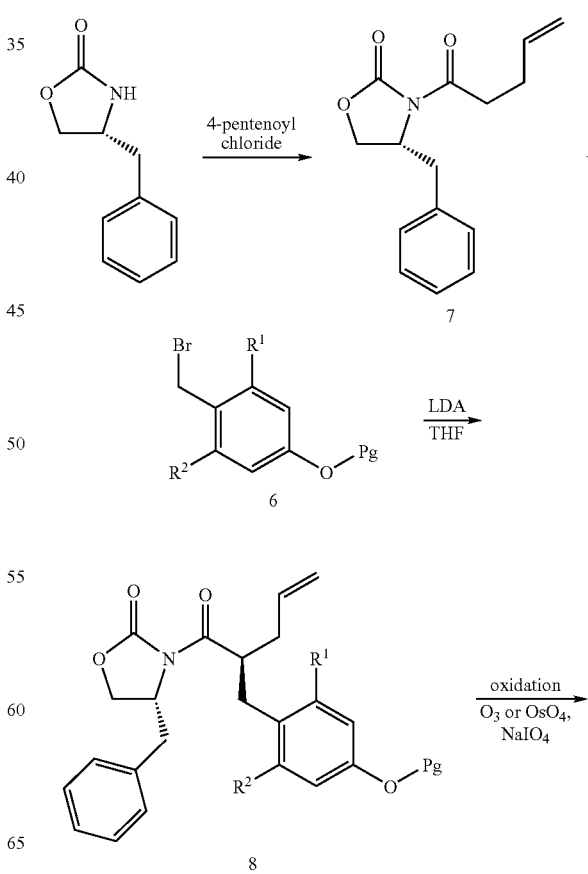

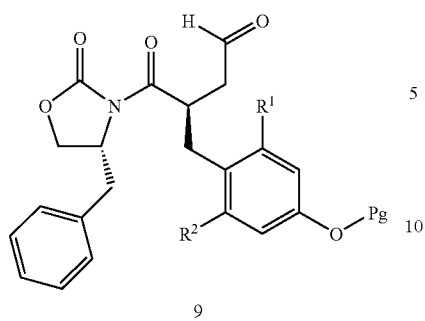

9

Scheme B shows the stereo selective synthesis to form the intermediate compound 9. Compound 7 is formed by acylating commercially available (R)-4-benzyl-oxazolidin-2-one with 4-pentenoyl chloride. It is then alkylated with an optionally substituted compound 6 (see Scheme A) to give compound of 8. Compound 8 is oxidized to form the aldehyde intermediate compound 9 using ozone and triphenylphosphine or osmium tetroxide and an oxidant such as sodium metaperiodate.

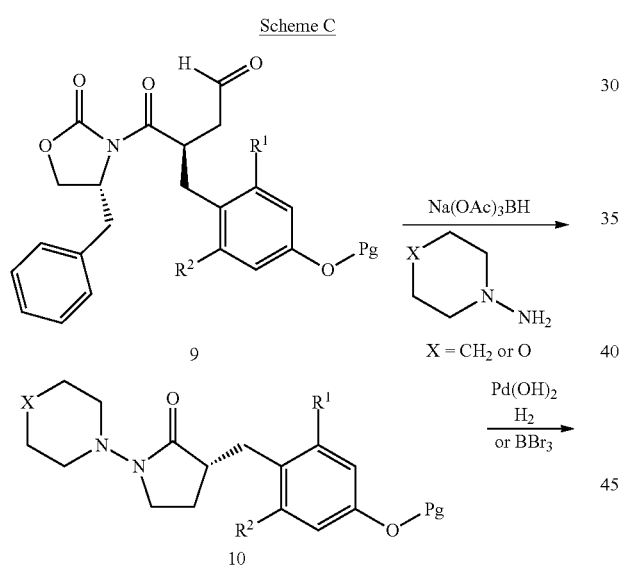

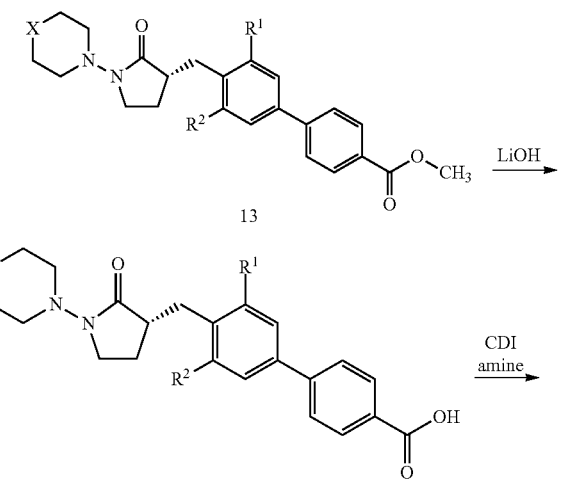

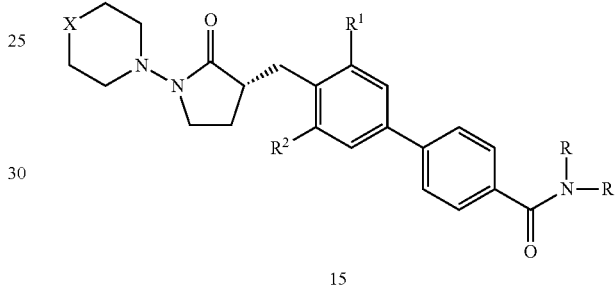

In Scheme C, treatment of the aldehyde 9 with the amine yields the hydrazide 10. Compound 10 is deprotected to form the phenol compound 11, and then the triflate compound 12 is formed upon treatment with trifluoromethanesulfonic anhydride and a base such as pyridine. A coupling reaction is performed on (12) using a phenylboronic acid reagent and a catalyst, such as palladium tetrakistriphenylphosphine to prepare an ester (13) that is hydrolyzed to afford acid (14). Acid (14) is coupled with an amine using standard amide coupling conditions such as 1,1'-carbonyldiimidazole to afford amide (15).

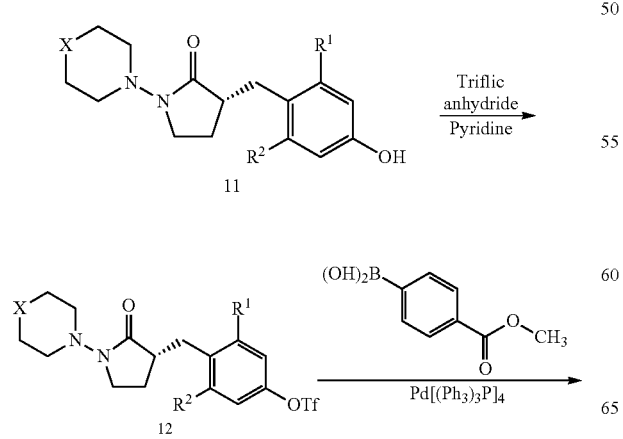

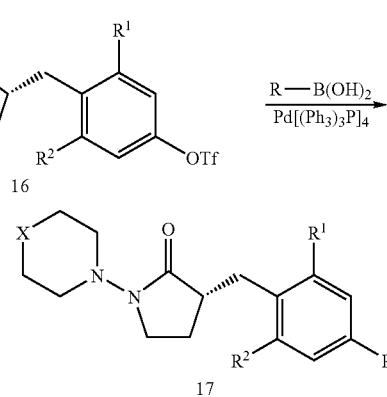

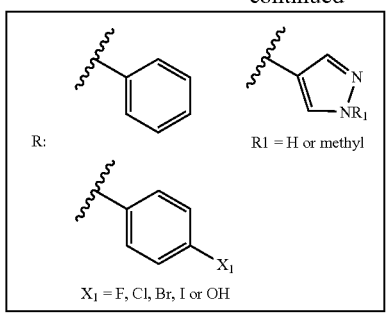

In Scheme D, a coupling reaction is performed on (16) using a phenylboronic acid reagent and a catalyst, such as palladium tetrakistriphenylphosphine to prepare the compound 17.

In Scheme E, a coupling reaction is performed on (16) using a phenylboronic acid reagent and a catalyst, such as palladium tetrakistriphenylphosphine to prepare the compound 19. The amide (20), benzoisoxazole (21), and indazole (22) are formed from compound 19 using the reagents as described.

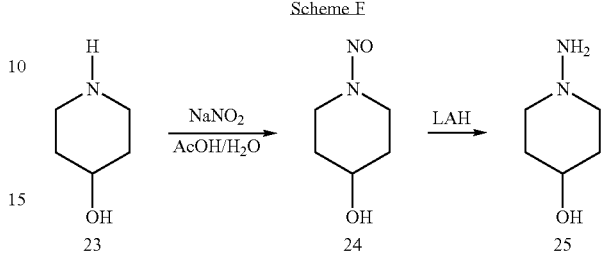

Scheme E

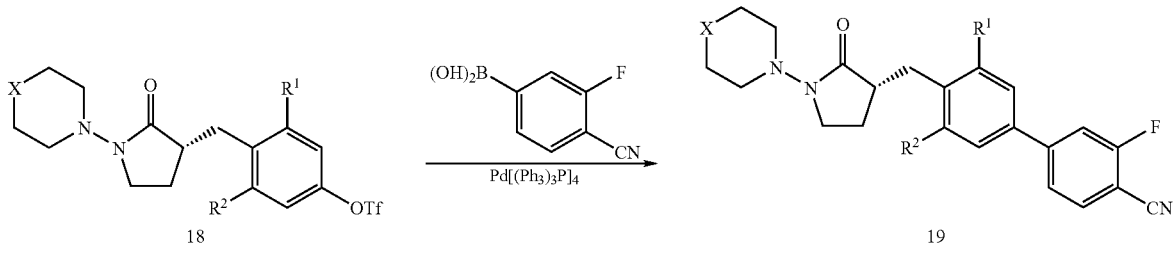

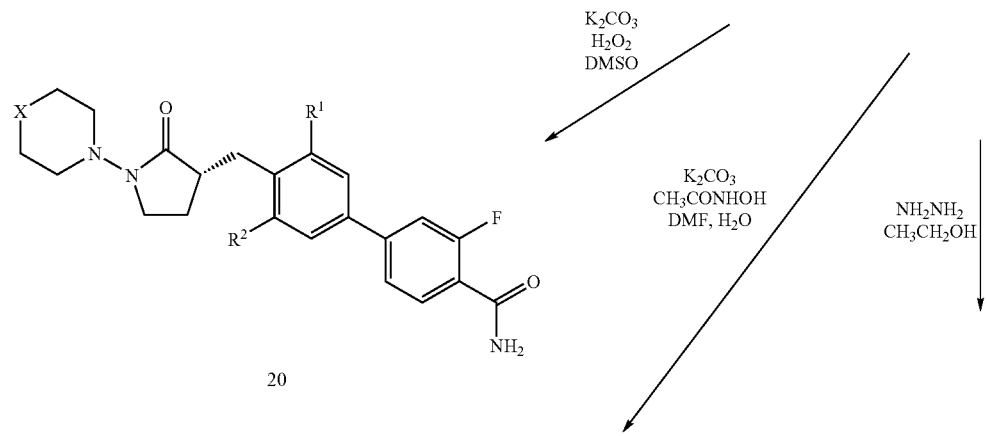

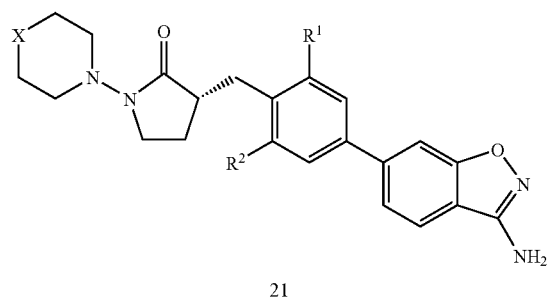

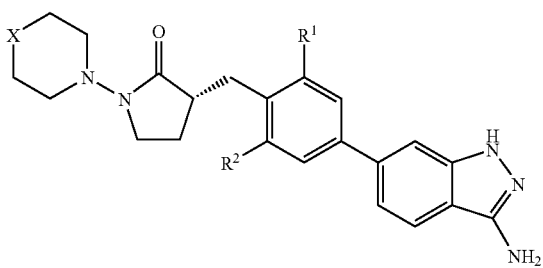

Scheme G
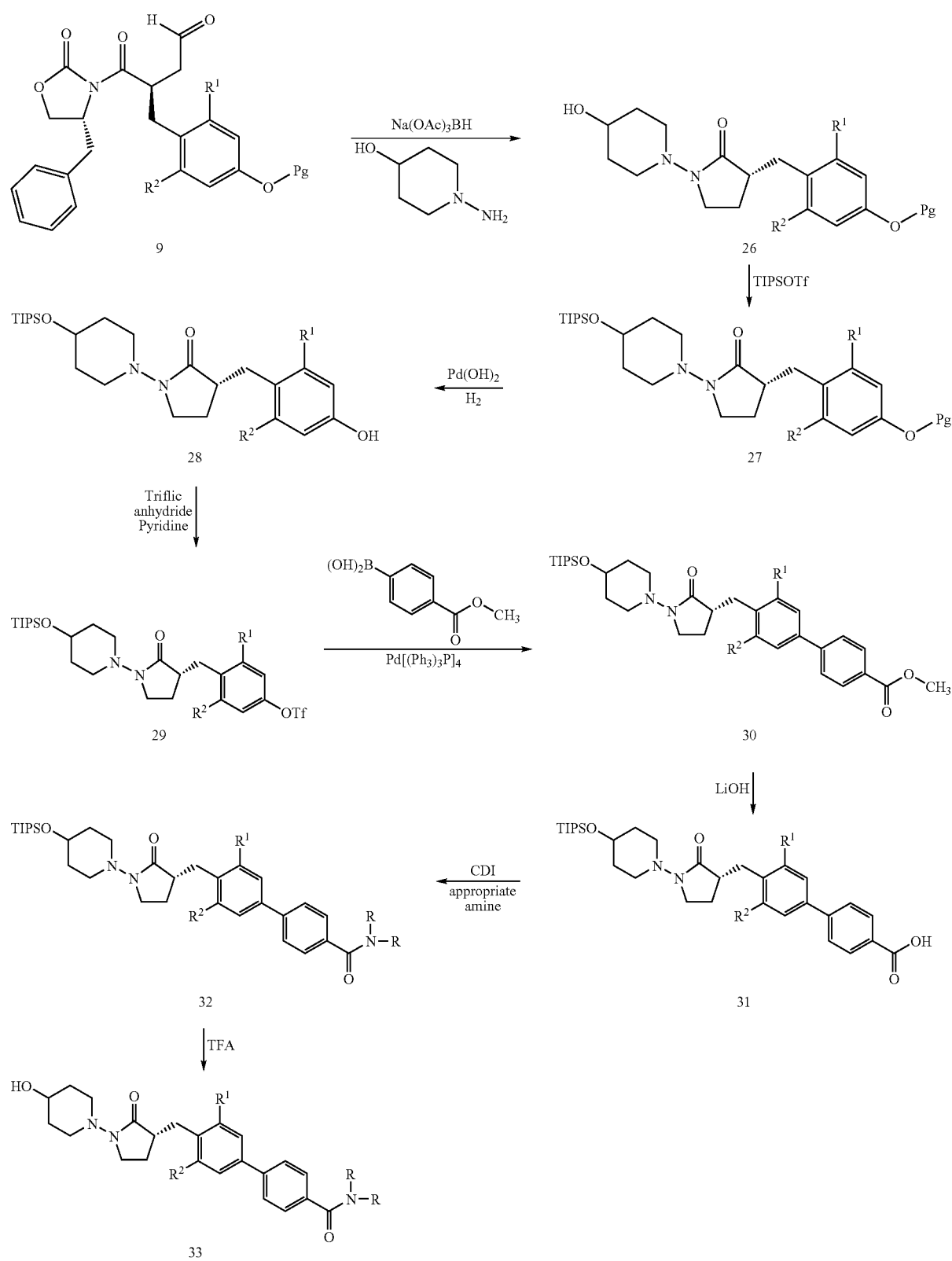
In Scheme G, treatment of the aldehyde 9 with the amine yields the hydrazide 26 and then treated with triisopropylsi-lyltrifluoromethane sulfonate to yield the compound 27. Compound 27 is deprotected using palladium on carbon to yield the phenol (28) which is then treated with triflic anhydride to yield the compound 29. A coupling reaction is performed on (29) using a phenylboronic acid reagent and a catalyst, such as palladium tetrakistriphenylphosphine to prepare an ester (30) that is hydrolyzed to afford acid (31). Acid (31) is coupled with an amine using standard amide coupling conditions such as 1,1'-carbonyldiimidazole to afford the amide (32). The amide (32) is then treated with an acid such as trifluoroacetic acid to yield the amide (33).

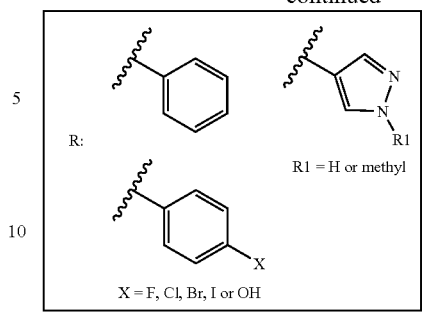

In Scheme H, a coupling reaction is performed on (34) using a phenylboronic acid reagent (R—B(OH)$_2$) and a catalyst, such as palladium tetrakistriphenylphosphine to prepare the compound 35 which is treated with trifluoroacetic acid to form compound 36.

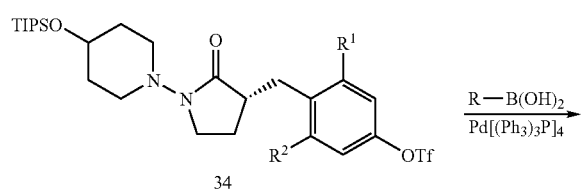

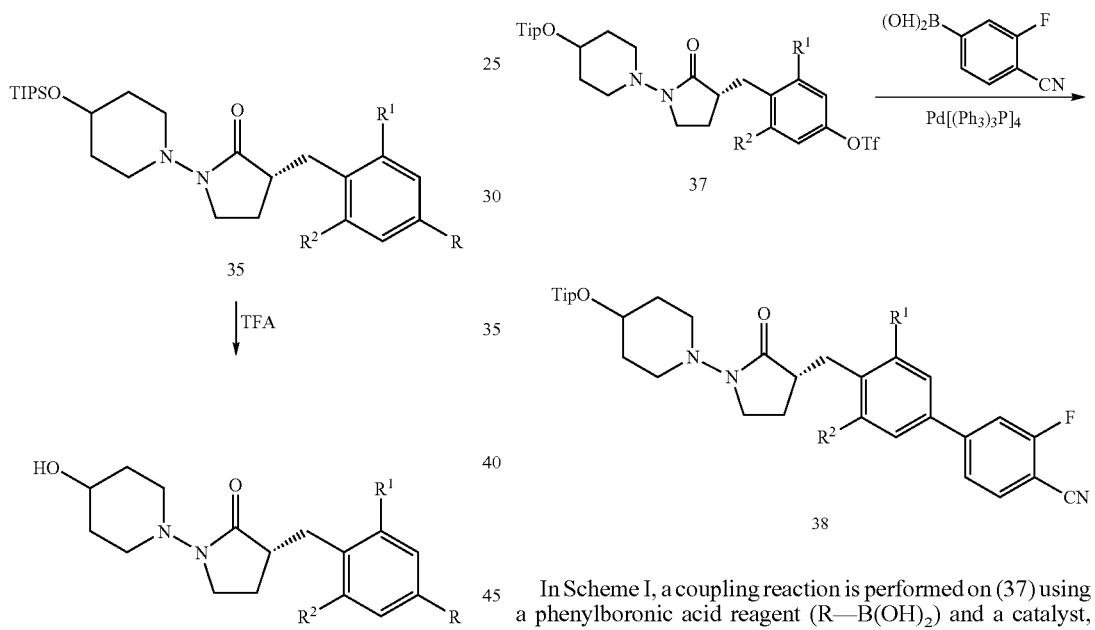

In Scheme I, a coupling reaction is performed on (37) using a phenylboronic acid reagent (R—B(OH)$_2$) and a catalyst, such as palladium tetrakistriphenylphosphine to prepare the compound 38.

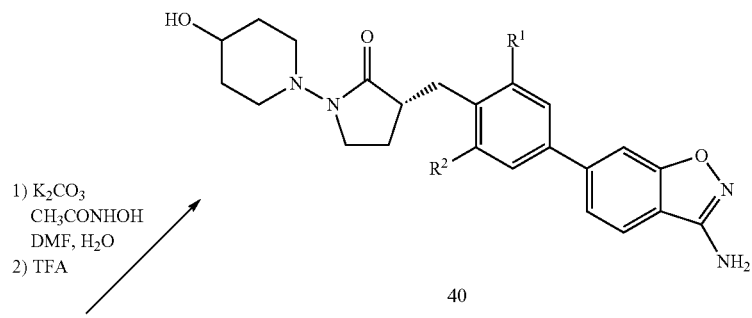

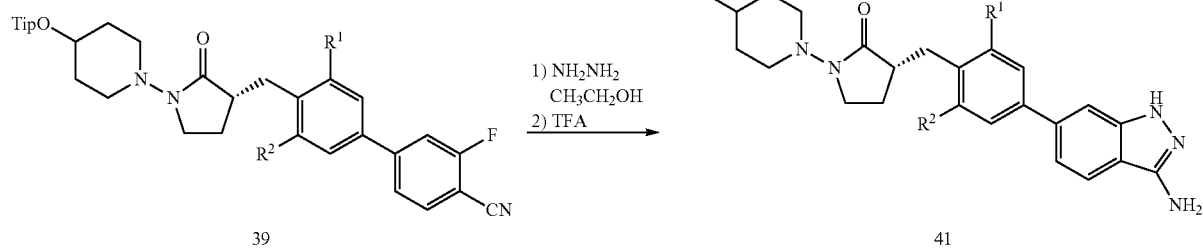
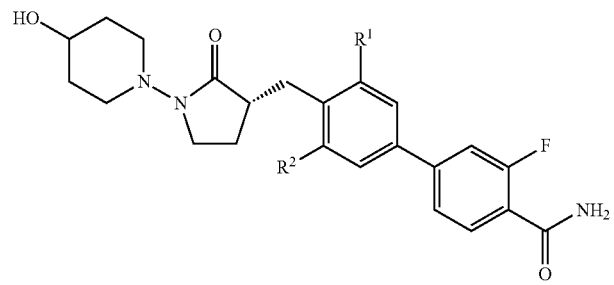
In Scheme J, benzoisoxazole (40), indazole (41) and the amide (42) are formed from compound 39 using the reagents as described.
Scheme K
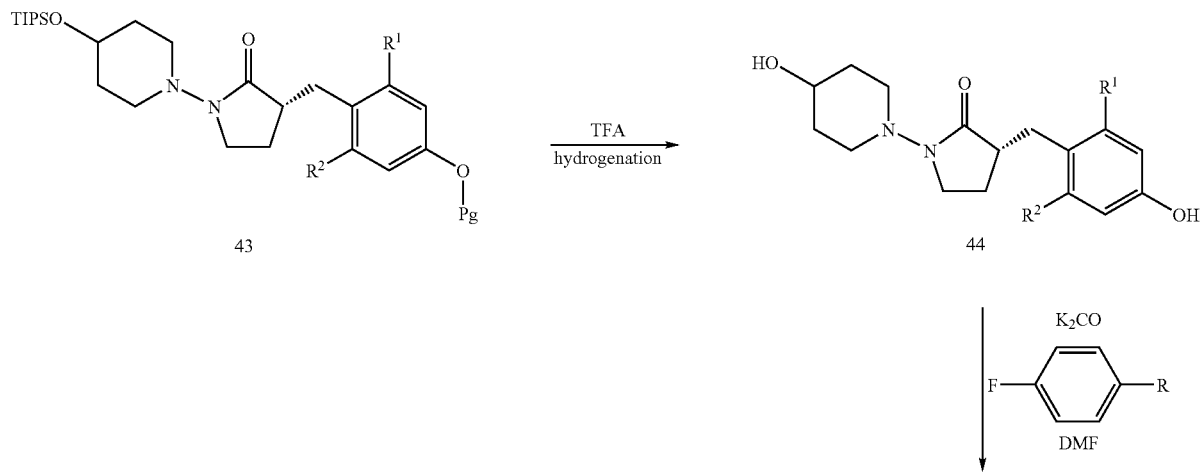

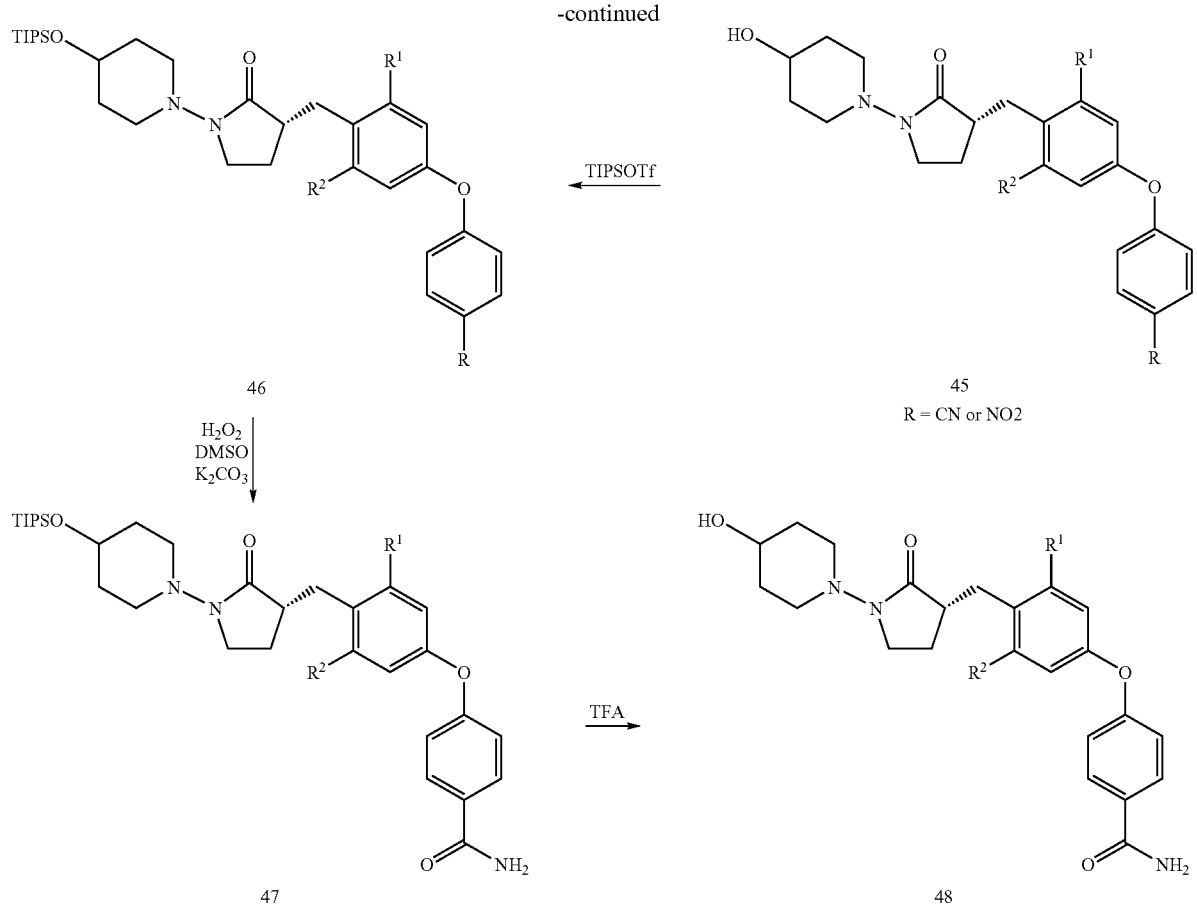

R = CN or NO2

PREPARATION 1

2,6-dichloro-4-hydroxy-benzaldehyde

Dissolve 3,5 dichlorophenol (1 kg, 6.13 mol) in 3 L dimethylformamide (DMF) and cool to 0° C. Add imidazole (918.74 g, 6.75 mol), followed by tertbutyldimethylsilyl chloride (1017.13 g, 6.75 mol). Warm the mixture to room temperature and stir for 15 minutes. Pour into water (6 L) and extract with ether (4 L). Wash the organic layer with water 2 times, 10% aqueous lithium chloride solution then brine before drying over sodium sulfate. Filter and concentrate under vacuum to obtain tert-butyl-(3,5-dichloro-phenoxy)-dimethyl-silane (1700 g) as an oil.

Dissolve tert-butyl-(3,5-dichloro-phenoxy)-dimethyl-silane (425 g, 1.5 mol) in 4 L dry tetrahydrofuran and cool to −68° C. Slowly add 1.1 equivalents of sec-butyl lithium (103.1 g, 1.61 mol) at −68° C. (~1.75 hr). After addition is complete stir the reaction at −70° C. for 30 min. Add dimethylformamide (168.5 g, 2.3 mol) and stir the reaction at −70° C. for 1 hr. Add 1 M hydrochloric acid in water (3.5 L) and allow the reaction to warm to room temperature.

Pour the reaction mixture into ether (5 L), wash with water then brine. Dry over sodium sulfate and concentrate under vacuum to an orange solid. Triturate with cold dichloromethane and filter to recover 250 g (80%) pale yellow solid.

PREPARATION 2

2,6-dichloro-4-methoxy-benzaldehyde

Combine 2,6-dichloro-4-hydroxy-benzaldehyde (120 g, 628.24 mmol) and potassium carbonate (173.65 g, 1256.5 mmol) in 900 mL dimethylformamide and treat with iodomethane (107 g, 753.9 mmol). Stir the reaction at room temperature for 3 hours. Filter off solids and pour into 6 L of water. Filter solids, wash several times with water, air dry and dissolve in ethyl acetate. Wash with water, followed by brine and then dry over sodium sulfate. Filter and concentrate under vacuum to ~100 mL volume, at which point, solids start to crash out. Filter then concentrate down the filtrate to yield a second crop. Wash with hexane, combine all solids and vacuum dry to yield 112.3 g of off-white, solid: $^1$H NMR (400 MHz, CDCl$_3$) δ 10.41 (s, 1H), 6.90 (s, 2H), 3.87 (s, 3H).

PREPARATION 3

2,6-dichloro-4-benzyloxy-benzaldehyde

Treat a mixture of 2,6-dichloro-4-hydroxy-benzaldehyde (250 g, 1.3 mol) and potassium carbonate (361.8 g, 2.62 mol) in 2 L dimethylformamide with benzyl bromide (268.64 g, 1.57 mol). Stir the reaction at room temperature for 1 hour. Filter off solids and pour into 12 L of water. Filter off solid, wash several times with water, air dry and dissolve in ethyl acetate. Dry over magnesium sulfate, filter and concentrate under vacuum to ~1.5 L. Allow to sit overnight then filter. Wash solid with minimal amount of hexane and vacuum dry. Concentrate the filtrate under vacuum and triturate with hexane to yield a second crop of product which when combined with the first crop equals 245 g white crystals. Repeat to obtain a 3rd crop of 80 g as a light-tan powder (88% overall yield): $^1$H NMR (400 MHz, DMSO-d6) δ 10.26 (s, 1H), 7.43 (m, 5H), 7.28 (s, 2H), 5.25 (s, 2H).

PREPARATION 4

(2,6-dichloro-4-methoxy-phenyl)-methanol

Suspend 2,6-dichloro-4-methoxy-benzaldehyde (112 g, 546 mmol) in 1500 mL ethanol and cool in an ice bath to 7° C. Add sodium borohydride (20.67, 546 mmol) portionwise to obtain a solution. Remove the ice bath and stir for 2 hours. Carefully add reaction mixture to saturated ammonium chloride solution (~4 L) and stir until fully quenched. Extract with dichloromethane (3×1 L) and dry the combined organic extracts over sodium sulfate. Filter and concentrate under vacuum to yield 113 g of a light-tan solid: $^1$H NMR (400 MHz, CDCl$_3$) δ 6.86 (s, 2H), 4.86 (s, 2H), 3.78 (s, 3H), 2.07 (s, 1H).

PREPARATION 5

(2,6-dichloro-4-benzyloxy-phenyl)-methanol

Prepare the title compound essentially as prepared by the method of Preparation 4. NMR (DMSO-d$_6$) δ 7.38 (m, 4H), 7.33 (m, 1H), 7.12 (s, 2H), 5.14 (s, 2H), 5.05 (t, 1H), 4.59 (d, 2H).

PREPARATION 6

2-bromomethyl-1,3-dichloro-5-methoxy-benzene

Dissolve (2,6-dichloro-4-methoxy-phenyl)-methanol (113 g, 545.76 mmol) in 1200 mL dry THF and cool to 0° C. under nitrogen. Add PBr$_3$ (59.1 g, 218.3 mmol) under nitrogen and stir at 0° C. for 30 minutes. Pour into saturated aqueous NaHCO$_3$ and extract with EtOAc. Dry and concentrate under vacuum to obtain 129.4 g product as an off-white solid. NMR (CDCl$_3$) δ 6.88 (s, 2H), 4.73 (s, 2H), 3.79 (s, 3H).

PREPARATION 7

2-bromomethyl-1,3-dichloro-5-benzyloxy-benzene

Prepare the title compound essentially as prepared by the method of Preparation 6 in an 89% yield. ES MS (m/z): 347 (M+1).

PREPARATION 8

(R)-4-benzyl-3-pent-4-enoyl-oxazolidin-2-one

Flush with nitrogen a 12 L 3-neck round bottom flask equipped with a mechanical stirrer, internal temperature probe/N$_2$ inlet, and IL addition funnel for 20 min and then add (R)-4-benzyl-2-oxazolidinone (250 g, 1.41 mol). Dilute with tetrahydrofuran (THF) (1.8 L) and cool in a dry ice/acetone bath until the internal temperature is −74° C. Transfer a 1.6M hexanes solution of n-butyllithium (970 mL, 1.552 mol) to the addition funnel via cannula, and add to the oxazolidinone solution at a rate such that the internal temperature does not reach above −65° C. After the addition is complete, allow the reaction to stir in the cooling bath 30 min. Transfer 4-pentenoyl chloride (175 mL, 1.585 mol) to the addition funnel and add dropwise to the anion solution over a 25 min period. Stir the reaction for 45 min in the cooling bath. Remove the cooling bath and stir the reaction 18 hr as it slowly reaches room temperature. Dilute the mixture with 1N aqueous hydrochloric acid (1.5 L) and diethyl ether (1 L). Separate the layers and wash the organic phase with water (2×1 L) then brine (1 L). Extract the combined aqueous washes with ether (1 L). Dry the combined organic phases over anhydrous magnesium sulfate, filter, and concentrate to 390 g of a light tan oil. Purify this material by silica gel chromatography using hexanes:ethyl acetate to obtain 345 g (94.5%) of a clear, yellow oil.

PREPARATION 9

(R)-4-benzyl-3-[(S)-2-(4-benzyloxy-2,6-dichloro-benzyl)-pent-4-enoyl]-oxazolidin-2-one Stir a mixture of (R)-4-benzyl-3-pent-4-enoyl-oxazolidin-2-one (345 g, 1.33 mol) and THF (1.8 L) in a 12 L 3-neck round bottom flask, with internal temperature probe/nitrogen inlet and addition funnel, under a nitrogen atmosphere and cool to −75° C. Transfer 1 M LiHMDS (1.6 L) to the addition funnel and add at a rate such that the internal temperature does not reach above −60° C. After the addition is complete, allow the reaction to stir at −25° C. for 30 min then cool to about −60° C. At this point add solid 2-bromomethyl-1,3-dichloro-5-benzyloxy-benzene portionwise over 5 min. After the addition is complete, transfer the reaction vessel to a −10° C. acetone bath and maintain the internal reaction temperature below 10° C. for 1 hr. Cool the mixture to 0° C. then quench with 2 L aqueous 1N hydrochloric acid. Transfer the mixture to a 22 L separatory funnel and dilute with 2.5 L water and 2 L ether. Separate the layers and extract the aqueous layer with ether. Dry the combined organic phase over anhydrous magnesium sulfate, filter and concentrate to 800 g of a thick oil. Purify by silica gel chromatography using hexanes:ethyl acetate to obtain 597 g, (86%) of a colorless oil.

PREPARATION 10

(R)-4-((R)-4-benzyl-2-oxo-oxazolidin-3-yl)-3-(4-benzyloxy-2,6-dichloro-benzyl)-4-oxo-butyraldehyde Cool a mixture of (R)-4-benzyl-3-[(S)-2-(4-benzyloxy-2,6-dichloro-benzyl)-pent-4-enoyl]-oxazolidin-2-one (100 g, 190.68 mmol) and dichloromethane (800 mL) to −74° C. Bubble ozone, produced via the A-113 ozone generator at a rate of 75%, through the reaction via carrier air at a rate of 5 CFM until the solution takes on a blue color (approx 3 hr). Add triphenylphosphine (60 g, 228.8 mmol) as a solution in 200 mL dichloromethane and allow the reaction to stir while reaching room temperature over night. Concentrate the solution under vacuum and purify by silica gel chromatography using a gradient of 20-50% ethyl acetate in hexanes to obtain 82.1 g (82%) of the product as a white foam: MS (m/z): 526 (M+).

Alternate procedure for making (R)-4-((R)-4-benzyl-2-oxo-oxazolidin-3-yl)-3-(4-benzyloxy-2,6-dichloro-benzyl)-4-oxo-butyraldehyde:

Treat a mixture of (R)-4-benzyl-3-[(S)-2-(4-benzyloxy-2,6-dichloro-benzyl)-pent-4-enoyl]-oxazolidin-2-one (0.96 g, 1.8 mmol), THF (21 mL) and water (7 mL) with 2.5% osmium tetroxide in t-butanol (46 mg, 0.18 mmol). Add sodium periodate (1.17 g, 5.5 mmol) and stir the reaction 4 hr at room temperature. Quench the reaction with water and extract with ethyl acetate. Wash the organic phase with aqueous 1N sodium thiosulfate then brine. Dry the organic layer over magnesium sulfate, filter, and concentrate under vacuum. Purify the crude material by silica gel chromatography using hexanes:ethyl acetate to elute the pure product. Concentrate the fractions containing product under vacuum to afford 0.46 g (48%) of desired product. MS (m/z): 526 (M+).

PREPARATION 11

(R)-4-benzyl-3-[(S)-2-(4-methoxy-2,6-dichloro-benzyl)-pent-4-enoyl]-oxazolidin-2-one Stir a mixture of (R)-4-benzyl-3-pent-4-enoyl-oxazolidin-2-one (5.0 g, 19.3 mmol) and tetrahydrofuran (75 mL) in a 250 mL round bottom flask at −75° C. Transfer 2 M LDA (14.5 mL) to the flask via syringe and add at a rate such that the internal temperature does not reach above −60° C. After the addition is complete, allow the reaction to stir at −25° C. for 30 min then cool to about −60° C. At this point, add a solution of 2-bromomethyl-1,3-dichloro-5-methoxy-benzene (7.76 g, 28.96 mmol) in THF (25 mL). After the addition is complete, the reaction vessel is allowed to slowly warm up to 0° C., and maintain the internal reaction temperature at 0° C. for 4 hr. Quench the reaction with 30 mL aqueous 1N hydrochloric acid. Transfer the mixture to a 500 mL separatory funnel and dilute with 100 mL water and 100 mL ether. Separate the layers and extract the aqueous layer with ether. Dry the combined organic phase over anhydrous sodium sulfate, filter and concentrate to give a thick oil. Purify by silica gel chromatography using hexanes:ethyl acetate to obtain 6.65 g, (76%) of a pale yellow oil.

PREPARATION 12

(R)-4-((R)-benzyl-2-oxo-oxazolidin-3-yl)-3-(4-methoxy-2,6-dichloro-benzyl)-4-oxo-butyraldehyde Treat a mixture of (R)-4-benzyl-3-[(S)-2-(4-methoxy-2,6-dichloro-benzyl)-pent-4-enoyl]-oxazolidin-2-one (6.65 g, 14.87 mmol), tetrahydrofuran (140 mL) and water (45 mL) with 2.5% osmium tetroxide in t-butanol (378 mL, 1.487 mmol). Add sodium periodate (9.55 g, 44.63 mmol) and stir the reaction 4 hr at room temperature. Quench the reaction with water and extract with ethyl acetate. Wash the organic phase with aqueous 1N sodium thiosulfate then brine. Dry the organic layer over magnesium sulfate, filter, and concentrate under vacuum. Purify the crude material by silica gel chromatography using hexanes:ethyl acetate to elute the pure product. Concentrate the fractions containing product under vacuum to afford 3.35 g (49%) of desired product. MS (m/z): 451 (M+).

PREPARATION 13

1-Nitroso-piperidin-4-ol

Add a solution of sodium nitrite (13.8 g, 200 mmol) in water (40 mL) to 4-hydroxy piperidine (10.1 g, 100 mmol) in water (20 mL). Cool the mixture to 0° C. on an ice bath. Add acetic acid (8.6 mL, 150 mmol) dropwise over 20 minutes. After the addition, continue stirring at 0° C. for 30 minutes, slowly warm up to room temperature and stir at room temp for 5 hours. Add sodium carbonate (15.9 g, 150 mmol) in portion to quench the acid. Extract the reaction with ethyl acetate (3×60 mL), combine the organic, dry over sodium sulfate, filter and concentrate to afford the desired product as yellow oil. Yield: 12.9 g, (98%).

PREPARATION 14

1-amino-piperidin-4-ol

Add a solution of LAH (1.0 M, 175 mL) in small portion over a period of 40 minutes to 1-nitroso-piperidin-4-ol (12.9 g) in THF (250 mL). After the addition, bring the reaction to reflux for 3 hours, cool to room temp and then to 0° C. on an ice bath. Add water (40 mL), warm the reaction slowly to room temperature for 10 minutes, and then bring to reflux for 30 minutes. Filter the precipitates, suspend in hot THF (100 mL), and filter again. Combine the filtrates, dry over sodium sulfate, filter and concentrate to give the desired product as pale yellow oil. Yield: 10.7 g, 94%.

PREPARATION 15

(R)-Trifluoro-methanesulfonic acid 3,5-dichloro-4-[1-(4-hydroxy-piperidin-1-yl)-2-oxo-pyrrolidin-3-ylmethyl]-phenyl Ester Treat a mixture of (R)-3-(2,6-dichloro-4-hydroxy-benzyl)-1-(4-hydroxy-piperidin-1-yl)-pyrrolidin-2-one (0.2 g, 0.558 mmol), 4-dimethylaminopiperidine (0.204 g, 1.676 mmol) in methylene chloride at 0° C. with trifluoromethanesulfonic anhydride (0.473 g, 1.676 mmol). Stir the reaction for 1 hour at 0° C. and 2 hours at room temperature. Dilute the reaction mixture with methylene chloride and wash with water. Dry the organic layer ($Na_2SO_4$), remove the solvent in vacuo, and purify the crude product on silica gel column with 50% ethyl acetate in hexanes to 100% ethyl acetate to afford 0.17 g (62%) of the title compound. MS (m/z): 490 (M+).

PREPARATION 16

(R)-3',5'-Dichloro-3-fluoro-4'-[2-oxo-1-(4-triisopropylsilanyloxy-piperidin-1-yl)-pyrrolidin-3-ylmethyl]-biphenyl-4-carbonitrile Purge with nitrogen for 10 minutes a mixture of (R)-trifluoro-methanesulfonic acid 3,5-dichloro-4-[2-oxo-1-(4-triisopropylsilanyloxy-piperidin-1-yl)-pyrrolidin-3-ylmethyl]-phenyl ester (0.18 g, 0.28 mmol), 3-fluoro-4-cyanophenylboronic acid (0.055 g, 0.33 mmol), sodium carbonate (0.089 g, 0.84 mmol) in THF (10 mL) and water (3 mL). Add Pd(PPh$_3$)$_4$ (0.016 g, 0.01 mmol) to the mixture. Stir the reaction at 80° C. for 1 hour. Cool the reaction, dilute with ethyl acetate, and wash with water and brine. Dry the organic layer ($Na_2SO_4$), remove the solvent in vacuo to afford crude product, and purify on silica gel column with 0% to 50% ethyl acetate in hexanes gradient to afford 0.151 g of the titled product. MS (m/z): 617 (M+).

PREPARATION 17

(R)-4-{3,5-Dichloro-4-[2-oxo-1-(4-triisopropylsilanyloxy-piperidin-1-yl)-pyrrolidin-3-ylmethyl]-phenoxy}-benzonitrile Stir a mixture of (R)-4-{3,5-dichloro-4-[1-(4-hydroxy-piperidin-1-yl)-2-oxo-pyrrolidin-3-ylmethyl]-phenoxy}-benzonitrile (0.238 g, 0.5 mmol) and 15 mL dichloromethane in an ice bath. Add pyridine (0.205 g, 2.59 mmol) followed by triisopropylsilyltrifluoromethane sulfonate (0.19 g, 0.62 mmol). Remove the cold bath and stir the reaction 1 hour at room temperature. Dilute the reaction with dichloromethane and wash with water. Dry the organic phase over sodium sulfate, filter, and concentrate. Purify the residue by silica gel chromatography by eluting with 0% to 50% ethyl acetate in hexanes gradient to afford 0.295 g of the title compound. MS (m/z): 615 (M+).

PREPARATION 18

(R)-4-{3,5-Dichloro-4-[2-oxo-1-(4-triisopropylsilanyloxy-piperidin-1-yl)-pyrrolidin-3-ylmethyl]-phenoxy}-benzamide Cool a solution of (R)-4-{3,5-dichloro-4-[2-oxo-1-(4-triisopropylsilanyloxy-piperidin-1-yl)-pyrrolidin-3-ylmethyl]-phenoxy}-benzonitrile (0.295 g, 0.48 mmol) in DMSO (5 mL) on an ice bath. Add to the solution potassium carbonate (0.331 g, 2.4 mmol) and hydrogen peroxide (30% in water, 1 mL) and stir the reaction at 0° C. for 1.5 hours and then at room temperature for 12 hours. Dilute the reaction with ethyl acetate, and wash three times with water and then one time with brine. Dry the organic phase over sodium sulfate, filter, and concentrate. Purify the residue by silica gel chromatography by eluting with 40% ethyl acetate in hexanes to 100% ethyl acetate gradient to afford 0.210 g (69%) of the title compound. MS (m/z): 633 (M+).

PREPARATION 19

(R)-Trifluoro-methanesulfonic acid 3,5-dichloro-4-(1-morpholin-4-yl-2-oxo-pyrrolidin-3-ylmethyl)-phenyl Ester Treat a mixture of (R)-3-(2,6-dichloro-4-hydroxy-benzyl)-1-morpholin-4-yl-pyrrolidin-2-one (0.4 g, 1.16 mmol) and pyridine (10 mL) at 0° C. with trifluoromethanesulfonic anhydride (1.05 g, 3.72 mmol). Stir the reaction for 1 hour at 0° C. and then for 1 hour at room temperature. Remove the excess pyridine in vacuo and, to the residue, add dichloromethane and wash with water and saturated ammonium chloride. Dry the organic layer (Na$_2$SO$_4$), remove the solvent in vacuo, and purify the crude product on silica gel column with 50% ethyl acetate in hexanes to 100% ethyl acetate to afford 0.4 g (72%) of the title compound. MS (m/z): 477 (M+).

PREPARATION 19A (R)-3-(3,5-Dichloro-4'-fluoro-biphenyl-4-ylmethyl)-1-morpholin-4-yl-pyrrolidin-2-one Trifluoroacetate Bring a mixture of trifluoro-methanesulfonic acid (R)-3,5-dichloro-4-(1-morpholin-4-yl-2-oxo-pyrrolidin-3-ylmethyl)-phenyl ester (0.126 g, 0.26 mmol), 4-fluorophenylboronic acid (0.044 g, 0.31 mmol), sodium carbonate (0.084 g, 0.79 mmol) in THF (10 mL) and water (3 mL) to 60° C. To the mixture at 60° C., add Pd(PPh$_3$)$_4$ (0.015 g, 0.011 mmol) and then raise the reaction temperature to 80° C. and stir for 2 hours. Cool the reaction, dilute with ethyl acetate, and wash with water and brine. Dry the organic layer (Na$_2$SO$_4$), remove the solvent in vacuo to afford crude product, and purify on silica gel column with 50% ethyl acetate in hexanes to 100% ethyl acetate to afford 0.102 g (92%) of the titled product and then convert to the TFA salt by treating with trifluoroacetic acid. MS (m/z): 423 (M+).

PREPARATION 19B (R)-3',5'-Dichloro-4'-(1-morpholin-4-yl-2-oxo-pyrrolidin-3-ylmethyl)-biphenyl-4-carboxylic Acid Tert-Butyl Ester Bring a mixture of (R)-trifluoro-methanesulfonic acid 3,5-dichloro-4-(1-morpholin-4-yl-2-oxo-pyrrolidin-3-ylmethyl)-phenyl ester (0.19 g, 0.4 mmol), 4-t-butyloxycarbonylphenylboronic acid (0.106 g, 0.48 mmol), sodium carbonate (0.127 g, 1.2 mmol) in THF (10 mL) and water (3 mL) to 60° C. To the mixture at 60° C., add Pd(PPh$_3$)$_4$ (0.023 g, 0.02 mmol) and then raise reaction temperature to 80° C. and stir for 3 hours. Cool the reaction, dilute with ethyl acetate, and wash with water and brine. Dry the organic layer (Na$_2$SO$_4$), remove the solvent in vacuo to afford crude product, and then purify on silica gel column with 40% ethyl acetate in hexanes to afford 0.15 g (74%) of the titled product. MS (m/z): 461 (M+).

PREPARATION 19C (R)-3',5'-Dichloro-4'-(1-morpholin-4-yl-2-oxo-pyrrolidin-3-ylmethyl)-biphenyl-4-carboxylic Acid Trifluoro Acetate Treat a solution of (R)-3',5'-dichloro-4'-(1-morpholin-4-yl-2-oxo-pyrrolidin-3-ylmethyl)-biphenyl-4-carboxylic acid tert-butyl ester (0.15 g) in dichloromethane (5 mL) with TFA (1 mL) and stir the reaction at room temperature for 12 hours. Remove the solvent and excess TFA in vacuo to afford 0.165 g (98%) of the title compound. MS (m/z): 449 (M+).

PREPARATION 20

(R)-3-(4-Benzyloxy-2,6-dichloro-benzyl)-1-(4-triisopropylsilanyloxy-piperidin-1-yl)-pyrrolidin-2-one Stir a mixture of (R)-3-(4-benzyloxy-2,6-dichloro-benzyl)-1-(4-hydroxy-piperidin-1-yl)-pyrrolidin-2-one (1.23 g, 2.75 mmol) and 15 mL of dichloromethane in an ice bath. Add pyridine (0.52 g, 6.6 mmol) followed by triisopropylsilyltrifluoromethane sulfonate (0.924 g, 3.02 mmol). Remove the cold bath and stir the reaction 12 hours at room temperature. Dilute the reaction with dichloromethane and wash with water. Dry the organic phase over sodium sulfate, filter, and concentrate. Purify the residue by silica gel chromatography by eluting with 4:1 hexanes:ethyl acetate to give 1.2 g (72%) of the title compound. MS (m/z): 605 (M+).

PREPARATION 21

(R)-3-(2,6-Dichloro-4-hydroxy-benzyl)-1-(4-triisopropylsilanyloxy-piperidin-1-yl)-pyrrolidin-2-one Purge a mixture of (R)-3-(4-benzyloxy-2,6-dichloro-benzyl)-1-(4-triisopropylsilanyloxy-piperidin-1-yl)-pyrrolidin-2-one (1.2 g) and 20% palladium (II) hydroxide on carbon (0.24 g) in ethanol (40 mL) with N$_2$ and H$_2$, and then stir under 20 psi of H$_2$ for 2 hours at room temperature. Filter the mixture through celite, and concentrate the filtrate in vacuo to afford 0.95 g (99%) of the titled product. MS (m/z): 515 (M+).

PREPARATION 22

(R)-Trifluoro-methanesulfonic acid 3,5-dichloro-4-[2-oxo-1-(4-triisopropylsilanyloxy-piperidin-1-yl)-pyrrolidin-3-ylmethyl]-phenyl Ester Treat a mixture of (R)-3-(2,6-dichloro-4-hydroxy-benzyl)-1-(4-triisopropylsilanyloxy-piperidin-1-yl)-pyrrolidin-2-one (20.2 g, 39.3 mmol), pyridine (31.05 g, 393 mmol) in methylene chloride (200 mL) at 0° C. with trifluoromethanesulfonic anhydride (13.30 g, 47.16 mmol). Stir the reaction for 1 hour at 0° C. and then for 1 hour at room temperature. Dilute the reaction mixture with methylene chloride and wash with water. Dry the organic layer ($Na_2SO_4$), remove the solvent in vacuo, and purify the crude product on silica gel column with 25% ethyl acetate in hexanes to afford 22 g (87%) of the title compound. MS (m/z): 647 (M+).

PREPARATION 23

(R)-3',5'-Dichloro-4'-[2-oxo-1-(4-triisopropylsilanyloxy-piperidin-1-yl)-pyrrolidin-3-ylmethyl]-biphenyl-4-carboxylic Acid Methyl Ester Bring a mixture of (R)-trifluoro-methanesulfonic acid 3,5-dichloro-4-[2-oxo-1-(4-triisopropylsilanyloxy-piperidin-1-yl)-pyrrolidin-3-ylmethyl]-phenyl ester (0.52 g, 0.8 mmol), 4-methoxycarbonylphenylboronic acid (0.174 g, 0.966 mmol), sodium carbonate (0.256 g, 2.41 mmol) in THF (20 mL) and water (6 mL) to 60° C. To the mixture at 60° C., add $Pd(PPh_3)_4$ (0.046 g, 0.04 mmol) and raise the reaction temperature to 80° C. and stir for 1 hour. Cool the reaction, dilute with ethyl acetate, and wash with water and brine. Dry the organic layer ($Na_2SO_4$), remove the solvent in vacuo to afford crude product, and purify on silica gel column with 25% to 50% ethyl acetate in hexanes gradient to afford 0.49 g (96%) of the titled product. MS (m/z): 633 (M+).

PREPARATION 24

(R)-3',5'-Dichloro-4'-[2-oxo-1-(4-triisopropylsilanyloxy-piperidin-1-yl)-pyrrolidin-3-ylmethyl]-biphenyl-4-carboxylic Acid Treat a solution of (R)-3',5'-dichloro-4'-[2-oxo-1-(4-triisopropylsilanyloxy-piperidin-1-yl)-pyrrolidin-3-ylmethyl]-biphenyl-4-carboxylic acid methyl ester (0.36 g) in THF (5 mL) and methanol (2 mL) with 2N LiOH (5 mL) and stir at room temperature for 3 hours. Partition the mixture between ethyl acetate (25 mL) and 1 N HCl (10 mL). Dry the organic layer ($Na_2SO_4$) and remove the solvent in vacuo to afford 0.34 g (97%) of the title compound. MS (m/z): 619 (M+).

PREPARATION 25

(R)-3-[3,5-Dichloro-4'-(4-trifluoromethyl-piperidine-1-carbonyl)-biphenyl-4-ylmethyl]-1-(4-triisopropylsilanyloxy-piperidin-1-yl)-pyrrolidin-2-one Treat a solution of (R)-3',5'-dichloro-4'-[2-oxo-1-(4-triisopropylsilanyloxy-piperidin-1-yl)-pyrrolidin-3-ylmethyl]-biphenyl-4-carboxylic acid (0.337 g, 0.545 mmol) in $CH_2Cl_2$ (20 mL) with 1,1'-carbonyldiimidazole (0.177 g, 1.09 mmol) and stir for 45 minutes at room temperature. Treat the reaction with 4-trifluoromethylpiperidine hydrochloride (0.155 g, 0.818 mmol) and diisopropylethylamine (0.106 g, 0.818 mmol) and stir for 12 hours at room temperature. Load the mixture on a silica gel column, flash with 25% to 50% ethyl acetate in hexanes to afford 0.34 g (84%) of the title compound. MS (m/z): 754 (M+).

PREPARATION 26

(R)-3-[3,5-Dichloro-4'-(4,4-difluoro-piperidine-1-carbonyl)-biphenyl-4-ylmethyl]-1-(4-triisopropylsilanyloxy-piperidin-1-yl)-pyrrolidin-2-one Treat a solution of (R)-3',5'-dichloro-4'-[2-oxo-1-(4-triisopropylsilanyloxy-piperidin-1-yl)-pyrrolidin-3-ylmethyl]-biphenyl-4-carboxylic acid (4.0 g, 6.45 mmol) in $CH_2Cl_2$ (40 mL) with 1,1'-carbonyldiimidazole (2.09 g, 12.91 mmol) and stir for 1 hour at room temperature. Treat the reaction with 4,4-difluoropiperidine hydrochloride (1.53 g, 9.68 mmol) and diisopropylethylamine (1.69 g, 9.68 mmol) and stir for 12 hours at room temperature. Load the mixture on silica gel column and flash with 25% to 35% ethyl acetate in hexanes to afford 3.8 g (81%) of the title compound. MS (m/z): 722 (M+).

PREPARATION 27

(R)-3-[3,5-Dichloro-4'-(morpholine-4-carbonyl)-biphenyl-4-ylmethyl]-1-(4-triisopropylsilanyloxy-piperidin-1-yl)-pyrrolidin-2-one Treat a solution of (R)-3',5'-dichloro-4'-[2-oxo-1-(4-triisopropylsilanyloxy-piperidin-1-yl)-pyrrolidin-3-ylmethyl]-biphenyl-4-carboxylic acid (0.2 g, 0.32 mmol) in $CH_2Cl_2$ (15 mL) with 1,1'-carbonyldiimidazole (0.10 g, 0.65 mmol) and stir for 1 hour at room temperature. Treat the reaction with morpholine (0.06 g, 0.65 mmol) and stir for 12 hours at room temperature. Load the mixture on silica gel column and flash with 25% to 35% ethyl acetate in hexanes to afford 0.20 g (90%) of the title compound. MS (m/z): 688 (M+).

PREPARATION 28

(R)-3-[4-(3-Amino-benzo[d]isoxazol-6-yl)-2,6-dichloro-benzyl]-1-(4-triisopropylsilanyloxy-piperidin-1-yl)-pyrrolidin-2-one Stir a mixture of acetohydroxamic acid (0.046 g, 0.61 mmol), potassium carbonate (0.169 g, 1.22 mmol) in DMF (5 mL) and water (2 mL) at room temperature for 10 minutes. To the mixture, add a solution of (R)-3',5'-Dichloro-3-fluoro-4'-[2-oxo-1-(4-triisopropylsilanyloxy-piperidin-1-yl)-pyrrolidin-3-ylmethyl]-biphenyl-4-carbonitrile (0.151 g, 0.244 mmol) and stir the reaction at room temperature for 5 hours and then at 60° C. for 1 hour. Cool the reaction, dilute with ethyl acetate (40 mL), and wash three times with water (15 mL each) then brine (15 mL). After drying the organic layer over sodium sulfate, filter and concentrate under vacuum. Purify the residue by silica gel chromatography with 0% to 50% ethyl acetate/hexane gradient to afford 0.095 g (62%) of the title compound. MS (m/z): 631 (M+).

PREPARATION 29

(R)-3-(2-chloro-4-hydroxy-benzyl)-1-(4-triisopropylsilanyloxy-piperidin-1-yl)-pyrrolidin-2-one Purge with $N_2$ and $H_2$ a mixture of (R)-3-(4-benzyloxy-2,6-dichloro-benzyl)-1-(4-triisopropylsilanyloxy-piperidin-1-yl)-pyrrolidin-2-one (36.61 g) and 20% palladium (II)

hydroxide on carbon (7.2 g) in ethanol (250 mL) and methanol (250 mL) and stir under a bloom of H₂ for 12 hours at room temperature. Filter the mixture through celite. Concentrate the filtrate in vacuo and purify the crude mixture on silica gel column with 25% to 35% ethyl acetate in hexane to affort 0.75 g of the titled product. MS (m/z): 481 (M+).

PREPARATION 30

Trifluoro-methanesulfonic acid 3-Chloro-4-[(R)-2-oxo-1-(4-triisopropylsilanyloxy-piperidin-1-yl)-pyrrolidin-3-ylmethyl]-phenyl Ester Treat a mixture of (R)-3-(2-Chloro-4-hydroxy-benzyl)-1-(4-triisopropylsilanyloxy-piperidin-1-yl)-pyrrolidin-2-one (0.75 g, 1.56 mmol), pyridine (1.26 g, 15.6 mmol) in methylene chloride (200 mL) at 0° C. with trifluoromethanesulfonic anhydride (0.66 g, 2.34 mmol) and stir the reaction for 1 hour at 0° C. and then 1 hour at room temperature. Dilute the reaction mixture with methylene chloride and wash with water. Dry the organic layer with Na₂SO₄, remove the solvent in vacuo, and purify the crude product on silica gel column with 25% ethyl acetate in hexanes to afford 0.94 g (98%) of the title compound. MS (m/z): 613 (M+).

PREPARATION 31

3'-Chloro-4'-[(R)-2-oxo-1-(4-triisopropylsilanyloxy-piperidin-1-yl)-pyrrolidin-3-ylmethyl]-biphenyl-4-carboxylic Acid Methyl Ester Bring a mixture of trifluoro-methanesulfonic acid 3-Chloro-4-[(R)-2-oxo-1-(4-triisopropylsilanyloxy-piperidin-1-yl)-pyrrolidin-3-ylmethyl]-phenyl ester (0.83 g, 1.35 mmol), 4-methoxycarbonylphenylboronic acid (0.29 g, 1.62 mmol), sodium carbonate (0.43 g, 4.06 mmol) in THF (20 mL) and water (6 mL) to 60° C. To the mixture at 60° C., add Pd(PPh₃)₄ (0.08 g, 0.07 mmol). Raise the reaction temperature to 80° C. and stir for 1 hour. Cool the reaction, dilute with ethyl acetate, and wash with water and brine. Dry the organic layer with Na₂SO₄, remove the solvent in vacuo, and purify on silica gel column with 0% to 50% ethyl acetate in hexanes gradient to afford 0.76 g (93%) of the titled product. MS (m/z): 599 (M+).

PREPARATION 32

3'-Chloro-4'-[(R)-2-oxo-1-(4-triisopropylsilanyloxy-piperidin-1-yl)-pyrrolidin-3-ylmethyl]-biphenyl-4-carboxylic Acid Treat a solution of 3'-Chloro-4'-[(R)-2-oxo-1-(4-triisopropylsilanyloxy-piperidin-1-yl)-pyrrolidin-3-ylmethyl]-biphenyl-4-carboxylic acid methyl ester (0.76 g) in THF (15 mL) with 2N LiOH (15 mL) at room temperature for 5 hours. Partition the mixture between ethyl acetate (25 mL) and 1 N HCl (10 mL). Dry the organic layer with Na₂SO₄ and remove the solvent in vacuo to afford 0.73 g (98%) of the title compound. MS (m/z): 585 (M+).

PREPARATION 33

(R)-3-[3'-Chloro-4'-(4-trifluoromethyl-piperidine-1-carbonyl)-biphenyl-4-ylmethyl]-1-(4-triisopropylsilanyloxy-piperidin-1-yl)-pyrrolidin-2-one Treat a solution of 3'-chloro-4'-[(R)-2-oxo-1-(4-triisopropylsilanyloxy-piperidin-1-yl)-pyrrolidin-3-ylmethyl]-biphenyl-4-carboxylic acid (0.2 g, 0.34 mmol) in CH₂Cl₂ (15 mL) with 1,1'-carbonyldiimidazole (0.11 g, 0.68 mmol) and stir for 60 minutes at room temperature. Treat the reaction with 4-trifluoromethylpiperidine hydrochloride (0.10 g, 0.51 mmol) and diisopropylethylamine (0.07 g, 0.51 mmol) and stir for 12 hours at room temperature. Load the mixture on silica gel column, flash with 0% to 50% ethyl acetate in hexanes to afford 0.12 g (49%) of the title compound. MS (m/z): 720 (M+).

PREPARATION 34

(R)-3-[3-Chloro-4'-(4,4-difluoro-piperidine-1-carbonyl)-biphenyl-4-ylmethyl]-1-(4-triisopropylsilanyloxy-piperidin-1-yl)-pyrrolidin-2-one Treat a solution of 3'-chloro-4'-[2-oxo-1-(4-triisopropylsilanyloxy-piperidin-1-yl)-pyrrolidin-3-ylmethyl]-biphenyl-4-carboxylic acid (0.2 g, 0.34 mmol) in CH₂Cl₂ (15 mL) with 1,1'-carbonyldiimidazole (0.11 g, 0.68 mmol) and stir for 1 hour at room temperature. Treat the reaction with 4,4-difluoropiperidine hydrochloride (0.08 g, 0.51 mmol) and diisopropylethylamine (0.07 g, 0.51 mmol) and stir for 12 hours at room temperature. Load the mixture on silica gel column, flash with 0% to 50% ethyl acetate in hexanes to afford 0.15 g (64%) of the title compound. MS (m/z): 688 (M+).

PREPARATION 35

(S)-4-Benzyl-3-[(R)-2-(4-benzyloxy-2,6-dichloro-benzyl)-pent-4-enoyl]-oxazolidin-2-one Dissolve 4-Benzyl-3-pent-4-enoyl-oxazolidin-2-one (2.21 g, 8.52 mmol) in 25 ml of dry THF. Chilled to −78° C. Add LiN(TMS)₂ (10.23 ml, 10.23 mmol). Stir for 30 min at same temperature. Add 5-Benzyloxy-2-bromomethyl-1,3-dichloro-benzene (3.10 g, 8.95 mmol) in 5 ml of THF. Let the reaction slowly warm to room temperature.

Quench with ammonium chloride saturated solution. Extract in ethyl acetate. Column separation affords 3.09 g (69%) of product.

PREPARATION 36

(S)-4-((S)-4-Benzyl-2-oxo-oxazolidin-3-yl)-3-(4-benzyloxy-2,6-dichloro-benzyl)-4-oxo-butyraldehyde Dissolve 4-Benzyl-3-[2-(4-benzyloxy-2,6-dichloro-benzyl)-pent-4-enoyl]-oxazolidin-2-one (3.09 g, 5.89 mmol) in 3/1 mix of THF/water (100 ml). Add OsO₄ (5.99 g, 0.59 mmol) and NaIO₄ (3.82 g, 17.86 mmol). Stir the resulting suspension for 3 hr at room temperature. Quench with 1M solution of sodium thiosulfate (300 ml). Extract in ethyl acetate. Column separation affords 0.885 g (28.5%) of 4-(4-Benzyl-2-oxo-oxazolidin-3-yl)-3-(4-benzyloxy-2,6-dichloro-benzyl)-4-oxo-butyraldehyde.

EXAMPLE 1

(R)-3-(4-Benzyloxy-2,6-dichloro-benzyl)-1-morpholin-4-yl-pyrrolidin-2-one

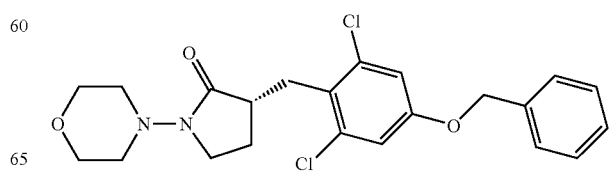

Stir a mixture of dichloroethane (25 mL), N-aminomorpholine (0.204 g, 2 mmol), (R)-4-((R)-4-benzyl-2-oxo-oxazolidin-3-yl)-3-(4-benzyloxy-2,6-dichloro-benzyl)-4-oxo-butyraldehyde (1.064 g, 2 mmol) and sodium triacetoxyborohydride (1.266 g, 6 mmol) at room temperature for 12 hours. Bring the reaction to 60° C. and stir for 3 hours. Cool the reaction, dilute with dichloromethane, and wash with water. Dry the organic layer (Na$_2$SO$_4$), remove the solvent in vacuo to afford crude product, and purify on silica with a 50 to 75% ethyl acetate in hexanes gradient to afford 0.07 g (80%) of the titled product. MS (m/z): 435 (M+).

EXAMPLE 2

(R)-3-(2,6-Dichloro-4-hydroxy-benzyl)-1-morpholin-4-yl-pyrrolidin-2-one

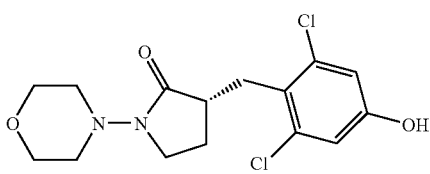

Purge a mixture of (R)-3-(4-benzyloxy-2,6-dichloro-benzyl)-1-morpholin-4-yl-pyrrolidin-2-one (0.66 g) and 20% palladium (II) hydroxide on carbon (0.15 g) in ethyl acetate (30 mL) with N$_2$ and H$_2$ and stir under a balloon of H$_2$ for 2 hours at room temperature. Filter the mixture through celite and concentrate the filtrate in vacuo to afford 0.43 g (82%) of the titled product. MS (m/z): 345 (M+).

EXAMPLE 3

(R)-3-[3,5-Dichloro-4'-(4-trifluoromethyl-piperidine-1-carbonyl)-biphenyl-4-ylmethyl]-1-morpholin-4-yl-pyrrolidin-2-one

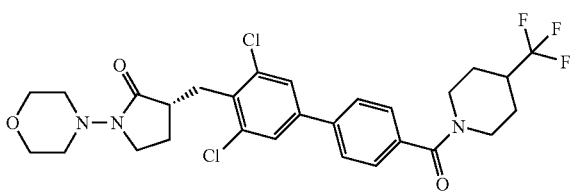

Treat a mixture of (R)-3',5'-dichloro-4'-(1-morpholin-4-yl-2-oxo-pyrrolidin-3-ylmethyl)-biphenyl-4-carboxylic acid trifluoro acetate (0.16 g, 0.28 mmol) in CH$_2$Cl$_2$ (10 mL) with 1,1'-carbonyldiimidazole (0.092 g, 0.57 mmol), 4-trifluoromethylpiperidine hydrochloride (0.081 g, 0.43 mmol) and diisopropylethylamine (0.110 g, 0.86 mmol) and stir for 12 hours at room temperature. Load the mixture on silica gel column and flash with 50% ethyl acetate in hexanes to 100% ethyl acetate to afford 0.081 g of a mixture of the title compound and impurity. Re-purify via reverse phase HPLC to afford 0.055 g (34%) of the title compound. MS (m/z): 584 (M+).

EXAMPLE 4

(R)-3-(4-Benzyloxy-2,6-dichloro-benzyl)-1-(4-hydroxy-piperidin-1-yl)-pyrrolidin-2-one

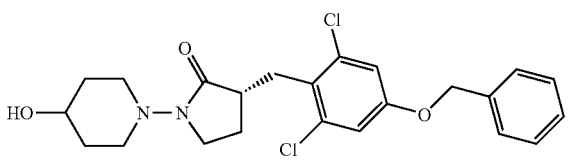

Stir a mixture of dichloroethane (500 mL), N-amino-4-hydroxypiperidine (10.66 g, 91.88 mmol), (R)-4-((R)-4-benzyl-2-oxo-oxazolidin-3-yl)-3-(4-benzyloxy-2,6-dichloro-benzyl)-4-oxo-butyraldehyde (40.2 g, 76.57 mmol) and sodium triacetoxyborohydride (48.47 g, 229.71 mmol) at room temperature for 21 hours. Bring the reaction to 55° C. and is stir for 1 hour. Cool the reaction, dilute with dichloromethane, and wash with water. Dry the organic layer (Na$_2$SO$_4$), remove the solvent in vacuo to afford crude product, and purify on silica with a 100% ethyl acetate and 10% methanol in methylene chloride to afford 30 g (90%) of the titled product. MS (m/z): 449 (M+).

EXAMPLE 5

(R)-3-(2,6-Dichloro-4-hydroxy-benzyl)-1-(4-hydroxy-piperidin-1-yl)-pyrrolidin-2-one

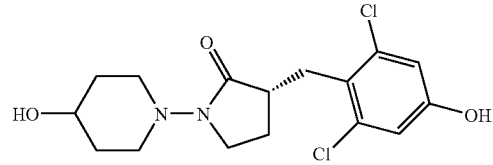

Purge a mixture of (R)-3-(4-benzyloxy-2,6-dichloro-benzyl)-1-(4-hydroxy-piperidin-1-yl)-pyrrolidin-2-one (0.26 g) and 20% palladium (II) hydroxide on carbon (0.08 g) in ethyl acetate (25 mL) with N$_2$ and H$_2$, and then stir under a balloon of H$_2$ for 4 hours at room temperature. Filter the mixture through celite and concentrate the filtrate in vacuo to afford 0.205 g (99%) of the titled product. MS (m/z): 359 (M+).

EXAMPLE 6

(R)-3-(3,5-Dichloro-4'-fluoro-biphenyl-4-ylmethyl)-1-(4-hydroxy-piperidin-1-yl)-pyrrolidin-2-one Trifluoro Acetate

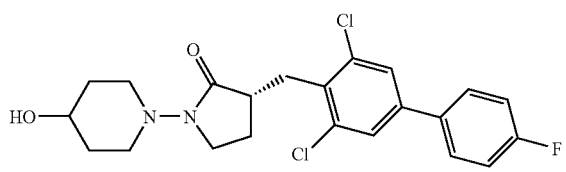

Bring a mixture of trifluoro-methanesulfonic acid (R)-3,5-dichloro-4-[1-(4-hydroxy-piperidin-1-yl)-2-oxo-pyrrolidin-3-ylmethyl]-phenyl ester (0.102 g, 0.21 mmol), 4-fluorophenylboronic acid (0.035 g, 0.25 mmol), sodium carbonate (0.066 g, 0.62 mmol) in THF (10 mL) and water (3 mL) to 60° C. To the mixture at 60° C., add Pd(PPh$_3$)$_4$ (0.015 g, 0.011 mmol), raise the reaction temperature to 80° C., and stir for 2.5 hours. Cool the reaction, dilute with ethyl acetate, and wash with water and brine. Dry the organic layer (Na$_2$SO$_4$), remove the solvent in vacuo to afford crude product, and purify on silica gel column and HPLC (Reverse Phase) to afford 0.02 g of the titled product.

MS (m/z): 437 (M+).

EXAMPLE 7

(R)-3-[3,5-Dichloro-4'-(4-trifluoromethyl-piperidine-1-carbonyl)-biphenyl-4-ylmethyl]-1-(4-hydroxy-piperidin-1-yl)-pyrrolidin-2-one

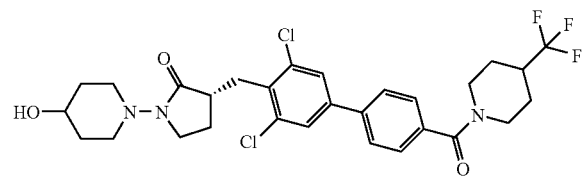

Treat a mixture of (R)-3-[3,5-dichloro-4'-(4-trifluoromethyl-piperidine-1-carbonyl)-biphenyl-4-ylmethyl]-1-(4-triisopropylsilanyloxy-piperidin-1-yl)-pyrrolidin-2-one (0.34 g), THF (6 mL) and water (6 mL) with TFA (2 mL) at room temperature for 1 hour and at 50° C. for 2 hours. Cool the reaction, dilute with ethyl acetate, and wash with sodium bicarbonate (sat.). Dry the organic layer (Na$_2$SO$_4$), remove the solvent in vacuo to afford crude product, and purify on silica gel column with 100% ethyl acetate and 10% methanol in methylene chloride to afford 0.205 g (76%) of the titled product. MS (m/z): 598 (M+).

EXAMPLE 8

(R)-3-[3,5-Dichloro-4'-(4,4-difluoro-piperidine-1-carbonyl)-biphenyl-4-ylmethyl]-1-(4-hydroxy-piperidin-1-yl)-pyrrolidin-2-one

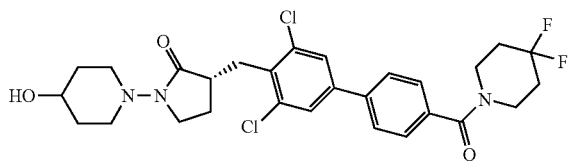

Add water (60 mL) and TFA 20 mL) to a solution of (R)-3-[3,5-dichloro-4'-(4,4-difluoro-piperidine-1-carbonyl)-biphenyl-4-ylmethyl]-1-(4-triisopropylsilanyloxy-piperidin-1-yl)-pyrrolidin-2-one in THF (60 mL). Stir the mixture at room temp for 12 hours. Partition the reaction with ethyl acetate (200 mL) and sodium bicarbonate (sat. solution, 150 mL), separate the organic layer, extract the aqueous with another 200 mL of ethyl acetate, and combine the organic solutions. Dry over sodium sulfate, filter and concentrate. Dissolve the residue in 40 mL of dichloromethane and load on a Biotage Si 65M 1385-1 column, flash with ethyl acetate for 30 minutes, switch to 8% methanol in dichloromethane to afford 8.02 grams (97%) of the desired product as white solid. MS (m/z): 566 (M+).

EXAMPLE 9

(R)-3-[3,5-Dichloro-4'-(morpholine-4-carbonyl)-biphenyl-4-ylmethyl]-1-(4-hydroxy-piperidin-1-yl)-pyrrolidin-2-one

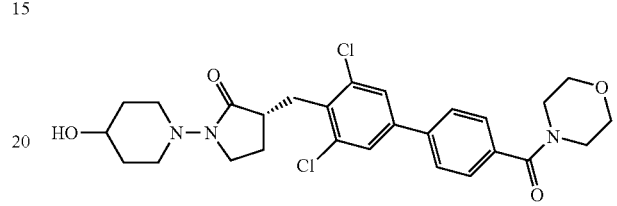

Add water (3 mL) and TFA (1 mL) to a solution of (R)-3-[3,5-Dichloro-4'-(morpholine-4-carbonyl)-biphenyl-4-ylmethyl]-1-(4-triisopropylsilanyloxy-piperidin-1-yl)-pyrrolidin-2-one in THF (3 mL). Stir the mixture at room temp for 12 hours. Partition the reaction with ethyl acetate (20 mL) and sodium bicarbonate (sat. solution, 15 mL), separate the organic layer, extract the aqueous with another 20 mL of ethyl acetate, and combine the organic solutions. Dry over sodium sulfate, filter and concentrate. Dissolve the residue in 4 mL of dichloromethane, load on silica gel column, and flash with ethyl acetate for 15 minutes and then switch to 8% methanol in dichloromethane to afford 0.13 grams (84%) of the desired product as white solid. MS (m/z): 532 (M+).

EXAMPLE 10

(R)-3-[4-(3-Amino-benzo[d]isoxazol-6-yl)-2,6-dichloro-benzyl]-1-(4-hydroxy-piperidin-1-yl)-pyrrolidin-2-one

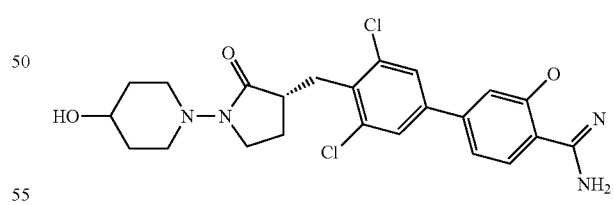

Add water (3 mL) and TFA (1 mL) to (R)-3-[4-(3-amino-benzo[d]isoxazol-6-yl)-2,6-dichloro-benzyl]-1-(4-triisopropylsilanyloxy-piperidin-1-yl)-pyrrolidin-2-one (0.095 g) in THF (3 mL). Stir the mixture at room temperature for 5 hours. Dilute the reaction with ethyl acetate, wash with sodium bicarbonate (sat. solution), separate the organic layer, dry over sodium sulfate, filter and concentrate. Purify the residue on silica gel column by using ethyl acetate first, then switch to 5% methanol in dichloromethane to afford 0.062 g (87%) of the desired product as white solid. MS (m/z): 475 (M+).

EXAMPLE 11

(R)-4-{3,5-Dichloro-4-[1-(4-hydroxy-piperidin-1-yl)-2-oxo-pyrrolidin-3-ylmethyl]-phenoxy}-benzonitrile

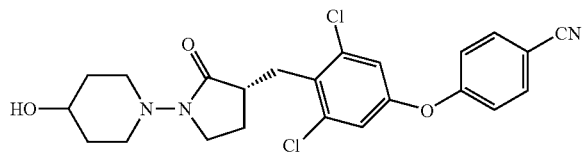

Add potassium carbonate (0.385 g, 2.8 mmol) and 4-fluorobenzonitrile (0.253 g, 2.1 mmol) to a solution of (R)-3-(2,6-dichloro-4-hydroxy-benzyl)-1-(4-hydroxy-piperidin-1-yl)-pyrrolidin-2-one (0.5 g, 1.4 mmol) in DMSO. Stir the reaction at 80° C. for 3 hours. Cool the reaction, dilute with ethyl acetate, and wash three times with water and one time with brine. After drying the organic layer over sodium sulfate, filter and concentrate under vacuum. Purify the residue by silica gel chromatography with 50% ethyl acetate/hexane to 100% ethyl acetate gradient to afford 0.32 g (50%) of the title compound. MS (m/z): 460 (M+).

EXAMPLE 12

(R)-4-{3,5-Dichloro-4-[1-(4-hydroxy-piperidin-1-yl)-2-oxo-pyrrolidin-3-ylmethyl]-phenoxy}-benzamide

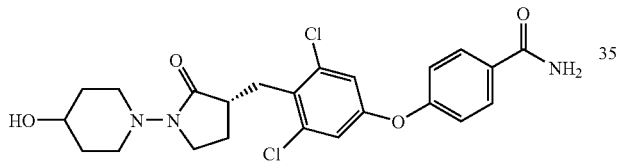

Add water (6 mL) and TFA (2 mL) to (R)-4-{3,5-dichloro-4-[2-oxo-1-(4-triisopropylsilanyloxy-piperidin-1-yl)-pyrrolidin-3-ylmethyl]-phenoxy}-benzamide (0.21 g) in THF (6 mL). Stir the mixture at room temperature for 12 hours. Dilute the reaction with ethyl acetate and wash with sodium bicarbonate (sat. solution), separate the organic layer, dry over sodium sulfate, filter and concentrate. Purify the residue on silica gel column by using ethyl acetate first, then switch to 5% methanol in dichloromethane to afford 0.158 g (100%) of the desired product as white solid. MS (m/z): 478 (M+).

EXAMPLE 13

(R)-3-(3,5-Dichloro-4'-trifluoromethyl-biphenyl-4-ylmethyl)-1-(4-hydroxy-piperidin-1-yl)-pyrrolidin-2-one

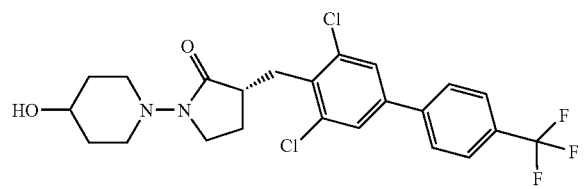

Bring a mixture of trifluoro-methanesulfonic acid 3,5-dichloro-4-[(R)-2-oxo-1-(4-triisopropylsilanyloxy-piperidin-1-yl)-pyrrolidin-3-ylmethyl]-phenyl ester (0.18 g, 0.29 mmol), 4-trifluoromethylphenylboronic acid (0.07 g, 0.36 mmol), sodium carbonate (0.09 g, 0.86 mmol) in THF (26 mL) and water (13 mL) to 60° C. To the mixture at 60° C., add Pd(PPh$_3$)$_4$ (0.02 g, 0.01 mmol). Raise the reaction temperature to 80° C. and stir for 1 hour. Cool the reaction, dilute with ethyl acetate, and wash with water and brine. Dry the organic layer (Na$_2$SO$_4$), remove the solvent in vacuo to afford crude product, and purify on silica gel column with 25% to 50% ethyl acetate in hexanes gradient to afford 0.12 g of (R)-3-(3,5-Dichloro-4'-trifluoromethyl-biphenyl-4-ylmethyl)-1-(4-triisopropylsilanyloxy-piperidin-1-yl)-pyrrolidin-2-one.

To a mixture of (R)-3-(3,5-Dichloro-4'-trifluoromethyl-biphenyl-4-ylmethyl)-1-(4-triisopropylsilanyloxy-piperidin-1-yl)-pyrrolidin-2-one (0.12 g) in THF (6 mL), add water (6 mL) and TFA (2 mL). Stir the mixture at room temperature for 12 hours. Dilute the reaction mixture with ethyl acetate and wash with sodium bicarbonate (Sat.) and water. Separate the organic and dry over sodium sulfate, filter and concentrate. Purify the crude mixture on silica gel column with 50% ethyl acetate in hexane to 100% ethyl acetate to afford 0.088 g of the titled product. MS (m/z): 487 (M+).

EXAMPLE 14

(R)-3-(3,5-Dichloro-4'-methanesulfonyl-biphenyl-4-ylmethyl)-1-(4-hydroxy-piperidin-1-yl)-pyrrolidin-2-one

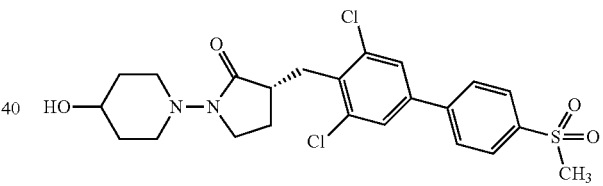

Bring a mixture of trifluoro-methanesulfonic acid 3,5-dichloro-4-[(R)-2-oxo-1-(4-triisopropylsilanyloxy-piperidin-1-yl)-pyrrolidin-3-ylmethyl]-phenyl ester (0.14 g, 0.22 mmol), 4-methylsulfonylphenylboronic acid (0.06 g, 0.28 mmol), sodium carbonate (0.07 g, 0.67 mmol) in THF (26 mL) and water (13 mL) to 60° C. To the mixture at 60° C., add Pd(PPh$_3$)$_4$ (0.02 g, 0.01 mmol). Raise the reaction temperature to 80° C. and stir for 1 hour. Cool the reaction, dilute with ethyl acetate, and wash with water and brine. Dry the organic layer (Na$_2$SO$_4$), remove the solvent in vacuo to afford crude product, and purify on silica gel column with 25% to 50% ethyl acetate in hexanes gradient to afford 0.12 g of (R)-3-(3,5-Dichloro-4'-methanesulfonyl-biphenyl-4-ylmethyl)-1-(4-triisopropylsilanyloxy-piperidin-1-yl)-pyrrolidin-2-one.

To a mixture of (R)-3-(3,5-Dichloro-4'-methanesulfonyl-biphenyl-4-ylmethyl)-1-(4-triisopropylsilanyloxy-piperidin-1-yl)-pyrrolidin-2-one (0.12 g) in THF (6 mL), add water (6 mL) and TFA (2 mL). Stir the mixture at room temperature for 12 hours. Dilute the reaction mixture with ethyl acetate and wash with sodium bicarbonate (Sat.) and water. Separate the organic and dry over sodium sulfate, filter and concentrate. Purify the crude mixture on silica gel column with 50% ethyl acetate in hexane to 100% ethyl acetate to afford 0.088 g of the titled product. MS (m/z): 497 (M+).

EXAMPLE 15

(R)-3-[3'-Chloro-4'-(4-trifluoromethyl-piperidine-1-carbonyl)-biphenyl-4-ylmethyl]-1-(4-hydroxy-piperidin-1-yl)-pyrrolidin-2-one

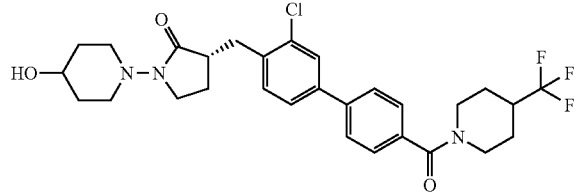

Treat a mixture of (R)-3-[3'-chloro-4'-(4-trifluoromethyl-piperidine-1-carbonyl)-biphenyl-4-ylmethyl]-1-(4-triisopropylsilanyloxy-piperidin-1-yl)-pyrrolidin-2-one (0.12 g), THF (3 mL) and water (3 mL) with TFA (1 mL) at room temperature for 5 hours. Dilute the reaction with ethyl acetate and wash with sodium bicarbonate (sat.). Dry the organic layer (Na₂SO₄), remove the solvent in vacuo to afford crude product, and purify on silica gel column with 100% ethyl acetate and 10% methanol in methylene chloride to afford 0.05 g (53%) of the titled product. MS (m/z): 564 (M+).

EXAMPLE 16

(R)-3-[3-Chloro-4'-(4,4-difluoro-piperidine-1-carbonyl)-biphenyl-4-ylmethyl]-1-(4-hydroxy-piperidin-1-yl)-pyrrolidin-2-one

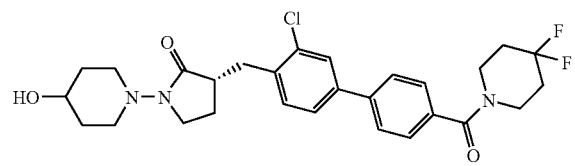

To a solution of (R)-3-[3-chloro-4'-(4,4-difluoro-piperidine-1-carbonyl)-biphenyl-4-ylmethyl]-1-(4-triisopropylsilanyloxy-piperidin-1-yl)-pyrrolidin-2-one (0.15 g) in THF (3 mL), add water (3 mL) and TFA 1 mL). Stir the mixture at room temperature for 5 hours. Partition the reaction with ethyl acetate and sodium bicarbonate (sat. solution), separate the organic layer, extract the aqueous with ethyl acetate again, combine the organic solutions, dry over sodium sulfate, filter and concentrate. Purify the residue on silica gel column with ethyl acetate for 30 minutes and then switch to 8% methanol in dichloromethane to afford 0.06 grams (52%) of the desired product as white solid. MS (m/z): 532 (M+).

EXAMPLE 17

(S)-3-[3,5-Dichloro-4'-(4-trifluoromethyl-piperidine-1-carbonyl)-biphenyl-4-ylmethyl]-1-(4-hydroxy-piperidin-1-yl)-pyrrolidin-2-one

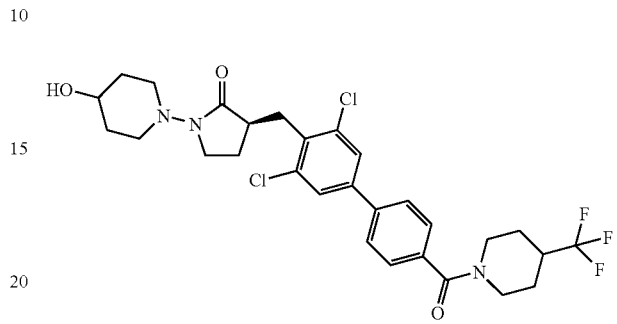

Synthesize the title compound using the same procedure as described in Example 7 except use (S)-4-((S)-4-Benzyl-2-oxo-oxazolidin-3-yl)-3-(4-benzyloxy-2,6-dichloro-benzyl)-4-oxo-butyraldehyde. MS (m/z): 598 (M+).

EXAMPLE 18

Crystalline (R)-3-[3,5-Dichloro-4'-(4-trifluoromethyl-piperidine-1-carbonyl)-biphenyl-4-ylmethyl]-1-(4-hydroxy-piperidin-1-yl)-pyrrolidin-2-one Anhydrate Dissolve amorphous (R)-3-[3,5-Dichloro-4'-(4-trifluoromethyl-piperidine-1-carbonyl)-biphenyl-4-ylmethyl]-1-(4-hydroxy-piperidin-1-yl)-pyrrolidin-2-one (100 mg) in heptane (1 mL) and EtOAc (1 mL) with heat (<50° C.) and stirring. A crystal slurry forms from the warm solution within 30 minutes. Maintain the slurry at 40-45° C. overnight, then isolate the solid product by vacuum filtration and air dry to give the title compound (91 mg).

Alternate procedure for preparing Crystalline (R)-3-[3,5-Dichloro-4'-(4-trifluoromethyl-piperidine-1-carbonyl)-biphenyl-4-ylmethyl]-1-(4-hydroxy-piperidin-1-yl)-pyrrolidin-2-one anhydrate: Dissolve amorphous (R)-3-[3,5-Dichloro-4'-(4-trifluoromethyl-piperidine-1-carbonyl)-biphenyl-4-ylmethyl]-1-(4-hydroxy-piperidin-1-yl)-pyrrolidin-2-one (25 mg) in about 40 volumes of approximately 3:1 v/v EtOAc:heptane with mild heat and stirring. Allow the solution to equilibrate at room temperature with stirring and seed with (R)-3-[3,5-Dichloro-4'-(4-trifluoromethyl-piperidine-1-carbonyl)-biphenyl-4-ylmethyl]-1-(4-hydroxy-piperidin-1-yl)-pyrrolidin-2-one hydrate. A crystal slurry forms within 45 minutes. Remove the mother liquor via pipet and allow the wet solids to air dry.

Alternate procedure for preparing Crystalline (R)-3-[3,5-Dichloro-4'-(4-trifluoromethyl-piperidine-1-carbonyl)-biphenyl-4-ylmethyl]-1-(4-hydroxy-piperidin-1-yl)-pyrrolidin-2-one: Dissolve 59.5 g of amorphous (R)-3-[3,5-Dichloro-4'-(4-trifluoromethyl-piperidine-1-carbonyl)-biphenyl-4-ylmethyl]-1-(4-hydroxy-piperidin-1-yl)-pyrrolidin-2-one foam in 110 mL of acetone. Add a seed crystal of crystalline (R)-3-[3,5-Dichloro-4'-(4-trifluoromethyl-piperidine-1-carbonyl)-biphenyl-4-ylmethyl]-1-(4-hydroxy-piperidin-1-yl)-pyrrolidin-2-one and stir the slurry for 2 hours. Collect the white solid by filtration and dry in a vacuum oven to afford 53.2 g of crystalline (R)-3-[3,5-Dichloro-4'-(4-trifluoromethyl-piperidine-1-carbonyl)-biphenyl-4-ylmethyl]-1-(4-hydroxy-piperidin-1-yl)-pyrrolidin-2-one.

X-Ray Powder Diffraction

X-ray powder diffraction analysis is performed with a D4 Endeaver diffractometer, equipped with a CuKα source ($\lambda$=1.54056 Å) operating at 40 kV and 50 mA. The sample is scanned from 3° to 40° in 2θ, with a step size of 0.009° in 2θ and a scan rate of $\geq$3 sec per step. Sample displacement errors may be corrected using the NIST standard SRM675 (standard peak at 8.8° in 2θ). It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g. The United States Pharmacopeia #23, National Formulary #18, pages 1843-1844, 1995. Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability of ±0.1 in 2-theta will take into account these potential variations without hindering the unequivocal identification of the indicated crystal form.

Confirmation of a crystal form may be made based on any unique combination of distinguishing peaks (in units of ° 2θ), typically the more prominent peaks. Crystalline (R)-3-[3,5-Dichloro-4'-(4-trifluoromethyl-piperidine-1-carbonyl)-biphenyl-4-ylmethyl]-1-(4-hydroxy-piperidin-1-yl)-pyrrolidin-2-one is characterized by an X-ray powder diffraction pattern having distinguishing peaks at a 2θ value of 8.6° and 15.3°. Crystalline (R)-3-[3,5-Dichloro-4'-(4-trifluoromethyl-piperidine-1-carbonyl)-biphenyl-4-ylmethyl]-1-(4-hydroxy-piperidin-1-yl)-pyrrolidin-2-one can be further characterized by an X-ray powder diffraction pattern having distinguishing peaks at a 2θ values of 8.6°, 15.3°, and 17.4°. All diffraction angles are expressed with a tolerance of 0.1 degrees.

TABLE 1

X-ray powder diffraction (CuKα radiation source, $\lambda$ = 1.54056 Å) peaks of crystalline (R)-3-[3,5-Dichloro-4'-(4-trifluoromethyl-piperidine-1-carbonyl)-biphenyl-4-ylmethyl]-1-(4-hydroxy-piperidin-1-yl)-pyrrolidin-2-one anhydrate.

| 2-Theta Angle (±0.1°) | Intensity (%) |
| --- | --- |
| 6.3 | 10.1 |
| 8.6 | 57.0 |
| 10.7 | 10.1 |
| 14.3 | 13.4 |
| 14.4 | 19.3 |
| 15.3 | 59.6 |
| 16.8 | 100.0 |
| 17.4 | 42.2 |
| 19.5 | 34.3 |
| 19.7 | 35.8 |
| 20.2 | 81.6 |
| 21.1 | 13.1 |
| 22.7 | 39.4 |
| 23.9 | 10.8 |
| 25.4 | 24.2 |
| 27.7 | 14.5 |

Scheme L
Alternate procedure for preparing (R)-3-[3,5-Dichloro-4'-(4-trifluoromethyl-piperidine-1-carbonyl)-biphenyl-4-ylmethyl]-1-(4-hydroxy-piperidin-1-yl)-pyrrolidin-2-one

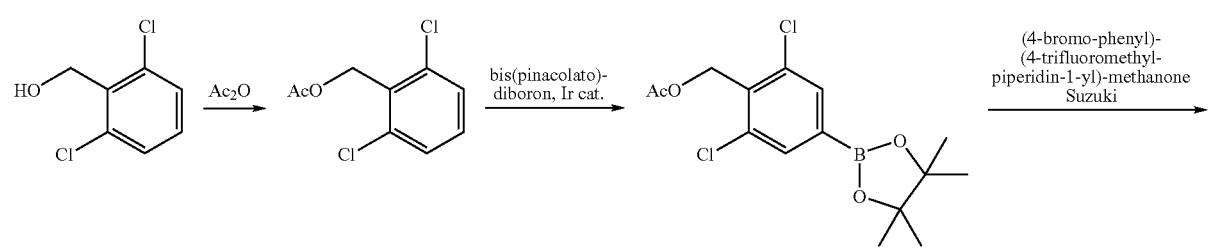

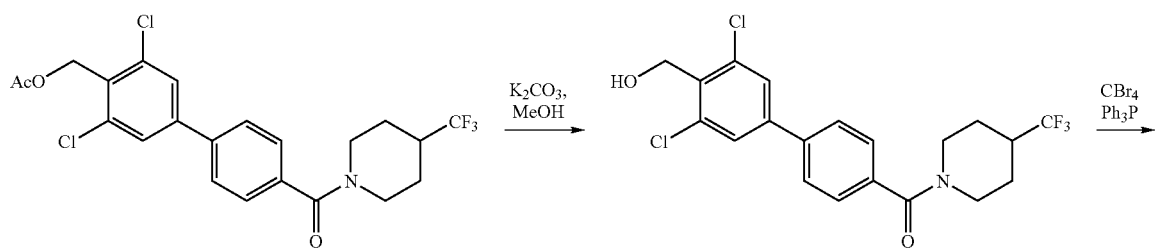

-continued
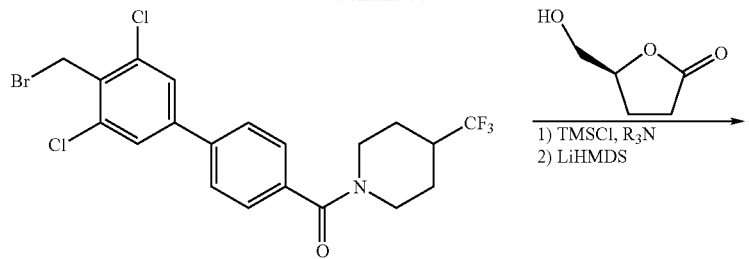
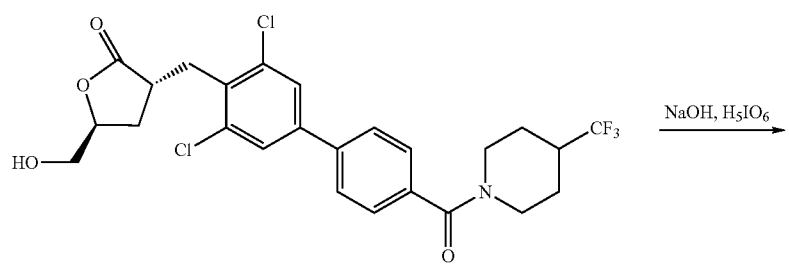
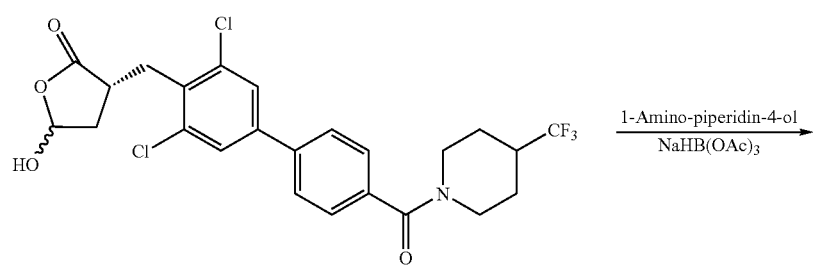
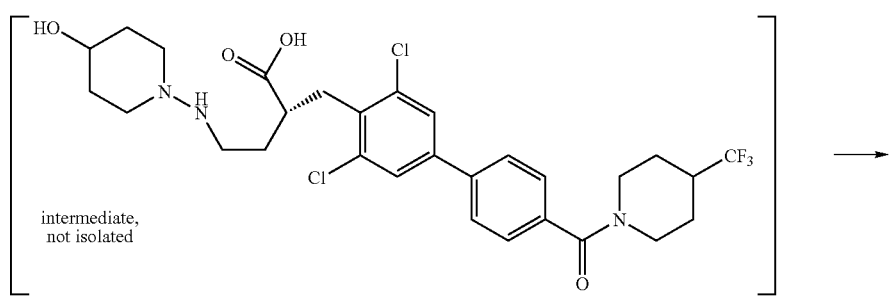
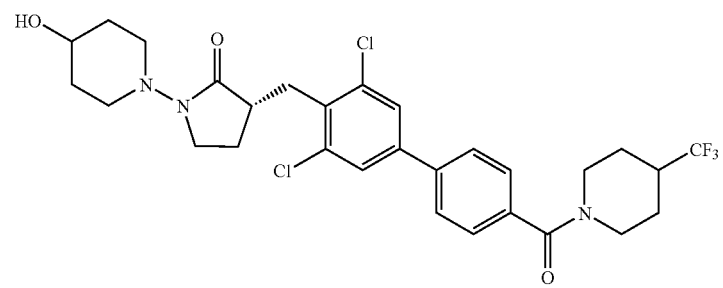

PREPARATION 37

(4-Bromo-phenyl)-(4-trifluoromethyl-piperidin-1-yl)-methanone

Dissolve 20.0 g (1 eq.) of 4-bromobenzoic in 200 mL of tetrahydrofuran and add 32.7 mL of N-methylmorpholine, 10.57 g of 4-trifluoromethylpiperidine hydrochloride and 12.1 g of 2-chloro-4,6-dimethoxy-1,3,5-triazine. After stirring for 16 h, filter the mixture and evaporate the solvent. Re-dissolve the mixture in methyl tert-butyl ether and wash with 1 N HCL followed by saturated aqueous sodium bicarbonate and water. Dry the organic layer over sodium sulfate and evaporate the solid to afford 15.5 g (83% yield) of the titled compound.

PREPARATION 38

Acetic acid 2,6-dichloro-benzyl Ester

Add 500 mL of dichloromethane to 100 g of 2,6-dichlorobenzyl alcohol followed by 117 mL of triethylamine. Cool the solution to 5° C. and add 65 mL of acetic anhydride. After 2.5 hr at room temperature, add another 10 mL of acetic anhydride, 20 mL of triethylamine and 0.5 g of 4-dimethylaminopyridine. Wash the organic layer with 1N HCl followed by saturated aqueous sodium bicarbonate and brine. Dry the organic layer (sodium sulfate) and evaporate to afford 131.5 g of the titled compound as an oil.

PREPARATION 39

Acetic acid 2,6-dichloro-4-(4,4,5,5-tetramethyl-[1,3,2]dioxaborolan-2-yl)-benzyl Ester Dissolve 62.2 g (1 eq.) of Acetic acid 2,6-dichloro-benzyl ester in 300 mL of heptane and add 71.4 g (1.02 eq.) of bis(pinacolato)diboron. Place the mixture under nitrogen and add 3.67 g (0.02 eq.) of di-mu-chlorobis[(1,2,5,6-eta)-1,5-cyclooctadiene)]diiridium and 2.56 g (0.06 eq.) of 2,2'-bypridine. Heat the mixture at reflux for 8 hours and then add another 52 g (0.74 eq.) of bis(pinacolato)diboron. Heat the mixture at reflux for 11 hours. Allow the mixture to cool to approximately 50° C. and add 500 mL of EtOAc and 10 g of Hyflo (diatomaceous earth) and filter through a pad of silica gel. Add 4 g of decolorizing carbon and filter. Add another 500 mL of EtOAc and wash the organic layer with water and brine. Dry the organic layer over sodium sulfate and filter. Evaporate the solvent to afford a brown residue. Dissolve the residue in 1 L of ethanol with heating. Add 5 g of decolorizing carbon and filter at 50° C. Evaporate the solvent to about 600 mL on a rotary evaporator at 40° C. to afford a slurry. Cool the slurry to 5° C. and collect the solid by filtration to afford 59.9 g (63% yield) of the titled compound.

PREPARATION 40

Acetic acid 3,5-dichloro-4'-(4-trifluoromethyl-piperidine-1-carbonyl)-biphenyl-4-ylmethyl Ester Dissolve 18.5 g (1 eq.) of Acetic acid 2,6-dichloro-4-(4,4,5,5-tetramethyl-[1,3,2]dioxaborolan-2-yl)-benzyl ester and 19.9 g (1.1 eq.) of (4-Bromo-phenyl)-(4-trifluoromethyl-piperidin-1-yl)-methanone in 190 mL of dimethoxyethane. Add 8.9 g of potassium carbonate, 95 mL of water, 0.24 g (0.02 eq.) of palladium acetate and 0.85 g (0.06 eq.) of triphenylphosphine. Heat the mixture at 80° C. for 2.5 hours. Stir the reaction mixture at room temperature overnight to afford a suspension. Add 7.4 g of potassium carbonate, 100 mL of water and 100 mL of methanol and stir the mixture at room temperature for 3 hours. Collect the solid by filtration and dry in a vacuum oven at 50° C. to afford 20.8 g (82% yield) of the titled compound.

PREPARATION 41

(3',5'-Dichloro-4'-hydroxymethyl-biphenyl-4-yl)-(4-trifluoromethyl-piperidin-1-yl)-methanone Dissolve 20 g (1 eq.) of Acetic acid 3,5-dichloro-4'-(4-trifluoromethyl-piperidine-1-carbonyl)-biphenyl-4-ylmethyl ester in 300 mL of methanol by heating to 33° C. Add 8.2 g of potassium carbonate at 25° C. and stir at ambient temperature for 5 hours. Add approximately 5 g of decolorizing carbon and filter the solution. Add water to the filtrate add remove some methanol on the rotary evaporator at 40° C. to afford a slurry. Collect the solid by filtration and dry under vacuum at 50° C. to afford 14.4 g (76% yield) of the titled compound.

PREPARATION 42

(4'-Bromomethyl-3',5'-dichloro-biphenyl-4-yl)-(4-trifluoromethyl-piperidin-1-yl)-methanone Dissolve (3',5'-Dichloro-4'-hydroxymethyl-biphenyl-4-yl)-(4-trifluoromethyl-piperidin-1-yl)-methanone (13 g, 1 eq.) in dichloromethane (200 mL) and cool to 0° C. Add triphenylphosphine (12.2 g, 1.5 eq.) followed by carbon tetrabromide (15.4 g, 1.5 eq.) in portions. Filter the reaction mixture and concentrate the filtrate. Chromatograph the filtrate on silica gel to afford 8.0 g (54% yield) of the titled compound.

PREPARATION 43

(3R,5S)-3-[3,5-Dichloro-4'-(4-trifluoromethyl-piperidine-1-carbonyl)-biphenyl-4-ylmethyl]-5-hydroxymethyl-dihydro-furan-2-one Dissolve (S)-5-Hydroxymethyl-dihydro-furan-2-one (1.21 g, 1 eq.) in THF (16 mL) and cool to −10° C. To this add dimethylethylamine (1.8 mL, 1.5 eq.) followed by the dropwise addition of TMS-Cl (1.46 mL, 1.1 eq.) Allow the reaction to stir for 1.5 hours at −10° C. Gas Chromatography confirms complete consumption of the (S)-5-Hydroxymethyl-dihydro-furan-2-one. Filter the mixture and wash with additional THF (25 mL). Cool the solution to −78° C. To this add LiHMDS (10 mL, 1.23 eq. to (4'-Bromomethyl-3',5'-dichloro-biphenyl-4-yl)-(4-trifluoromethyl-piperidin-1-yl)-methanone) dropwise and allow to stir at −78° C. for 30 minutes. Add (4'-Bromomethyl-3',5'-dichloro-biphenyl-4-yl)-(4-trifluoromethyl-piperidin-1-yl)-methanone (4 g, 0.76 eq. to (S)-5-Hydroxymethyl-dihydro-furan-2-one) and keep the reaction at −78° C. After 1 hour, TLC (50% EtOAc/Heptane) shows approximately 50% (4'-Bromomethyl-3',5'-dichloro-biphenyl-4-yl)-(4-trifluoromethyl-piperidin-1-yl)-methanone. At the end of the day, add LiHMDS (3 mL) and allow to warm to room temperature overnight. TLC (50% EtOAc/Heptane) still shows a small amount of (4'-Bromomethyl-3',5'-dichloro-biphenyl-4-yl)-(4-trifluoromethyl-piperidin-1-yl)-methanone. Quench the reaction with phosphoric acid:water (1:3) (50 mL) and allow to stir at room temperature for 1 hour. Extract the aqueous layer with EtOAc (3×100 mL). Combine the organic layers, dry and concentrate. Pass the crude oil through a silica gel plug (EtOAc) to give the titled compound (2.57 g, 60% yield).

PREPARATION 44

(R)-3-[3,5-Dichloro-4'-(4-trifluoromethyl-piperidine-1-carbonyl)-biphenyl-4-ylmethyl]-5-hydroxy-dihydro-furan-2-one Dissolve (3R,5S)-3-[3,5-Dichloro-4'-(4-trifluoromethyl-piperidine-1-carbonyl)-biphenyl-4-ylmethyl]-5-hydroxymethyl-dihydro-furan-2-one (1.5 g, 1 eq.) in THF (10 mL) and then add 2 N NaOH (3 mL). Allow the reaction to stir at room temperature for 1 hour with vigorous stirring. TLC (50% EtOAc/Heptane) shows the complete consumption of starting material. Add dropwise a solution of periodic acid (1.5 g, 2.3 eq.) in water (5 mL). The reaction becomes a white slurry with a small exotherm. After ~1 hour, TLC (50% EtOAc/Heptane) shows that the reaction is finished. Dilute the slurry with 1 N HCl (10 mL) and extract 3 times with EtOAc (150 mL total). Dry the organic layer and concentrate to give the titled compound as a white foamy solid (1 g, 68% yield).

EXAMPLE 19

(R)-3-[3,5-Dichloro-4'-(4-trifluoromethyl-piperidine-1-carbonyl)-biphenyl-4-ylmethyl]-1-(4-hydroxy-piperidin-1-yl)-pyrrolidin-2-one

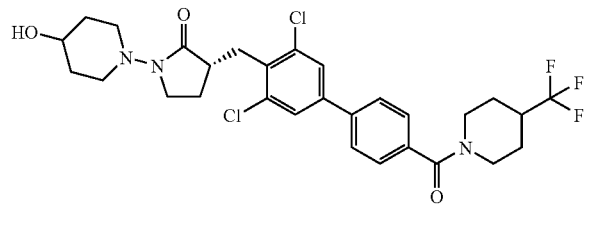

Dissolve 1-Amino-piperidin-4-ol (0.204 g, 1.1 eq.) in acetonitrile (3 mL) and heat the solution to 50° C. When the temperature reaches 35° C., add (R)-3-[3,5-Dichloro-4'-(4-trifluoromethyl-piperidine-1-carbonyl)-biphenyl-4-ylmethyl]-5-hydroxy-dihydro-furan-2-one (0.829 g, 1 eq.) and continue heating to 50° C. for 1 hour. Allow the reaction to cool to room temperature and add sodium triacetoxyborohydride (0.508 g, 1.5 eq.). Allow the reaction to stir overnight at room temperature. Add water and extract with EtOAc. Remove the solvent and chromatograph the residue on silica gel to afford 200 mg of the titled compound. MS (m/z): 598 (M+1, $^{35}$Cl), 600 (M+1, $^{37}$Cl).

In the following section enzyme and functional assays are described which are useful for evaluating the compounds of the invention.

11β-HSD Type 1 Enzyme Assay

Human 11β-HSD type 1 activity is measured by assaying NADPH production by fluorescence assay. Solid compounds are dissolved in DMSO to a concentration of 10 mM. Twenty microliters of each are then transferred to a column of a 96-well polypropylene Nunc plate where they are further diluted 50-fold followed by subsequent two-fold titration, ten times across the plate with additional DMSO using a Tecan Genesis 200 automated system. Plates are then transferred to a Tecan Freedom 200 system with an attached Tecan Temo 96-well head and an Ultra 384 plate reader. Reagents are supplied in 96-well polypropylene Nunc plates and are dispensed individually into black 96-well Molecular Devices High Efficiency assay plates (40 μL/well capacity) in the following fashion: 9 μL/well of substrate (2.22 mM NADP, 55.5 μM Cortisol, 10 mM Tris, 0.25% Prionex, 0.1% Triton X100), 3 μL/well of water to compound wells or 3 μL to control and standard wells, 6 μL/well recombinant human 11β-HSD type 1 enzyme, 2 μL/well of compound dilutions. For ultimate calculation of percent inhibition, a series of wells are added that represent assay minimum and maximum: one set containing substrate with 667 μM carbenoxolone (background), and another set containing substrate and enzyme without compound (maximum signal). Final DMSO concentration is 0.5% for all compounds, controls and standards. Plates are then placed on a shaker by the robotic arm of the Tecan for 15 seconds before being covered and stacked for a three hour incubation period at room temperature. Upon completion of this incubation, the Tecan robotic arm removes each plate individually from the stacker and places them in position for addition of 5 μL/well of a 250 μM carbenoxolone solution to stop the enzymatic reaction. Plates are then shaken once more for 15 seconds then placed into an Ultra 384 microplate reader (355EX/460EM) for detection of NADPH fluorescence.

Compounds of the invention can also tested for selectivity against 11-βHSD2 in an assay similar to that described for 11-βHSD1, but using the 11-βHSD2 enzyme. The assay using the 11-βHSD2 enzyme can be carried out by the methods described herein and supplemented by methods known in the art. Example 7 is observed to possess 145 fold greater inhibition of 11-βHSD1 enzyme as compared to the inhibition of 11-βHSD2.

Human Aortic Smooth Muscle Cell Assay

Primary human aortic smooth muscle cells (AoSMC) are cultured in 5% FBS growth medium to a passage number of 6, then pelleted by centrifugation and resuspended at a density of 9×10$^4$ cells/mL in 0.5% FBS assay medium containing 12 ng/mL hTNFα to induce expression of 11-β-HSD1. Cells are seeded into 96-well tissue culture assay plates at 100 μL/well (9×10$^3$ cells/well) and incubated for 48 hours at 37° C., 5% CO$_2$. Following induction, cells are incubated for 4 hours at 37° C., 5% CO$_2$ in assay medium containing test compounds then treated with 10 μL/well of 10 μM cortisone solubilized in assay medium, and incubated for 16 hours at 37° C., 5% CO$_2$. Medium from each well is transferred to a plate for subsequent analysis of cortisol using a competitive fluorescence resonance time resolved immunoassay. In solution, an allophycocyanin (APC)-cortisol conjugate and free cortisol analyte compete for binding to a mouse anti-cortisol antibody/Europium (Eu)-anti mouse IgG complex. Higher levels of free cortisol result in diminishing energy transfer from the Europium-IgG to the APC-cortisol complex resulting in less APC fluorescence. Fluorescent intensities for Europium and APC are measured using a LJL Analyst AD. Europium and APC excitation is measured using 360 nm excitation and 615 nm and 650 nm emission filters respectively. Time resolved parameters for Europuium were 1000 μs integration time with a 200 μs delay. APC parameters are set at 150 μs integration time with a 50 μs delay. Fluorescent intensities measured for APC are modified by dividing by the Eu fluorescence (APC/Eu). This ratio is then used to determine the unknown cortisol concentration by interpolation using a cortisol standard curve fitted with a 4-parameter logistic equation. These concentrations are then used to determine compound activity by plotting concentration versus % inhibition, fitting with a 4-parameter curve and reporting the IC$_{50}$.

All of the examples disclosed herein demonstrate activity in the human aortic smooth muscle cell assay with IC$_{50}$ of less than 300 nM. Data for example compounds in the human aortic smooth muscle cell assay are shown below:

| Example | Structure | IC$_{50}$ (nM) |
|---|---|---|
| 3 | 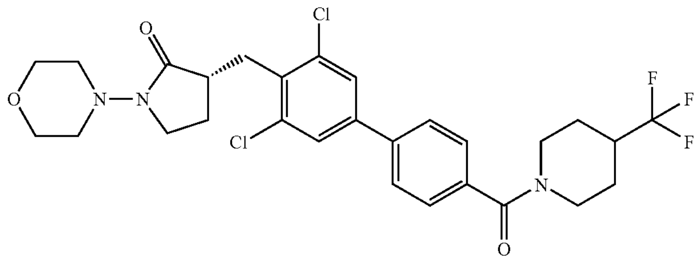 | 67 |
| 6 | 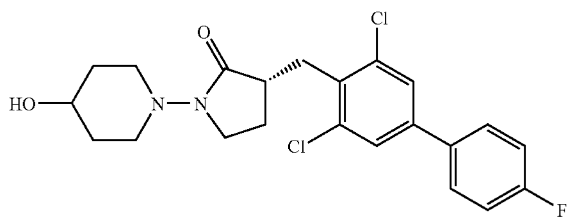 | 5.7 |
| 7 | 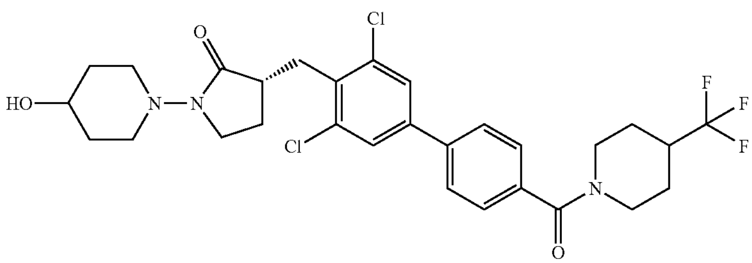 | 14.3 |
| 8 | 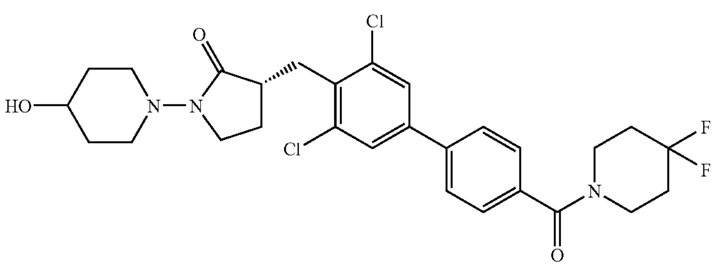 | 43 |

Acute In Vivo Cortisone Conversion Assay

In general, compounds are dosed orally into mice, the mice are challenged with a subcutaneous injection of cortisone at a set timepoint after compound injection, and the blood of each animal is collected some time later. Separated serum is then isolated and analyzed for levels of cortisone and cortisol by LC-MS/MS, followed by calculation of mean cortisol and percent inhibition of each dosing group. Specifically, male C57BL/6 mice are obtained from Harlan Sprague Dawley at average weight of 25 grams. Exact weights are taken upon arrival and the mice randomized into groups of similar weights. Compounds are prepared in 1% w-w HEC, 0.25% w-w polysorbate 80, 0.05% w-w Dow Corning antifoam #1510-US at various doses based on assumed average weight of 25 grams. Compounds are dosed orally, 200 μl per animal, followed by a subcutaneous dose, 200 μl per animal, of 30 mg/kg cortisone at 1 to 24 hours post compound dose. At 10 minutes post cortisone challenge, each animal is euthanized for 1 minute in a $CO_2$ chamber, followed by blood collection via cardiac puncture into serum separator tubes. Once fully clotted, tubes are spun at 2500×g, 4° C. for 15 minutes, the serum transferred to wells of 96-well plates (Corning Inc, Costar #4410, cluster tubes, 1.2 ml, polypropylene), and the plates are frozen at −20° C. until analysis by LC-MS/MS. For analysis, serum samples are thawed and the proteins are precipitated by the addition of acetonitrile containing d4-cortisol internal standard. Samples are vortex mixed and centrifuged. The supernatant is removed and dried under a stream of warm nitrogen. Extracts are reconstituted in methanol/water (1:1) and injected onto the LC-MS/MS system. The levels of cortisone and cortisol are assayed by selective reaction monitoring mode following positive ACPI ionization on a triple quadrupole mass spectrophotometer.

Data for example compounds in the acute in vivo cortisone conversion assay are shown below:

| Example | Structure | % Inhibition after 16 hours (dose of 10 (mg/kg)) |
|---|---|---|
| 3 | 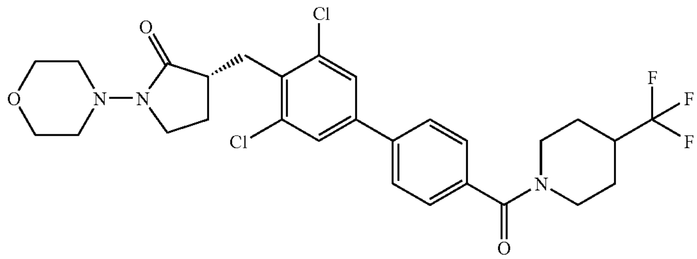 | 82 |
| 6 | 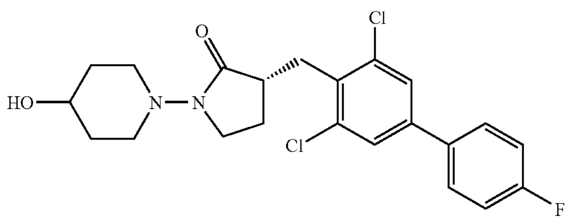 | 55 |
| 7 | 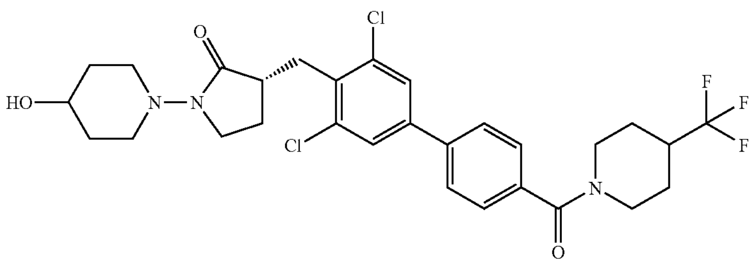 | 98 |
| 8 | 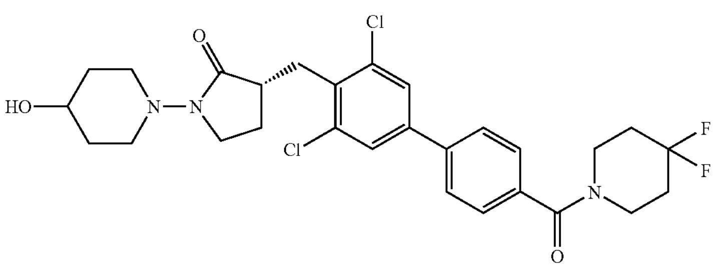 | 94 |

Pharmaceutically acceptable salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2002); S. M. Berge, et al., "Pharmaceutical Salts," *Journal of Pharmaceutical Sciences*, Vol. 66, No. 1, January 1977. The compounds of the present invention are preferably formulated as pharmaceutical compositions administered by a variety of routes. Most preferably, such compositions are for oral administration. Such pharmaceutical compositions and processes for preparing same are well known in the art. See, e.g. REMINGTON: THE SCIENCE AND PRACTICE OF PHARMACY (A. Gennaro, et al., eds., 19$^{th}$ ed., Mack Publishing Co., 1995).

The particular dosage of a compound of formula (I) or a pharmaceutically acceptable salt thereof required to constitute an effective amount according to this invention will depend upon the particular circumstances of the conditions to be treated. Considerations such as dosage, route of administration, and frequency of dosing are best decided by the attending physician. Generally, accepted and effective dose ranges for oral or parenteral administration will be from about 0.1 mg/kg/day to about 10 mg/kg/day which translates into about 6 mg to 600 mg, and more typically between 30 mg and 200 mg for human patients. Such dosages will be administered to a patient in need of treatment from one to three times each day or as often as needed to effectively treat a disease selected from those described herein.

One skilled in the art of preparing formulations can readily select the proper form and mode of administration depending upon the particular characteristics of the compound selected, the disorder or condition to be treated, the stage of the disorder or condition, and other relevant circumstances. (Remington's Pharmaceutical Sciences, 18th Edition, Mack Publishing Co. (1990)). The compounds claimed herein can be administered by a variety of routes. In effecting treatment of a patient afflicted with or at risk of developing the disorders described herein, a compound of formula (I) or a pharmaceutically acceptable salt thereof can be administered in any form or mode that makes the compound bioavailable in an effective amount, including oral and parenteral routes. For example, the active compounds can be administered rectally, orally, by inhalation, or by the subcutaneous, intramuscular, intravenous, transdermal, intranasal, rectal, occular, topical, sublingual, buccal, or other routes. Oral administration may be preferred for treatment of the disorders described herein. In those instances where oral administration is impossible or not preferred, the composition may be made available in a form suitable for parenteral administration, e.g., intravenous, intraperitoneal or intramuscular.

We claim:

1. A compound structurally represented by the formula:

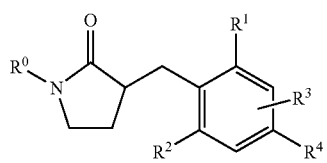

wherein
$R^0$ is

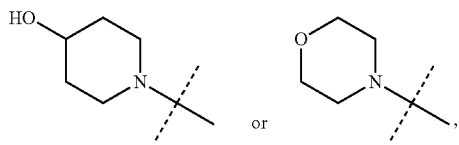

wherein the dashed line represents the point of attachment to the $R^0$ position;
$R^1$ is —H or -halogen;
$R^2$ is —H or -halogen;
$R^3$ is —H or -halogen;
$R^4$ is

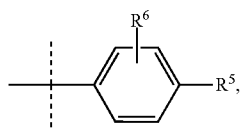

wherein the dashed line represents the point of attachment to the $R^4$ position;
$R^5$ is
  -halogen, —$(C_1-C_4)$alkyl (optionally substituted with 1 to 3 halogens), —$SO_2$—$(C_1-C_4)$alkyl,

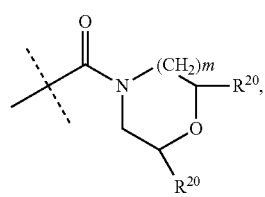

wherein the dashed line represents the point of attachment to the position indicated by $R^5$;
wherein m is 1;
wherein n is 1;
$R^6$ is
  —H or -halogen;
$R^7$ is
  H, -halogen, or —$(C_1-C_4)$alkyl(optionally substituted with 1 to 3 halogens);
$R^9$ is —H or -halogen;
$R^{20}$ is independently at each occurrence —H, or —$(C_1-C_3)$alkyl(optionally substituted with 1 to 3 halogens);
$R^{22}$ is independently at each occurrence —H or —$(C_1-C_6)$alkyl(optionally substituted with 1 to 3 halogens); and or a pharmaceutically acceptable salt thereof.

2. A compound of claim 1 wherein $R^0$ is

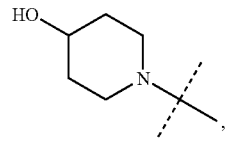

or a pharmaceutically acceptable salt thereof.

3. A compound of claim 1 wherein $R^0$ is

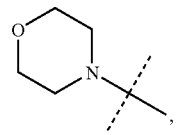

or a pharmaceutically acceptable salt thereof.

4. A compound of claim 2 wherein $R^1$ and $R^2$ are chlorine, or a pharmaceutically acceptable salt thereof.

5. A compound of claim 4 wherein $R^3$ is hydrogen, or a pharmaceutically acceptable salt thereof.

6. A compound of claim 5 wherein $R^4$ is

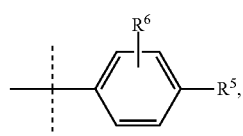

or a pharmaceutically acceptable salt thereof.

7. A compound of claim 5 wherein $R^4$ is

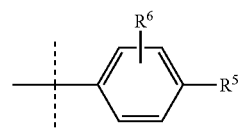

and $R^6$ is —H, or a pharmaceutically acceptable salt thereof.

8. A compound of claim 7 wherein $R^5$ is

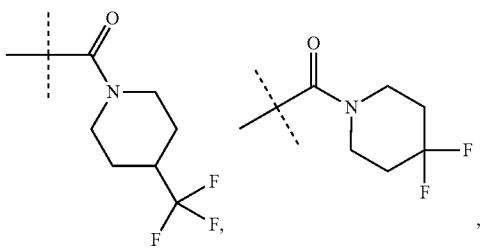

or

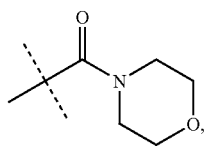

or a pharmaceutically acceptable salt thereof.

9. A compound of claim 7 wherein $R^5$ is

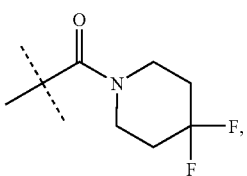

or a pharmaceutically acceptable salt thereof.

10. A compound of claim 7 wherein $R^5$ is

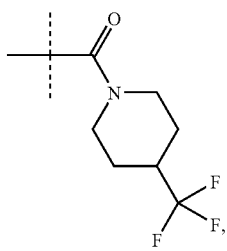

or a pharmaceutically acceptable salt thereof.

11. A compound of claim 7 wherein $R^5$ is chlorine or fluorine, or a pharmaceutically acceptable salt thereof.

12. A pharmaceutical composition which comprises a compound or salt of claim 6, and a pharmaceutically acceptable carrier.

13. A method of selectively reducing the glycemic level in a mammal comprising administering to a mammal in need thereof an 11-beta hydroxysteroid dehydrogenase 1 inhibiting dose of a compound or salt of claim 1.

14. A method for treating type 2 diabetes which comprises administering to a mammal in need of such treatment an effective amount of a compound or salt of claim 1.

15. A method for treating type 2 diabetes which comprises administering to a mammal in need of such treatment an effective amount of a pharmaceutical composition of claim 12.

16. A compound that is (R)-3-[3,5-Dichloro-4'-(4-trifluoromethyl-piperidine-1-carbonyl)-biphenyl-4-ylmethyl]-1-(4-hydroxy-piperidin-1-yl)-pyrrolidin-2-one, or a pharmaceutically acceptable salt thereof.

17. A compound that is (R)-3-[3,5-Dichloro-4'-(4,4-difluoro-piperidine-1-carbonyl)-biphenyl-4-ylmethyl]-1-(4-hydroxy-piperidin-1-yl)-pyrrolidin-2-one, or a pharmaceutically acceptable salt thereof.

18. An intermediate for preparing a compound of claim 16 wherein the intermediate is (R)-3-[3,5-Dichloro-4'-(4-trifluoromethyl-piperidine-1-carbonyl)-biphenyl-4-ylmethyl]-5-hydroxy-dihydro-furan-2-one.

19. Crystalline (R)-3-[3,5-Dichloro-4'-(4-trifluoromethyl-piperidine-1-carbonyl)-biphenyl-4-ylmethyl]-1-(4-hydroxy-piperidin-1-yl)-pyrrolidin-2-one anhydrate.

20. Crystalline (R)-3-[3,5-Dichloro-4'-(4-trifluoromethyl-piperidine-1-carbonyl)-biphenyl-4-ylmethyl]-1-(4-hydroxy-piperidin-1-yl)-pyrrolidin-2-one as claimed in claim 19 in substantially pure form.

21. Crystalline (R)-3-[3,5-Dichloro-4'-(4-trifluoromethyl-piperidine-1-carbonyl)-biphenyl-4-ylmethyl]-1-(4-hydroxy-piperidin-1-yl)-pyrrolidin-2-one as claimed in claim 20 characterized by peaks in the X-ray pattern at 2θ diffraction angles of 8.6±0.1° and 15.3±0.1°.

22. A compound that is (R)-3-[3,5-Dichloro-4'-(4-trifluoromethyl-piperidine-1-carbonyl)-biphenyl-4-ylmethyl]-1-(4-hydroxy-piperidin-1-yl)-pyrrolidin-2-one, or a pharmaceutically acceptable salt thereof, and a pharmaceutically acceptable carrier.

* * * * *